(12) United States Patent
Adlem et al.

(10) Patent No.: US 9,644,144 B2
(45) Date of Patent: *May 9, 2017

(54) BIMESOGENIC COMPOUNDS AND MESOGENIC MEDIA

(71) Applicant: Merck Patent GmbH, Darmstadt (DE)

(72) Inventors: Kevin Adlem, Bournemouth (GB); Owain Llyr Parri, Ringwood (GB); Rachel Tuffin, Chandler's Ford (GB); Patricia Eileen Saxton, Romsey (GB); Mariam Namutebi, Southampton (GB); Benjamin Snow, Chalfont St. Giles (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,527

(22) PCT Filed: Aug. 14, 2013

(86) PCT No.: PCT/EP2013/002438
§ 371 (c)(1),
(2) Date: Feb. 27, 2015

(87) PCT Pub. No.: WO2014/032772
PCT Pub. Date: Mar. 6, 2014

(65) Prior Publication Data
US 2015/0210921 A1  Jul. 30, 2015

(30) Foreign Application Priority Data

Aug. 29, 2012 (EP) .................... 12006131

(51) Int. Cl.
| | | |
|---|---|---|
| *C09K 19/02* | (2006.01) | |
| *C09K 19/20* | (2006.01) | |
| *C09K 19/58* | (2006.01) | |
| *C07C 255/50* | (2006.01) | |
| *C07C 25/13* | (2006.01) | |
| *C09K 19/04* | (2006.01) | |

(52) U.S. Cl.
CPC .......... *C09K 19/2014* (2013.01); *C07C 25/13* (2013.01); *C07C 255/50* (2013.01); *C09K 19/0258* (2013.01); *C09K 19/588* (2013.01); *C07C 2101/16* (2013.01); *C09K 2019/0444* (2013.01); *C09K 2019/0466* (2013.01); *C09K 2019/2035* (2013.01); *C09K 2019/2078* (2013.01)

(58) Field of Classification Search
CPC ............ C09K 19/0258; C09K 19/2014; C09K 2019/0444; C09K 2019/0466; C09K 2019/2035; C09K 2019/2078; C07C 255/50; C07C 2101/14; C07C 2101/16; C07C 25/13
See application file for complete search history.

(56) References Cited

U.S. PATENT DOCUMENTS

| | | | | |
|---|---|---|---|---|
| 7,544,400 | B2 * | 6/2009 | Goulding ............... | C09K 19/04 252/299.63 |
| 8,377,519 | B2 * | 2/2013 | Farrand .............. | C09K 19/0403 252/299.61 |
| 2014/0232977 | A1 * | 8/2014 | Adlem ............... | C09K 19/0258 349/186 |
| 2015/0090935 | A1 * | 4/2015 | Adlem ............... | C09K 19/0258 252/299.6 |
| 2015/0175883 | A1 * | 6/2015 | Adlem ............... | C09K 19/0258 252/299.65 |
| 2015/0175886 | A1 * | 6/2015 | Tuffin ............... | G02F 1/134309 349/139 |
| 2015/0203755 | A1 * | 7/2015 | Adlem ............... | C09K 19/0258 252/299.65 |
| 2015/0203756 | A1 * | 7/2015 | Adlem ............... | C09K 19/0258 252/299.63 |

FOREIGN PATENT DOCUMENTS

| | | |
|---|---|---|
| CN | 104364347 A | 2/2015 |
| EP | 2027232 B1 | 8/2011 |
| GB | 2356629 A | 5/2001 |

(Continued)

OTHER PUBLICATIONS

CAPLUS 2005:522127.*
CAPLUS 1932: 48539.*
CAPLUS 2005: 522127.*
CAPLUS 1995:879324.*
International Search Report dated Nov. 4, 2013 issued in corresponding PCT/EP2013/002438 application (pp. 1-3).
Chinese Search Report dated Dec. 24, 2015 issued in corresponding CN201380045323 application (1 page).
English translation of JP10251186A published on Sep. 22, 1998, Kobayashi Katsuhiko, Chisso Corp , entitled: Halogen-Substituted Benzene Derivative (abstract).

*Primary Examiner* — Shean C Wu
(74) *Attorney, Agent, or Firm* — Millen, White, Zelano, Branigan, P.C.

(57) ABSTRACT

The invention relates to bimesogenic compounds of formula I

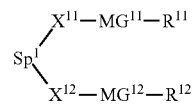

wherein $R^{11}$, $R^{12}$, $MG^{11}$, $MG^{12}$, $X^{11}$, $X^{12}$ and $Sp^1$ have the meaning given in claim 1, to the use of bimesogenic compounds of formula I in liquid crystal media and particular to flexoelectric liquid crystal devices comprising a liquid crystal medium according to the present invention.

26 Claims, No Drawings

(56) References Cited

FOREIGN PATENT DOCUMENTS

JP          10251186   A        9/1998
JP        2005154436   A    *   6/2005

* cited by examiner

BIMESOGENIC COMPOUNDS AND MESOGENIC MEDIA

The invention relates to bimesogenic compounds of formula I

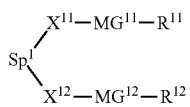

wherein $R^{11}$, $R^{12}$, $MG^{11}$, $MG^{12}$ and $Sp^1$ have the meaning given herein below, to the use of bimesogenic compounds of formula I in liquid crystal media and particular to flexoelectric liquid crystal devices comprising a liquid crystal medium according to the present invention.

Liquid Crystal Displays (LCDs) are widely used to display information. LCDs are used for direct view displays, as well as for projection type displays. The electro-optical mode which is employed for most displays still is the twisted nematic (TN)-mode with its various modifications. Besides this mode, the super twisted nematic (STN)-mode and more recently the optically compensated bend (OCB)-mode and the electrically controlled birefringence (ECB)-mode with their various modifications, as e.g. the vertically aligned nematic (VAN), the patterned ITO vertically aligned nematic (PVA)-, the polymer stabilized vertically aligned nematic (PSVA)-mode and the multi domain vertically aligned nematic (MVA)-mode, as well as others, have been increasingly used. All these modes use an electrical field, which is substantially perpendicular to the substrates, respectively to the liquid crystal layer. Besides these modes there are also electro-optical modes employing an electrical field substantially parallel to the substrates, respectively the liquid crystal layer, like e.g. the In Plane Switching (short IPS) mode (as disclosed e.g. in DE 40 00 451 and EP 0 588 568) and the Fringe Field Switching (FFS) mode. Especially the latter mentioned electro-optical modes, which have good viewing angle properties and improved response times, are increasingly used for LCDs for modern desktop monitors and even for displays for TV and for multimedia applications and thus are competing with the TN-LCDs.

Further to these displays, new display modes using cholesteric liquid crystals having a relatively short cholesteric pitch have been proposed for use in displays exploiting the so called "flexo-electric" effect. The term "liquid crystal", "mesomorphic compound" or "mesogenic compound" (also shortly referred to as "mesogen") means a compound that under suitable conditions of temperature, pressure and concentration can exist as a mesophase (nematic, smectic, etc.) or in particular as a LC phase. Non-amphiphilic mesogenic compounds comprise for example one or more calamitic, banana-shaped or discotic mesogenic groups.

Flexoelectric liquid crystal materials are known in prior art. The flexoelectric effect is described inter alia by Chandrasekhar, "Liquid Crystals", 2nd edition, Cambridge University Press (1992) and P. G. deGennes et al., "The Physics of Liquid Crystals", 2nd edition, Oxford Science Publications (1995).

In these displays the cholesteric liquid crystals are oriented in the "uniformly lying helix" arrangement (ULH), which also give this display mode its name. For this purpose, a chiral substance which is mixed with a nematic material induces a helical twist transforming the material into a chiral nematic material, which is equivalent to a cholesteric material. The term "chiral" in general is used to describe an object that is non-superimposable on its mirror image. "Achiral" (non-chiral) objects are objects that are identical to their mirror image. The terms chiral nematic and cholesteric are used synonymously in this application, unless explicitly stated otherwise. The pitch induced by the chiral substance ($P_0$) is in a first approximation inversely proportional to the concentration (c) of the chiral material used. The constant of proportionality of this relation is called the helical twisting power (HTP) of the chiral substance and defined by equation (1)

$$HTP = 1/(c \cdot P_0) \quad (1)$$

wherein
c is concentration of the chiral compound.

The uniform lying helix texture is realized using a chiral nematic liquid crystal with a short pitch, typically in the range from 0.2 μm to 1 μm, preferably of 1.0 μm or less, in particular of 0.5 μm or less, which is unidirectional aligned with its helical axis parallel to the substrates, e.g. glass plates, of a liquid crystal cell. In this configuration the helical axis of the chiral nematic liquid crystal is equivalent to the optical axis of a birefringent plate.

If an electrical field is applied to this configuration normal to the helical axis the optical axis is rotated in the plane of the cell, similar as the director of a ferroelectric liquid crystal rotate as in a surface stabilized ferroelectric liquid crystal display. The flexoelectric effect is characterized by fast response times typically ranging from 6 μs to 100 μs. It further features excellent grey scale capability.

The field induces a splay bend structure in the director which is accommodated by a tilt in the optical axis. The angle of the rotation of the axis is in first approximation directly and linearly proportional to the strength of the electrical field. The optical effect is best seen when the liquid crystal cell is placed between crossed polarizers with the optical axis in the unpowered state at an angle of 22.5° to the absorption axis of one of the polarizers. This angle of 22.5° is also the ideal angle of rotation of the electric field, as thus, by the inversion the electrical field, the optical axis is rotated by 45° and by appropriate selection of the relative orientations of the preferred direction of the axis of the helix, the absorption axis of the polarizer and the direction of the electric field, the optical axis can be switched from parallel to one polarizer to the center angle between both polarizers. The optimum contrast is then achieved when the total angle of the switching of the optical axis is 45°. In that case the arrangement can be used as a switchable quarter wave plate, provided the optical retardation, i.e. the product of the effective birefringence of the liquid crystal and the cell gap, is selected to be the quarter of the wave length. In this context the wavelength referred to is 550 nm, the wavelength for which the sensitivity of the human eye is highest, unless explicitly stated otherwise.

The angle of rotation of the optical axis ($\Phi$) is given in good approximation by formula (2)

$$\tan \Phi = \bar{e} P_0 E / (2\pi K) \quad (2)$$

wherein
$P_0$ is the undisturbed pitch of the cholesteric liquid crystal,
$\bar{e}$ is the average [$\bar{e} = \frac{1}{2}(e_{splay} + e_{bend})$] of the splay flexo-electric coefficient ($e_{splay}$) and the bend flexoelectric coefficient ($e_{bend}$),
E is the electrical field strength and
K is the average [$K = \frac{1}{2}(k_{11} + k_{33})$] of the splay elastic constant ($k_{11}$) and the bend elastic constant ($K_{33}$)
and wherein
$\bar{e}/K$ is called the flexo-elastic ratio.

This angle of rotation is half the switching angle in a flexoelectric switching element.

The response time (τ) of this electro-optical effect is given in good approximation by formula (3)

$$\tau = [P_0/(2\pi)]^2 \cdot \gamma/K \quad (3)$$

wherein

γ is the effective viscosity coefficient associated with the distortion of the helix.

There is a critical field ($E_c$) to unwind the helix, which can be obtained from equation (4)

$$E_c = (\pi^2/P_0) \cdot [k_{22}/(\epsilon_0 \cdot \Delta\epsilon)]^{1/2} \quad (4)$$

wherein $k_{22}$ is the twist elastic constant, $\epsilon_0$ is the permittivity of vacuum and $\Delta\epsilon$ is the dielectric anisotropy of the liquid crystal.

In this mode, however several problems still have to be resolved, which are, amongst others, difficulties in obtaining the required uniform orientation, an unfavorably high voltage required for addressing, which is incompatible with common driving electronics, a not really dark "off state", which deteriorates the contrast, and, last not least, a pronounced hysteresis in the electro-optical characteristics.

A relatively new display mode, the so-called uniformly standing helix (USH) mode, may be considered as an alternative mode to succeed the IPS, as it can show improved black levels, even compared to other display mode providing wide viewing angles (e.g. IPS, VA etc.).

For the USH mode, like for the ULH mode, flexoelectric switching has been proposed, using bimesogenic liquid crystal materials. Bimesogenic compounds are known in general from prior art (cf. also Hori, K., Iimuro, M., Nakao, A., Toriumi, H., J. Mol. Struc. 2004, 699, 23-29). The term "bimesogenic compound" relates to compounds comprising two mesogenic groups in the molecule. Just like normal mesogens they can form many mesophases, depending on their structure. In particular compounds of formula I induce a second nematic phase, when added to a nematic liquid crystal medium.

The term "mesogenic group" means in this context, a group with the ability to induce liquid crystal (LC) phase behaviour. The compounds comprising mesogenic groups do not necessarily have to exhibit an LC phase themselves. It is also possible that they show LC phase behaviour only in mixtures with other compounds. For the sake of simplicity, the term "liquid crystal" is used hereinafter for both mesogenic and LC materials.

However, due to the unfavorably high driving voltage required, to the relatively narrow phase range of the chiral nematic materials and to their irreversible switching properties, materials from prior art are not compatible for the use with current LCD driving schemes.

For displays of the USH and ULH mode, new liquid crystalline media with improved properties are required. Especially the birefringence (Δn) should be optimized for the optical mode. The birefringence Δn herein is defined in equation (5)

$$\Delta n = n_e - n_o \quad (5)$$

wherein $n_e$ is the extraordinary refractive index and $n_o$ is the ordinary refractive index, and the average refractive index $n_{av.}$ is given by the following equation (6).

$$n_{av.} = [(2n_o^2 + n_e^2)/3]^{1/2} \quad (6)$$

The extraordinary refractive index $n_e$ and the ordinary refractive index $n_o$ can be measured using an Abbe refractometer. Δn can then be calculated from equation (5).

Furthermore, for displays utilizing the USH or ULH mode the optical retardation d*Δn (effective) of the liquid crystal media should preferably be such that the equation (7)

$$\sin 2(\pi \cdot d \cdot \Delta n/\lambda) = 1 \quad (7)$$

wherein d is the cell gap and

λ is the wave length of light is satisfied. The allowance of deviation for the right hand side of equation (7) is +/−3%.

The wave length of light generally referred to in this application is 550 nm, unless explicitly specified otherwise.

The cell gap of the cells preferably is in the range from 1 μm to 20 μm, in particular within the range from 2.0 μm to 10 μm.

For the ULH/USH mode, the dielectric anisotropy (Δε) should be as small as possible, to prevent unwinding of the helix upon application of the addressing voltage. Preferably Δε should be slightly higher than 0 and very preferably be 0.1 or more, but preferably 10 or less, more preferably 7 or less and most preferably 5 or less. In the present application the term "dielectrically positive" is used for compounds or components with Δε>3.0, "dielectrically neutral" with −1.5≤Δε≤3.0 and "dielectrically negative" with Δε<−1.5. Δε is determined at a frequency of 1 kHz and at 20 ° C. The dielectric anisotropy of the respective compound is determined from the results of a solution of 10% of the respective individual compound in a nematic host mixture. In case the solubility of the respective compound in the host medium is less than 10% its concentration is reduced by a factor of 2 until the resultant medium is stable enough at least to allow the determination of its properties. Preferably the concentration is kept at least at 5%, however, in order to keep the significance of the results a high as possible. The capacitance of the test mixtures are determined both in a cell with homeotropic and with homogeneous alignment. The cell gap of both types of cells is approximately 20 μm. The voltage applied is a rectangular wave with a frequency of 1 kHz and a root mean square value typically of 0.5 V to 1.0 V, however, it is always selected to be below the capacitive threshold of the respective test mixture.

Δε is defined as ($\epsilon_\parallel - \epsilon_\perp$), whereas $\epsilon_{av.}$ is ($\epsilon_\parallel + 2\epsilon_\perp$)/3. The dielectric permittivity of the compounds is determined from the change of the respective values of a host medium upon addition of the compounds of interest. The values are extrapolated to a concentration of the compounds of interest of 100%. A typical The host mixture is disclosed in H. J. Coles et al., J. Appl. Phys. 2006, 99, 034104 and has the composition given in the table.

TABLE 1

| Host mixture composition | |
|---|---|
| Compound | Concentration |
| F-PGI-ZI9Z-GP-F | 25% |
| F-PGI-ZI11Z-GP-F | 25% |
| F-PGI-O5O-PP-N | 9.5% |
| F-PGI-O7O-PP-N | 39% |
| CD-1 | 1.5% |

Besides the above mentioned parameters, the media have to exhibit a suitably wide range of the nematic phase, a rather small rotational viscosity and an at least moderately high specific resistivity.

Similar liquid crystal compositions with short cholesteric pitch for flexoelectric devices are known from EP 0 971 016, GB 2 356 629 and Coles, H. J., Musgrave, B., Coles, M. J., and Willmott, J., J. Mater. Chem., 11, p. 2709-2716 (2001). EP 0 971 016 reports on mesogenic estradiols, which, as such, have a high flexoelectric coefficient. GB 2 356 629 suggests the use of bimesogenic compounds in flexoelectric devices. The flexoelectric effect herein has been investigated in pure cholesteric liquid crystal compounds and in mixtures of homologous compounds only so far. Most of these compounds were used in binary mixtures consisting of a chiral additive and a nematic liquid crystal material being either a simple, conventional monomesogenic material or a bimesogenic one. These materials do have several drawbacks for practical applications, like insufficiently wide temperature ranges of the chiral nematic—or cholesteric phase, too small flexoelectric ratios, small angles of rotation.

Compounds of the formulae

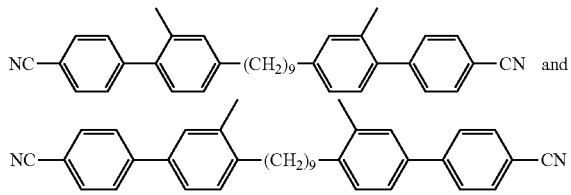

are mentioned in not yet published patent application PCT/EP 2012/002 480.

One aim of the invention was to provide improved flexoelectric devices that exhibit high switching angles and fast response times. Another aim was to provide liquid crystal materials with advantageous properties, in particular for use in flexoelectric displays that enable good uniform alignment over the entire area of the display cell without the use of a mechanical shearing process, good contrast, high switching angles and fast response times also at low temperatures. The liquid crystal mixtures and preferably also the single compounds should exhibit low melting points, broad chiral nematic phase ranges, short temperature independent pitch lengths and high flexoelectric coefficients. Other aims of the present invention are immediately evident to the person skilled in the art from the following detailed description.

The inventors have found out that the above aims can be surprisingly achieved by providing bimesogenic compounds according to the present invention. These compounds, when used in chiral nematic liquid crystal mixtures, lead to low melting points, broad chiral nematic phases. In particular, they exhibit relatively high values of the elastic constant $k_{11}$, low values of the bend elastic constant $k_{33}$ and high values of the flexoelectric coefficient.

Thus, the present invention relates to bimesogenic compounds of formula I

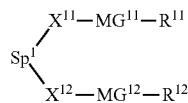

wherein $R^{11}$ and $R^{12}$ are each independently H, F, Cl, CN, NCS or a straight-chain or branched alkyl group with 1 to 25 C atoms which may be unsubstituted, mono- or polysubstituted by halogen or CN, it being also possible for one or more non-adjacent $CH_2$ groups to be replaced, in each occurrence independently from one another, by —O—, —S—, —NH—, —N(CH$_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another, preferably a polar group, more preferably F, Cl, CN, OCF$_3$, CF$_3$, halogen preferably is F, or Cl, more preferably F, $MG^{11}$ and $MG^{12}$ are each independently a mesogenic group, at least one of $MG^{11}$ and $MG^{12}$ comprises one, two or more 6-atomic rings, in case of comprising two or more 6-atomic rings at least two of these may be linked by a 2-atomic linking group, preferably selected from the group of linking groups —CO—O—, —O—CO—, —CH$_2$—O—, —O—CH$_2$—, —CF$_2$—O— and —O—CF$_2$—, $Sp^1$ is a spacer group comprising 1, 3 or 5 to 40 C atoms, wherein one or more non-adjacent and non-terminal $CH_2$ groups may also be replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH=CH— or —C≡C—, however in such a way that no two O-atoms are adjacent to one another, now two —CH=CH— groups are adjacent to each other and no two groups selected from —O—CO—, —S—CO—, —O—COO—, —CO—S—, —CO—O— and —CH=CH— are adjacent to each other, preferably —(CH$_2$)$_n$— (i.e. 1, n-alkylene with n C atoms), with n an integer, preferably from 3 to 19, more preferably from 3 to 11, most preferably an odd integer (i.e. 3, 5, 7, 9 or 11), wherein one or more H atoms in —(CH$_2$)$_n$— may independently of each other optionally be replaced by F or CH$_3$, $X^{11}$ and $X^{12}$ are each independently of one another a group selected from —CH=CH—, —C≡C—, —O—, —CF$_2$—O—, —O—CF$_2$—, —CO—O—, —O—CO—, —O—CO—O—, —S—, —CS—S—, —S—CS—, —CO—S—, —S—CO—, —S—CO—S— and —S—CS—S— or a single bond, preferably selected from —O—, —CO—O—, —O—CO—, —S—CO— and —CO—S— or a single bond, most preferably —CO—S—, —S—CO—, —O—CO— or —CO—O—, however under the condition that in —$X^{11}$-$Sp^1$-$X^{12}$— no two O-atoms are adjacent to one another, now two —CH=CH— groups are adjacent to each other and no two groups selected from —O—CO—, —S—CO—, —O—COO—, —CO—S—, —CO—O— and —CH=CH— are adjacent to each other, characterized in that at least one of $MG^{11}$ and $MG^{12}$ is 1,4-phenylene, which is substituted by at least one alkyl group having 1 to 5 C atoms, preferably CH$_3$ or C$_2$H$_5$, and/or by at least one alkoxy group —O—C$_n$H$_{2n+1}$ with 1 to 4 C atoms, i.e. n=1, 2, 3 or 4 or comprises a 1,4-phenylene, which is substituted by at least one alkyl group having 1 to 5 C atoms, preferably CH$_3$ or C$_2$H$_5$, and/or by at least one alkoxy group —O—C$_n$H$_{2n+1}$ with 1 to 4 C atoms, i.e. n=1, 2, 3 or 4, with the provision that compounds of the formulae

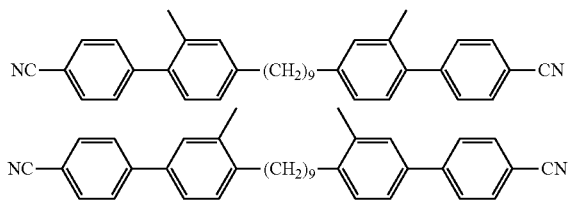

are preferably excluded from formula I.

It is possible and in some cases even preferable that one of $MG^{11}$ and $MG^{12}$ is or both $MG^{11}$ and $MG^{12}$ are
- 1,4-phenylene, which is substituted by at least one alkyl group having 1 to 5 C atoms, preferably $CH_3$ or $C_2H_5$, and by at least one alkoxy group —O—$C_nH_{2n+1}$ with 1 to 4 C atoms, i.e. n=1, 2, 3 or 4
- or one of $MG^{11}$ and $MG^{12}$ comprises or both $MG^{11}$ and $MG^{12}$ comprise a 1,4-phenylene, which is substituted by at least one alkyl group having 1 to 5 C atoms, preferably $CH_3$ or $C_2H_5$, and by at least one alkoxy group —O—$C_nH_{2n+1}$ with 1 to 4 C atoms, i.e. n=1, 2, 3 or 4.

Preferably in formula I
—$X^{11}$-$Sp^1$-$X^{12}$— is —O—CO-$Sp^1$-CO—O—, —O-$Sp^1$-O—, -$Sp^1$- or —S—CO-$Sp^1$-CO—S—, $Sp^1$ is —$(CH_2)_n$— with
n 1, 3 or an integer from 5 to 15, most preferably an odd (i.e. uneven) integer and, most preferably 7 or 9,
wherein one or more H atoms in —$(CH_2)_n$— may independently of each other optionally be replaced by F or $CH_3$.

Preferred compounds of formula I are compounds in which
$MG^{11}$ and $MG^{12}$ are independently from one another a group of (partial) formula II -$A^{11}$-$(Z^{11}$-$A^{12})_k$-  II wherein
$Z^{11}$ are, independently of each other in each occurrence, a single bond, —COO—, —OCO—, —O—CO—O—, —$OCH_2$—, —$CH_2O$—, —$OCF_2$—, —$CF_2O$—, —$CH_2CH_2$—, —$(CH_2)_4$—, —$CF_2CF_2$—, —CH=CH—, —CF=CF—, —CH=CH—COO—, —OCO—CH=CH— or —C≡C—, optionally substituted with one or more of F, S and/or Si, preferably a single bond,
at least one of
$A^{11}$ and $A^{12}$ present in at least one of $MG^{11}$ and $MG^{12}$ is 1,4-phenylene, which is substituted by an alkyl group having 1 to 5 C-atoms, preferably by an n-alkyl group, more preferably by methyl or ethyl, and the other
$A^{11}$ and $A^{12}$ are each independently in each occurrence 1,4-phenylene, wherein in addition one or more CH groups may be replaced by N, trans-1,4-cyclo-hexylene in which, in addition, one or two non-adjacent $CH_2$ groups may be replaced by O and/or S, 1,4-cyclohexenylene, 1,4-bicyclo-(2,2,2)-octylene, piperidine-1,4-diyl, naphthalene-2,6-diyl, decahydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1]decane-2,8-diyl, it being possible for all these groups to be unsubstituted, mono-, di-, tri- or tetrasubstituted with F, Cl, CN or alkyl, alkoxy, alkylcarbonyl or alkoxycarbonyl groups with 1 to 7 C atoms, wherein one or more H atoms may be substituted by F or Cl, preferably F, Cl, $CH_3$ or $CF_3$, and
k is 0, 1, 2, 3 or 4, preferably 1, 2 or 3 and, most preferably 1 or 2.

Especially preferred are compounds of formula I wherein the mesogenic groups $MG^{11}$ and $MG^{12}$ at each occurrence independently from each other comprise one, two or three six-membered rings, preferably two or three six-membered rings.

A smaller group of preferred mesogenic groups of formula II is listed below. For reasons of simplicity, Phe in these groups is 1,4-phenylene or alkyl-1,4-phenylene, PheL is a 1,4-phenylene group which is substituted by 1 to 4 groups L, with L being preferably F, Cl, CN, OH, $NO_2$ or an optionally fluorinated alkoxy or alkanoyl group with 1 to 7 C atoms, very preferably F, Cl, CN, OH, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, Cl, $CH_3$, $OCH_3$ and $COCH_3$ and Cyc is 1,4-cyclohexylene. This list comprises the subformulae shown below as well as their mirror images

| | |
|---|---|
| -Phe-Z-Phe- | II-1 |
| -Phe-Z-Cyc- | II-2 |
| -Cyc-Z-Cyc- | II-3 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| -Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 | wherein

Cyc is 1,4-cyclohexlene, preferably trans-1,4-cyclohexlene,

Phe is 1,4-phenylene or alkyl-1,4-phenylene,

PheL is 1,4-phenylene, which is substituted by one, two or three fluorine atoms, by one or two Cl atoms or by one Cl atom and one F atom, and Z has one of the meanings of $Z^{11}$ as given under partial formula II, at least one is preferably selected from —COO—, —OCO—, —O—CO—O—, —OCH$_2$—, —CH$_2$O—, —OCF$_2$— or —CF$_2$O—.

Particularly preferred are the sub-formulae II-1, II-4, II-5, II-7, II-8, II-14, II-15, II-16, II-17, II-18 and II-19.

In these preferred groups Z in each case independently has one of the meanings of $Z^{11}$ as given under formula I. Preferably one of Z is —COO—, —OCO—, —CH$_2$—O—, —O—CH$_2$—, —CF$_2$—O— or —O—CF$_2$—, more preferably —COO—, —O—CH$_2$— or —CF$_2$—O—, and the others preferably are a single bond.

Very preferably at least one of the mesogenic groups $MG^{11}$ and $MG^{12}$ is, and preferably both of them are each and independently, selected from the following formulae IIa to IIo and their mirror images wherein L is in each occurrence independently of each other R, F or Cl, preferably R or F, r is in each occurrence independently of each other 0, 1, 2 or 3, preferably 0, 1 or 2, R is alkyl having 1 to 5 C-atoms, preferably n-alkyl, more preferably methyl or ethyl, and at least one L present in at least one of $MG^{11}$ and $MG^{12}$ is R.

The group in these preferred formulae is very preferably denoting

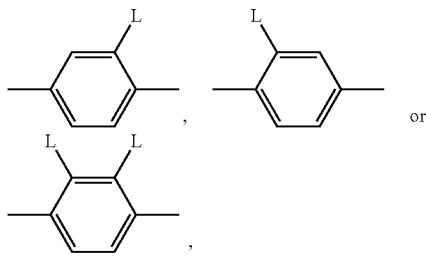

furthermore

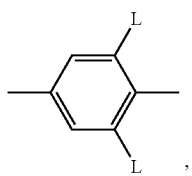

wherein
L is in each occurrence independently of each other R, F or Cl,
R is alkyl having 1 to 5 C-atoms, preferably n-alkyl, more preferably methyl or ethyl, and
at least one L present in at least one of $MG^{11}$ and $MG^{12}$ is R.

Particularly preferred are the sub-formulae IIa and IIc.

Most preferably one or both of $MG^{11}$ and $MG^{12}$ are selected from the following formulae IIa-1, IIa-2, IIc-1 and IIc-2

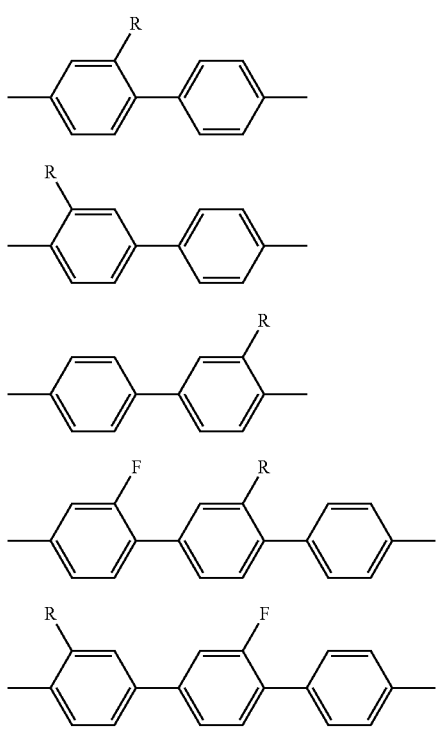

wherein
R is alkyl having 1 to 5 C-atoms, preferably n-alkyl, more preferably methyl or ethyl and, most preferably, is methyl.

In case of compounds with an unpolar group, $R^{11}$ and $R^{12}$ are preferably alkyl with up to 15 C atoms or alkoxy with 1 to 15 C atoms.

If $R^{11}$ or $R^{12}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl(=methoxymethyl), 2-(=ethoxymethyl) or 3-oxabutyl(=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In case of a compounds with a terminal polar group, $R^{11}$ and $R^{12}$ are selected from CN, $NO_2$, halogen, $OCH_3$, OCN, SCN, $COR^X$, $COOR^X$ or a mono- oligo- or polyfluorinated alkyl or alkoxy group with 1 to 4 C atoms. $R^X$ is optionally fluorinated alkyl with 1 to 4, preferably 1 to 3 C atoms. Halogen is preferably F or Cl, more preferably F.

Especially preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

In addition, compounds of formula I containing an achiral branched group $R^{11}$ and/or $R^{12}$ may occasionally be of importance, for example, due to a reduction in the tendency towards crystallisation. Branched groups of this type generally do not contain more than one chain branch. Preferred achiral branched groups are isopropyl, isobutyl(=methylpropyl), isopentyl (=3-methylbutyl), isopropoxy, 2-methylpropoxy and 3-methylbutoxy.

The spacer group $Sp^1$ is preferably a linear or branched alkylene group having 1, 3 or 5 to 40 C atoms, in particular 1, 3 or 5 to 25 C atoms, very preferably 1, 3 or 5 to 15 C atoms, and most preferably 5 to 15 C atoms, in which, in addition, one or more non-adjacent and non-terminal $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

"Terminal" $CH_2$ groups are those bound to the respective linking group "$X^{11}$" and/or "$X^{11}$" or directly to the respective mesogenic group $MG^{11}$ and/or $MG^{12}$. Accordingly, "non-terminal" $CH_2$ groups are not bound to the respective linking group "$X^{11}$" and/or "$X^{11}$" or directly to the respective mesogenic group $MG^{11}$ and/or $MG^{12}$.

Typical spacer groups are for example —$(CH_2)_o$—, —$(CH_2CH_2O)_p$—$CH_2CH_2$—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula I wherein Sp is denoting alkylene with 5 to 15 C atoms. Straight-chain alkylene groups are especially preferred.

Preferred are spacer groups, which are straight-chain alkylene with odd numbers of C atoms, preferably a having 5, 7, 9, 11, 13 or 15 C atoms, very preferred are straight-chain alkylene spacers having 7, 9, and 11 C atoms.

In another embodiment of the present invention the spacer groups are straight-chain alkylenes with even numbers of C atoms, preferably having 6, 8, 10, 12 and 14 C atoms. This embodiment is particularly preferred if one of $X^{11}$ and $X^{12}$ consists of one atom, i.e. is —S— or —O—, or of three atoms, e.g. is —S—CO—, —S—CO—S— or —S—CS—S—, and the other does not consist of one or three C atoms.

In a preferred embodiment of the present invention the inventive compounds of formula I comprise $Sp^1$ is denoting complete deuterated alkylene with 5 to 15 C atoms. Very preferred are deuterated straight-chain alkylene groups. Most preferred are partially deuterated straight-chain alkylene groups.

One preferred embodiment of the present invention are compounds of formula I wherein the mesogenic groups $R^{11}$-$M^{11}$-$X^{11}$— and $R^{12}$-$MG^{12}$-$X^{12}$— are identical to one another.

Another preferred embodiment of the present invention are compounds of formula I wherein $R^{11}$-$MG^{11}$-$X^{11}$— and $R^{12}$-$MG^{12}$-$X^{12}$— in formula I are are different from each other.

Preferred compounds of formula I are selected from the group of compounds of formulae IA to IC, preferably of formulae IA and/or IC,

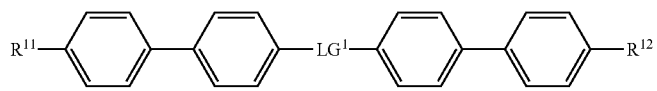

IA

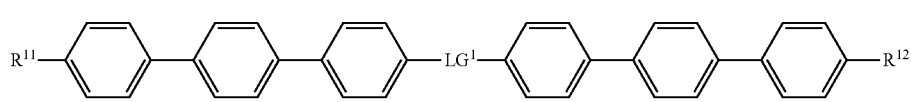

IB

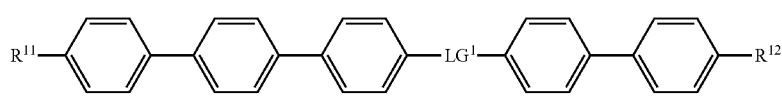

IC wherein
$LG^1$ is —$X^{11}$-$Sp^1$-$X^{12}$—,
and
the parameters have the respective meanings given above including the preferred meanings,
at least one of the 1,4-phenylene rings is substituted by an alkyl group and/or an alkoxy group and all of the 1,4-phenylene rings are optionally further substituted by one or more F or Cl-atoms, preferably at most by one Cl or by one or two F-atoms each.
$LG^1$ preferably is —O—CO-$Sp^1$-CO—O—, —O-$Sp^1$-O—, -$Sp^1$- or —S—CO-$Sp^1$-CO—S—,
$Sp^1$ preferably is —$(CH_2)_n$— with
n 1, 3 or an integer from 5 to 15, most preferably an odd (i.e. uneven) integer and, most preferably 7 or 9.

Particularly preferred compounds of formula IA are selected from the group of compounds of formulae IA-1 to IA-4

![IA-1 structure]

IA-1

![IA-2 structure]

IA-2

![IA-3 structure]

IA-3

-continued

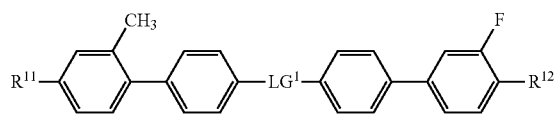

IA-4 wherein the parameters have the respective meanings given above including the preferred meanings and
preferably $R^{11}$ and $R^{12}$ are independently from each other as defined above, $OCF_3$, $CF_3$, F or CN, more preferably F or CN and most preferably CN Particularly preferred compounds of formula IB are selected from the group of compounds of formulae IB-1 to IB-3

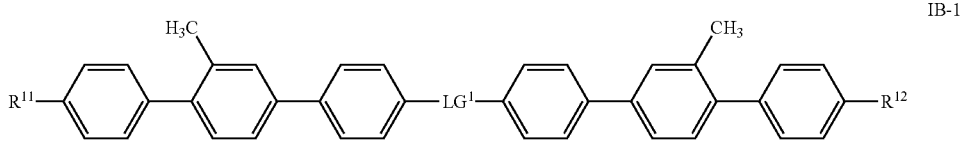

IB-1

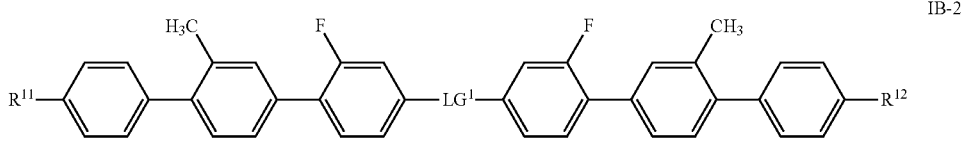

IB-2

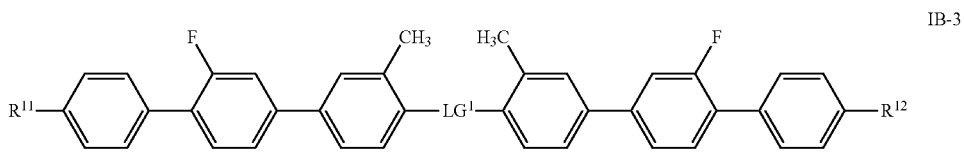

IB-3 wherein the parameters have the respective meanings given above including the preferred meanings and preferably $R^{11}$ and $R^{12}$ are independently from each other as defined above, $OCF_3$, $CF_3$, F or CN, more preferably F or CN and most preferably CN.

Particularly preferred compounds of formula IC are selected from the group of compounds of formulae IC-1 to IC-3

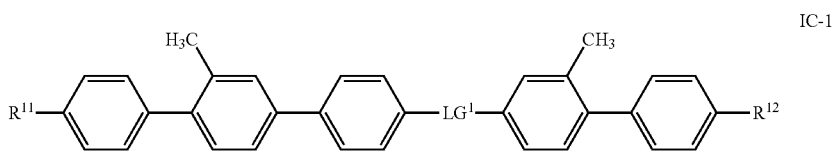

IC-1

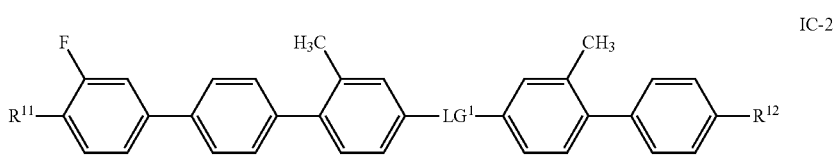

IC-2

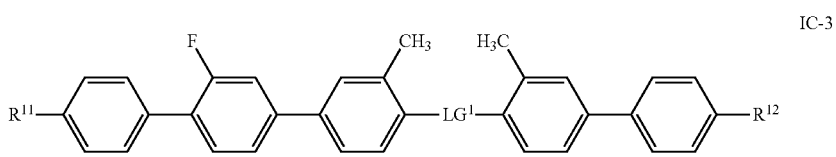

IC-3 wherein the parameters have the respective meanings given above including the preferred meanings and preferably $R^{11}$ and $R^{12}$ are independently from each other as defined above, $OCF_3$, $CF_3$, F or CN, more preferably F or CN and most preferably CN.

Particularly preferred compounds are selected from the group of formulae given above, which bear 0, 2 or 4 F atoms in lateral positions (i.e. as L).

In a preferred embodiment of the present invention $R^{11}$ is $OCF_3$ and $R^{12}$ is $OCF_3$, F or CN, preferably $OCF_3$ or CN and most preferably CN.

The compounds of formula I can be synthesized according to or in analogy to methods which are known per se and which are described in standard works of organic chemistry such as, for example, Houben-Weyl, Methoden der organischen Chemie, Thieme-Verlag, Stuttgart. A preferred method of preparation can be taken from the following synthesis schemes.

The compounds of formula I are preferably accessible according to the following general reaction schemes.

Reaction Scheme I

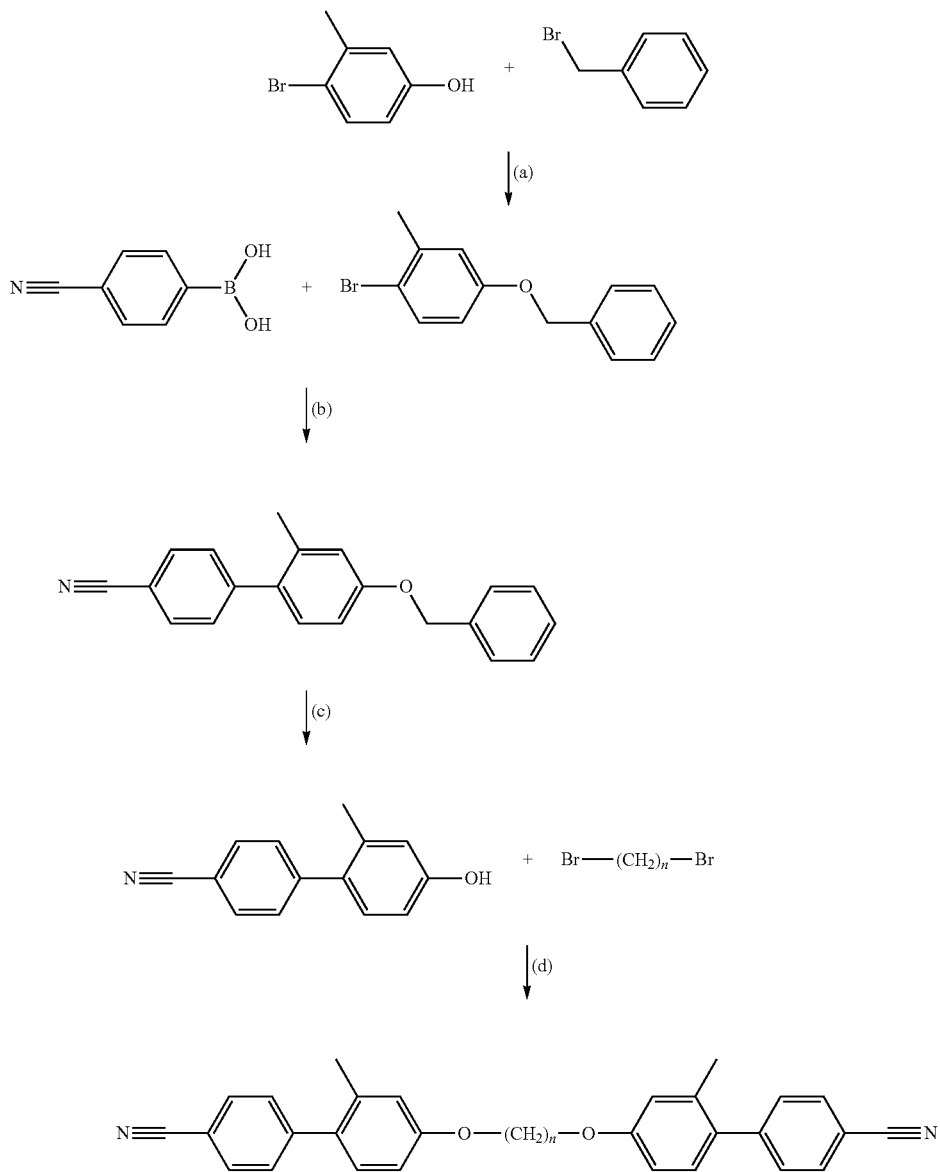

wherein n is an integer of 3 or from 5 to 15, preferably 5, 7 or 9, R independently in each occurrence has one of the meanings given for $R^{11}$ and in the second occurrence alternatively may have one of the additional meanings given for $R^{12}$ including the preferred meanings of these groups, and the conditions of the successive reactions are as follows:

a) $K_2CO_3$, MEK, reflux;
b) $K_3PO_4$, Dioxan, $H_2O$, $Pd(dppf)_2Cl_2$, reflux;
c) $H_2$, Pd/C; and
d) $K_2CO_3$, MEK, reflux.

All phenylene moieties shown in this scheme and in the following schemes may independently of each other be optionally bearing one, two or three, preferably by no or one, F or Cl, preferably F, atom.

An exemplary reaction scheme for the preparation of such a fluorinated compound is shown in the following scheme.

Reaction Scheme II

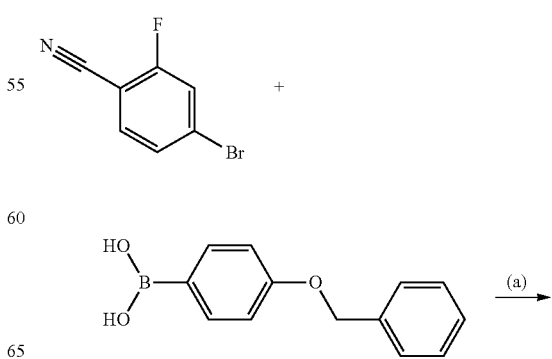

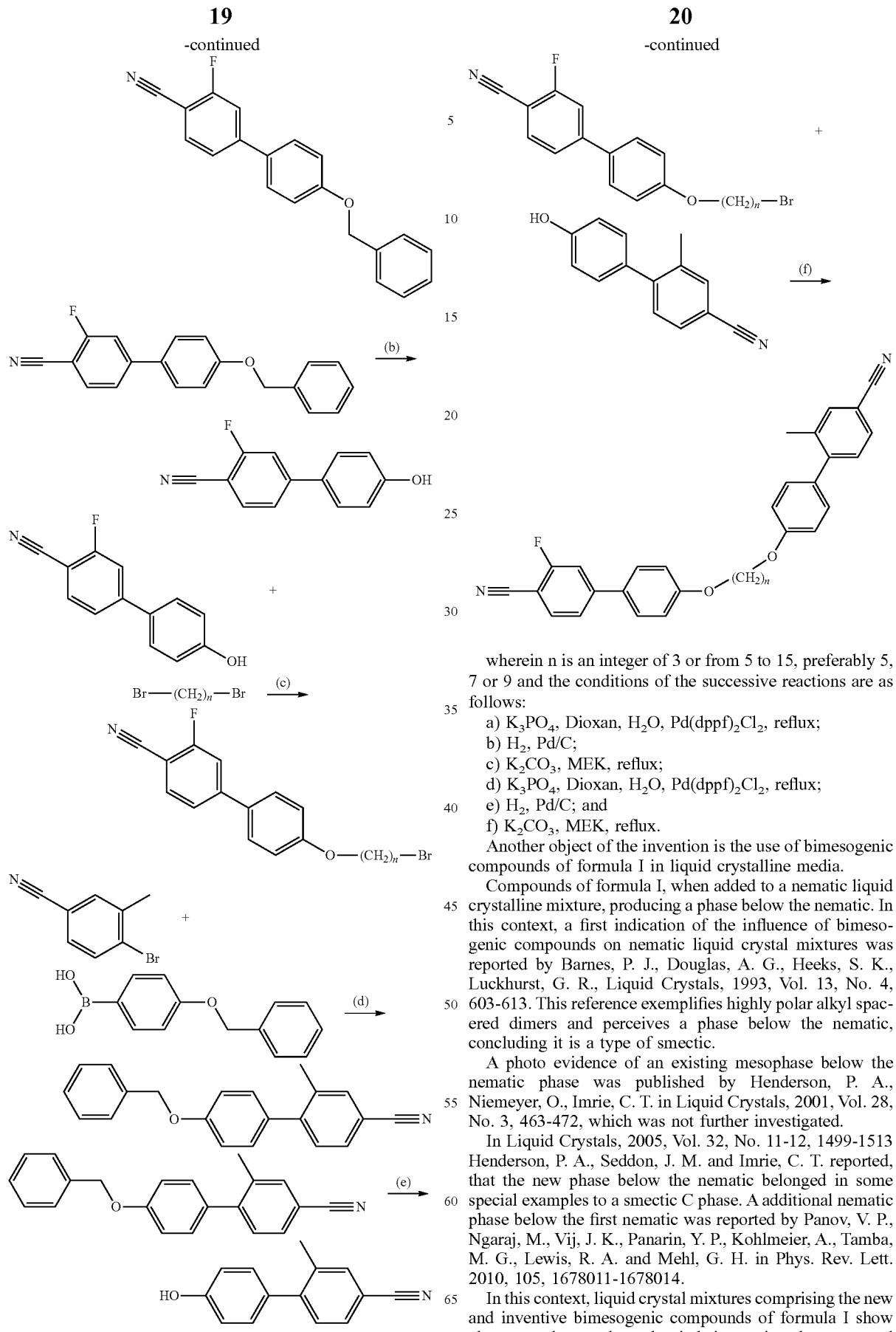

wherein n is an integer of 3 or from 5 to 15, preferably 5, 7 or 9 and the conditions of the successive reactions are as follows:

a) $K_3PO_4$, Dioxan, $H_2O$, $Pd(dppf)_2Cl_2$, reflux;
b) $H_2$, Pd/C;
c) $K_2CO_3$, MEK, reflux;
d) $K_3PO_4$, Dioxan, $H_2O$, $Pd(dppf)_2Cl_2$, reflux;
e) $H_2$, Pd/C; and
f) $K_2CO_3$, MEK, reflux.

Another object of the invention is the use of bimesogenic compounds of formula I in liquid crystalline media.

Compounds of formula I, when added to a nematic liquid crystalline mixture, producing a phase below the nematic. In this context, a first indication of the influence of bimesogenic compounds on nematic liquid crystal mixtures was reported by Barnes, P. J., Douglas, A. G., Heeks, S. K., Luckhurst, G. R., Liquid Crystals, 1993, Vol. 13, No. 4, 603-613. This reference exemplifies highly polar alkyl spacered dimers and perceives a phase below the nematic, concluding it is a type of smectic.

A photo evidence of an existing mesophase below the nematic phase was published by Henderson, P. A., Niemeyer, O., Imrie, C. T. in Liquid Crystals, 2001, Vol. 28, No. 3, 463-472, which was not further investigated.

In Liquid Crystals, 2005, Vol. 32, No. 11-12, 1499-1513 Henderson, P. A., Seddon, J. M. and Imrie, C. T. reported, that the new phase below the nematic belonged in some special examples to a smectic C phase. A additional nematic phase below the first nematic was reported by Panov, V. P., Ngaraj, M., Vij, J. K., Panarin, Y. P., Kohlmeier, A., Tamba, M. G., Lewis, R. A. and Mehl, G. H. in Phys. Rev. Lett. 2010, 105, 1678011-1678014.

In this context, liquid crystal mixtures comprising the new and inventive bimesogenic compounds of formula I show also a novel mesophase that is being assigned as a second nematic phase. This mesophase exists at a lower temperature than the original nematic liquid crystalline phase and has been observed in the unique mixture concepts presented by this application.

Accordingly, the bimesogenic compounds of formula I according to the present invention allow the second nematic phase to be induced in nematic mixtures that do not have this phase normally. Furthermore, varying the amounts of compounds of formula I allow the phase behaviour of the second nematic to be tailored to the required temperature.

The invention thus relates to a liquid-crystalline medium which comprises at least one compound of the formula I.

Some preferred embodiments of the mixtures according to the invention are indicated below.

Preferred are compounds of formula I wherein the mesogenic groups $MG^{11}$ and $MG^{12}$ at each occurrence independently from each other comprise one, two or three six-membered rings, preferably two or three six-membered rings.

Particularly preferred are the partial formulae II-1, II-4, II-6, II-7, II-13, II-14, II-15, II-16, II-17 and I-18.

Preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

Typical spacer groups ($Sp^1$) are for example —$(CH_2)_o$—, —$(CH_2CH_2O)_p$—$CH_2CH_2$—, with o being 1, 3 or an integer from 5 to 40, in particular from 1, 3 or 5 to 25, very preferably from 5 to 15, and p being an integer from 1 to 8, in particular 1, 2, 3 or 4.

Preferred are compounds of formula I wherein $R^{11}$-$MG^{11}$-$X^{11}$— and $R^{12}$-$MG^{12}$-$X^{12}$— in formula I are identical.

The media according to the invention preferably comprise one, two, three, four or more, preferably one, two or three, compounds of the formula I.

The amount of compounds of formula I in the liquid crystalline medium is preferably from 1 to 50%, in particular from 5 to 40%, very preferably 10 to 30% by weight of the total mixture.

In a preferred embodiment the liquid crystalline medium according to the present invention comprises additionally one or more compounds of formula III, like those or similar to those known from GB 2 356 629.

$$R^{31}\text{-}MG^{31}\text{-}X^{31}\text{-}Sp^3\text{-}X^{32}\text{-}MG^{32}\text{-}R^{32} \quad\quad III$$

wherein $R^{31}$ and $R^{32}$ are each independently H, F, Cl, CN, NCS or a straight-chain or branched alkyl group with 1 to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another, halogen preferably is F, or Cl, more preferably F, $MG^{31}$ and $MG^{32}$ are each independently a mesogenic group, $Sp^3$ is a spacer group comprising 5 to 40 C atoms, wherein one or more non-adjacent $CH_2$ groups may also be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—, and $X^{31}$ and $X^{32}$ are each independently —O—, —S—, —CO—, —COO—, —OCO—, —O—CO—O—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C— or a single bond, and with the condition that compounds of formula I are excluded.

The mesogenic groups $MG^{31}$ and $MG^{32}$ are preferably selected of formula II.

Especially preferred are compounds of formula III wherein $R^{31}$-$MG^{31}$-$X^{31}$— and $R^{32}$-$MG^{32}$-$X^{32}$— are identical.

Another preferred embodiment of the present invention relates to compounds of formula III wherein $R^{31}$-$MG^{31}$-$X^{31}$— and $R^{32}$-$MG^{32}$-$X^{32}$— are different.

Especially preferred are compounds of formula III wherein the mesogenic groups $MG^{31}$ and $MG^{32}$ comprise one, two or three six-membered rings very preferably are the mesogenic groups selected from formula II as listed below.

For $MG^{31}$ and $MG^{32}$ in formula III are particularly preferred are the subformulae II-1, II-4, II-6, II-7, II-13, II-14, II-15, II-16, II-17 and II-18. In these preferred groups Z in each case independently has one of the meanings of $Z^1$ as given in formula II. Preferably Z is —COO—, —OCO—, —$CH_2CH_2$—, —C≡C— or a single bond.

Very preferably the mesogenic groups $MG^{31}$ and $MG^{32}$ are selected from the formulae IIa to IIo and their mirror images.

In case of compounds with a non-polar group, $R^{31}$ and $R^{32}$ are preferably alkyl with up to 15 C atoms or alkoxy with 2 to 15 C atoms.

If $R^{31}$ or $R^{32}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl(=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In case of a compounds with a terminal polar group, $R^{31}$ and $R^{32}$ are selected from CN, $NO_2$, halogen, $OCH_3$, OCN, SCN, $COR^X$, $COOR^X$ or a mono- oligo- or polyfluorinated alkyl or alkoxy group with 1 to 4 C atoms. $R^X$ is optionally fluorinated alkyl with 1 to 4, preferably 1 to 3 C atoms. Halogen is preferably F or Cl, more preferably F.

Especially preferably $R^{31}$ and $R^{32}$ in formula III are selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of F, Cl, CN, $OCH_3$ and $OCF_3$.

As for the spacer group $Sp^3$ in formula III all groups can be used that are known for this purpose to the skilled in the art. The spacer group Sp is preferably a linear or branched alkylene group having 5 to 40 C atoms, in particular 5 to 25 C atoms, very preferably 5 to 15 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

Typical spacer groups are for example —(CH$_2$)$_o$—, —(CH$_2$CH$_2$O)$_p$—CH$_2$CH$_2$—, —CH$_2$CH$_2$—S—CH$_2$CH$_2$— or —CH$_2$CH$_2$—NH—CH$_2$CH$_2$—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula III wherein Sp$^3$ is denoting alkylene with 5 to 15 C atoms. Straight-chain alkylene groups are especially preferred.

In another preferred embodiment of the invention the chiral compounds of formula III comprise at least one spacer group Sp$^1$ that is a chiral group of the formula IV.

X$^{31}$ and X$^{32}$ in formula III denote preferably —O—, —CO—, —COO—, —OCO—, —O—CO—O— or a single bond. Particularly preferred are the following compounds selected from formulae III-1 to III-4:

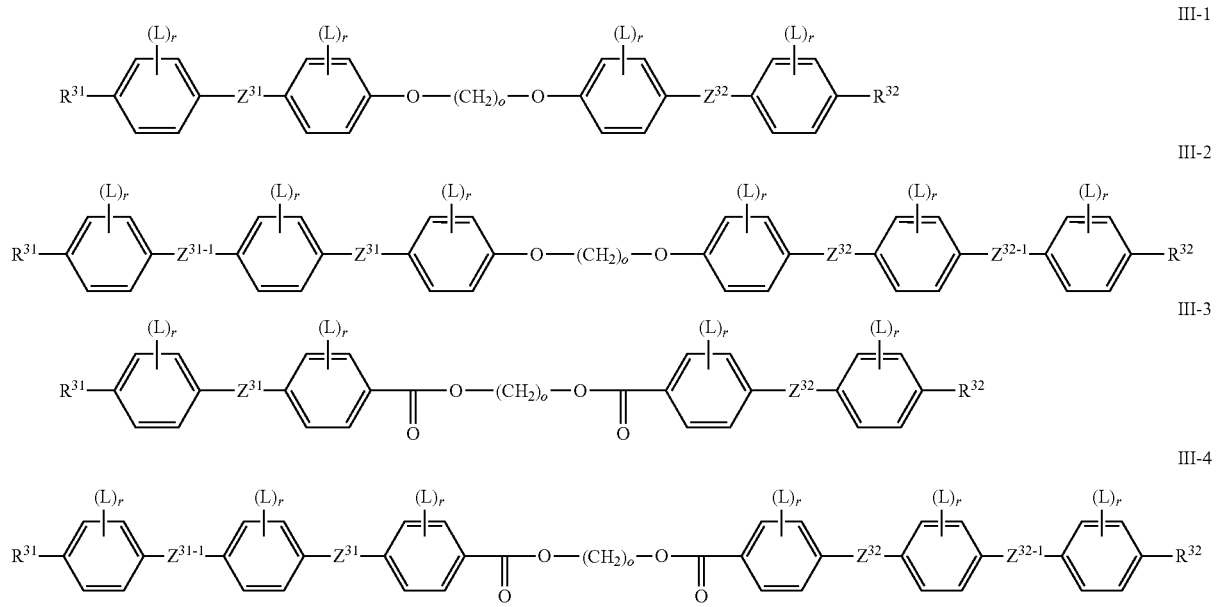

wherein R$^{31}$, R$^{32}$ have the meaning given under formula III, Z$^{31}$ and Z$^{31\text{-}I}$ are defined as Z$^{31}$ and Z$^{32}$ and Z$^{32\text{-}I}$ are respectively the reverse groups of Z$^{31}$ and Z$^{32\text{-}I}$ in formula III and o and r are independently at each occurrence as defined above, including the preferred meanings of these groups and wherein L is in each occurrence independently of each other preferably F, Cl, CN, OH, NO$_2$ or an optionally fluorinated alkyl, alkoxy or alkanoyl group with 1 to 7 C atoms, very preferably F, Cl, CN, OH, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, Cl, CH$_3$, OCH$_3$ and COCH$_3$ and from which compounds of formula I are excluded.

Particularly preferred mixtures according to the invention comprise one or more compounds of the formulae III-1a to III-1e and III-3a to III-3b.

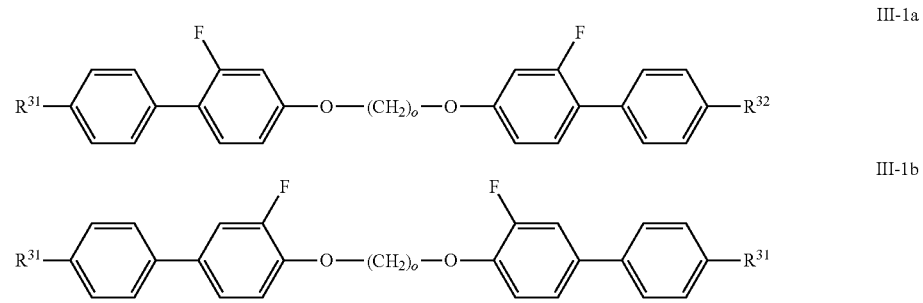

-continued

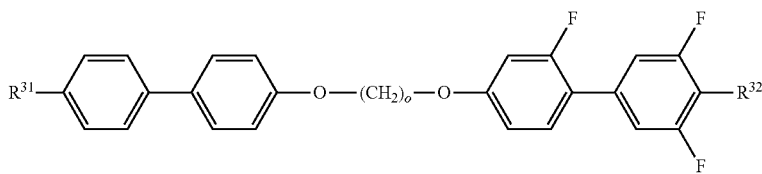
III-1c

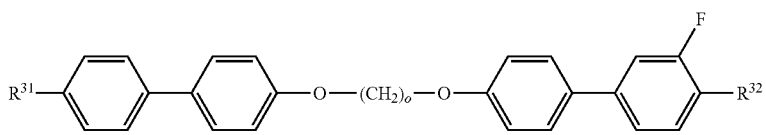
III-1d

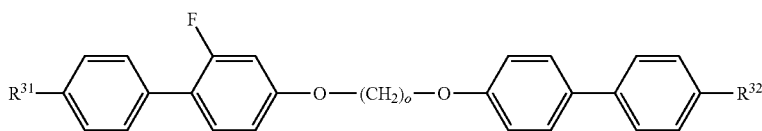
III-1e

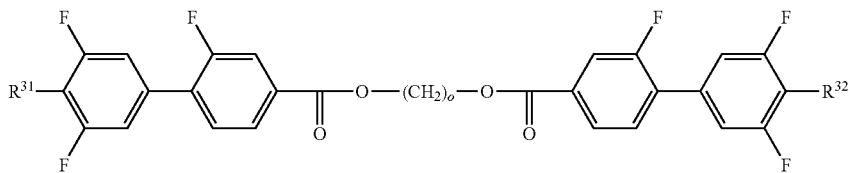
III-3a

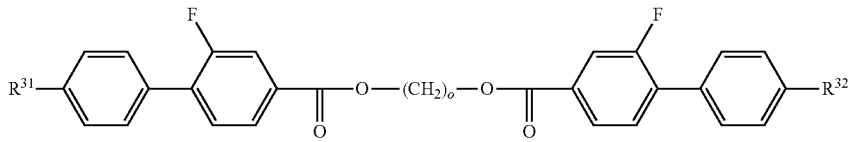
III-3b wherein the parameters are as defined above.

In a preferred embodiment of the invention the liquid crystalline medium is consisting of 2 to 25, preferably 3 to 15 compounds of formula III.

The amount of compounds of formula III in the liquid crystalline medium is preferably from 10 to 95%, in particular from 15 to 90%, very preferably 20 to 85% by weight of the total mixture.

Preferably, the proportion of compounds of the formulae III-1a and/or III-1b and/or III-1c and/or III-1e and or III-3a and/or III-3b in the medium as a whole is preferably at least 70% by weight.

Particularly preferred media according to the invention comprise at least one or more chiral dopants which themselves do not necessarily have to show a liquid crystalline phase and give good uniform alignment themselves.

Especially preferred are chiral dopants selected from formula IV

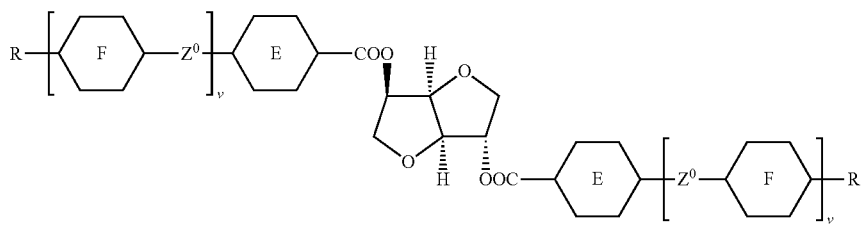
IV and formula V

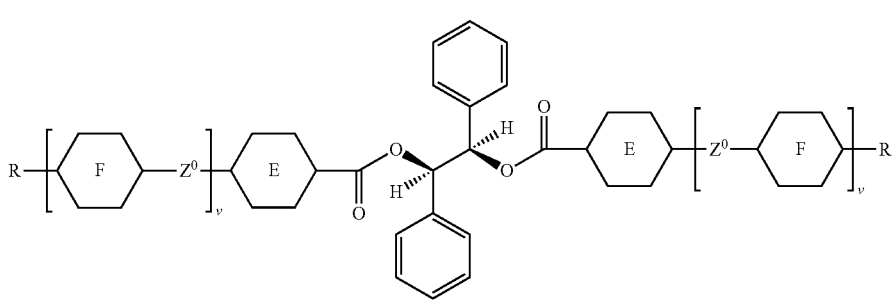

including the respective (S, S) enantiomer, wherein E and F are each independently 1,4-phenylene or trans-1,4-cyclohexylene, v is 0 or 1, $Z^0$ is —COO—, —OCO—, —CH$_2$CH$_2$— or a single bond, and R is alkyl, alkoxy or alkanoyl with 1 to 12 C atoms.

The compounds of formula IV and their synthesis are described in WO 98/00428. Especially preferred is the compound CD-1, as shown in table D below. The compounds of formula V and their synthesis are described in GB 2,328,207.

Especially preferred are chiral dopants with a high helical twisting power (HTP), in particular those disclosed in WO 98/00428.

Further typically used chiral dopants are e.g. the commercially available R/S-5011, CD-1, R/S-811 and CB-15 (from Merck KGaA, Darmstadt, Germany).

The above mentioned chiral compounds R/S-5011 and CD-1 and the compounds of formula IV and V exhibit a very high helical twisting power (HTP), and are therefore particularly useful for the purpose of the present invention.

The liquid crystalline medium preferably comprises preferably 1 to 5, in particular 1 to 3, very preferably 1 or 2 chiral dopants, preferably selected from the above formula IV, in particular CD-1, and/or formula V and/or R-5011 or S-5011, very preferably the chiral compound is R-5011, S-5011 or CD-1.

The amount of chiral compounds in the liquid crystalline medium is preferably from 1 to 20%, in particular from 1 to 15%, very preferably 1 to 10% by weight of the total mixture.

Further preferred are liquid crystalline media comprising one or more additives selected from the following formula VI

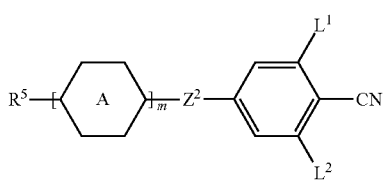

wherein
$R^5$ is alkyl, alkoxy, alkenyl or alkenyloxy with up to 12 C atoms,

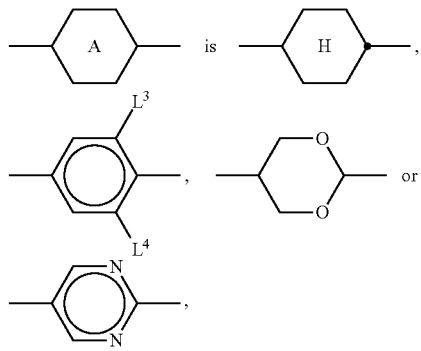

$L^1$ through $L^4$ are each independently H or F,
$Z^2$ is —COO—, —CH$_2$CH$_2$— or a single bond,
m is 1 or 2
Particularly preferred compounds of formula VI are selected from the following formulae

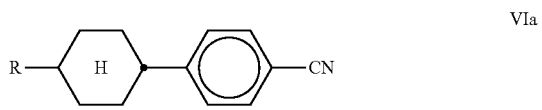

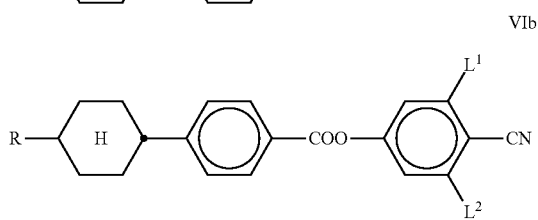

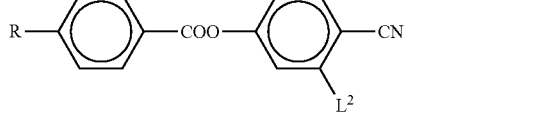

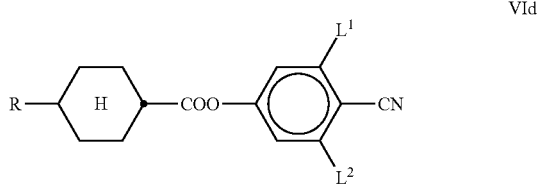

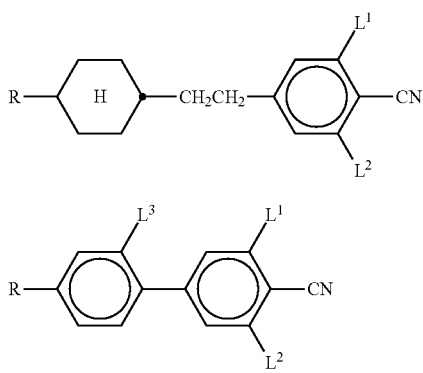

wherein, R has one of the meanings of $R^5$ above and $L^1$, $L^2$ and $L^3$ have the above meanings.

The liquid crystalline medium preferably comprises preferably 1 to 5, in particular 1 to 3, very preferably 1 or 2, preferably selected from the above formulae VIa to VIf, very preferably from formulae VIf.

The amount of suitable additives of formula VI in the liquid crystalline medium is preferably from 1 to 20%, in particular from 1 to 15%, very preferably 1 to 10% by weight of the total mixture.

The liquid crystal media according to the present invention may contain further additives in usual concentrations. The total concentration of these further constituents is in the range of 0.1% to 10%, preferably 0.1% to 6%, based on the total mixture. The concentrations of the individual compounds used each are preferably in the range of 0.1% to 3%. The concentration of these and of similar additives is not taken into consideration for the values and ranges of the concentrations of the liquid crystal components and compounds of the liquid crystal media in this application. This also holds for the concentration of the dichroic dyes used in the mixtures, which are not counted when the concentrations of the compounds respectively the components of the host medium are specified. The concentration of the respective additives is always given relative to the final doped mixture.

The liquid crystal media according to the present invention consists of several compounds, preferably of 3 to 30, more preferably of 4 to 20 and most preferably of 4 to 16 compounds. These compounds are mixed in conventional way. As a rule, the required amount of the compound used in the smaller amount is dissolved in the compound used in the greater amount. In case the temperature is above the clearing point of the compound used in the higher concentration, it is particularly easy to observe completion of the process of dissolution. It is, however, also possible to prepare the media by other conventional ways, e.g. using so called pre-mixtures, which can be e.g. homologous or eutectic mixtures of compounds or using so called multi-bottle-systems, the constituents of which are ready to use mixtures themselves.

Particularly preferred mixture concepts are indicated below: (the acronyms used are explained in Table A).

The mixtures according to the invention preferably comprise one or more compounds of formula I in a total concentration in the range from 1 to 50%, in particular from 5 to 40%, very preferably 10 to 30% by weight of the total mixture and/or
one or more compounds of formula III in a total concentration in the range from 10 to 95%, in particular from 15 to 90%, very preferably 20 to 85% by weight of the total mixture, preferably these compounds are selected from formulae III-1a to III-1e and III-3a to III-3b especially preferred they comprise
N—PGI—ZInZ-GP—N, preferably N—PG13 ZI7Z-GP—N and/or N—PGI—ZI9Z-GP—N preferably in concentrations >5%, in particular 10-30%, based on the mixture as a whole,
and/or
F—UIGI—ZInZ-GU—F, preferably F—UIGI—ZI9Z-GU—F, preferably in concentrations >5%, in particular 10-30%, based on the mixture as a whole,
and/or
F—PGI-OnO—PP—N, preferably F—PGI—O9O—PP—, preferably in concentrations of >1%, in particular 1-20%, based on the mixture as a whole,
and/or
N—PP-OnO—PG-OT, preferably N—PP—O7O—PG-OT, preferably in concentrations of >5%, in particular 5-30%, based on the mixture as a whole,
and/or
N—PP-OnO-GU—F, preferably N—PP—O9O-GU—F, preferably in concentrations of >1%, in particular 1-20%, based on the mixture as a whole,
and/or
F—PGI-OnO-GP—F, preferably F—PGI—O7O-GP—F and/or F—PGI—O9O-GP—F preferably in concentrations of >1%, in particular 1-20%, based on the mixture as a whole,
and/or
N-GIGIGI-n-GGG-N, in particular N-GIGIGI-9-GGG-N, preferably in concentration >5%, in particular 10-30%, based on the mixture as a whole,
and/or
N—PGI-n-GP—N, preferably N—PGI-9-GP—N, preferably in concentrations >5%, in particular 15-50%, based on the mixture as a whole,
and/or
one or more suitable additives of formula VI in a total concentration in the range from 1 to 20%, in particular from 1 to 15%, very preferably 1 to 10% by weight of the total mixture, preferably are these compounds selected from formula VIa to VIf, especially preferred they comprise
PP-n-N, preferably in concentrations of >1%, in particular 1-20%, based on the mixture as a whole,
and/or
one or more chiral compounds preferably in a total concentration in the range from 1 to 20%, in particular from 1 to 15%, very preferably 1 to 10% by weight of the total mixture, preferably these compounds are selected from formula IV, V, and R-5011 or S-5011, especially preferred they comprise
R-5011, S-5011 or CD-1, preferably in a concentration of >1%, in particular 1-20%, based on the mixture as a whole.

The bimesogenic compounds of formula I and the liquid crystalline media comprising them can be used in liquid crystal displays, such as STN, TN, AMD-TN, temperature compensation, guest-host, phase change or surface stabilized or polymer stabilized cholesteric texture (SSCT, PSCT) displays, in particular in flexoelectric devices, in active and passive optical elements like polarizers, compensators, reflectors, alignment layers, color filters or holographic elements, in adhesives, synthetic resins with anisotropic mechanical properties, cosmetics, diagnostics, liquid crystal pigments, for decorative and security applications, in nonlinear optics, optical information storage or as chiral dopants.

The compounds of formula I and the mixtures obtainable thereof are particularly useful for flexoelectric liquid crystal display. Thus, another object of the present invention is a flexoelectric display comprising one or more compounds of formula I or comprising a liquid crystal medium comprising one or more compounds of formula I.

The inventive bimesogenic compounds of formula I and the mixtures thereof can be aligned in their cholesteric phase into different states of orientation by methods that are known to the expert, such as surface treatment or electric fields. For example, they can be aligned into the planar (Grandjean) state, into the focal conic state or into the homeotropic state. Inventive compounds of formula I comprising polar groups with a strong dipole moment can further be subjected to flexoelectric switching, and can thus be used in electrooptical switches or liquid crystal displays.

The switching between different states of orientation according to a preferred embodiment of the present invention is exemplarily described below in detail for a sample of an inventive compound of formula I.

According to this preferred embodiment, the sample is placed into a cell comprising two plane-parallel glass plates coated with electrode layers, e.g. ITO layers, and aligned in its cholesteric phase into a planar state wherein the axis of the cholesteric helix is oriented normal to the cell walls. This state is also known as Grandjean state, and the texture of the sample, which is observable e.g. in a polarization microscope, as Grandjean texture.

Planar alignment can be achieved e.g. by surface treatment of the cell walls, for example by rubbing and/or coating with an alignment layer such as polyimide.

A Grandjean state with a high quality of alignment and only few defects can further be achieved by heating the sample to the isotropic phase, subsequently cooling to the chiral nematic phase at a temperature close to the chiral nematic-isotropic phase transition, and rubbing the cell.

In the planar state, the sample shows selective reflection of incident light, with the central wavelength of reflection depending on the helical pitch and the mean refractive index of the material.

When an electric field is applied to the electrodes, for example with a frequency from 10 Hz to 1 kHz, and an amplitude of up to 12 $V_{rms}$/m, the sample is being switched into a homeotropic state where the helix is unwound and the molecules are oriented parallel to the field, i.e. normal to the plane of the electrodes. In the homeotropic state, the sample is transmissive when viewed in normal daylight, and appears black when being put between crossed polarizers.

Upon reduction or removal of the electric field in the homeotropic state, the sample adopts a focal conic texture, where the molecules exhibit a helically twisted structure with the helical axis being oriented perpendicular to the field, i.e. parallel to the plane of the electrodes. A focal conic state can also be achieved by applying only a weak electric field to a sample in its planar state. In the focal conic state the sample is scattering when viewed in normal daylight and appears bright between crossed polarizers.

A sample of an inventive compound in the different states of orientation exhibits different transmission of light. Therefore, the respective state of orientation, as well as its quality of alignment, can be controlled by measuring the light transmission of the sample depending on the strength of the applied electric field. Thereby it is also possible to determine the electric field strength required to achieve specific states of orientation and transitions between these different states.

In a sample of an inventive compound of formula I, the above described focal conic state consists of many disordered birefringent small domains. By applying an electric field greater than the field for nucleation of the focal conic texture, preferably with additional shearing of the cell, a uniformly aligned texture is achieved where the helical axis is parallel to the plane of the electrodes in large, well-aligned areas. In accordance with the literature on state of the art chiral nematic materials, such as P. Rudquist et al., Liq. Cryst. 23 (4), 503 (1997), this texture is also called uniformly-lying helix (ULH) texture. This texture is required to characterize the flexoelectric properties of the inventive compound.

The sequence of textures typically observed in a sample of an inventive compound of formula I on a rubbed polyimide substrate upon increasing or decreasing electric field is given below:

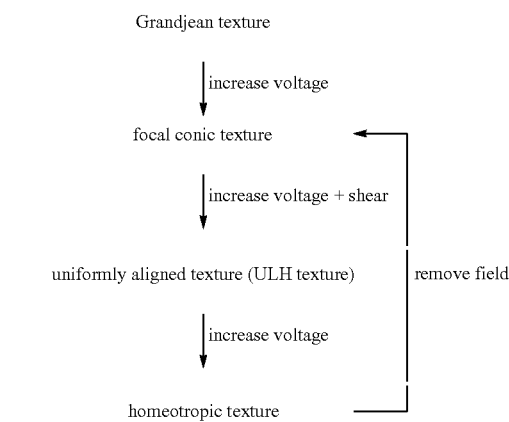

Starting from the ULH texture, the inventive flexoelectric compounds and mixtures can be subjected to flexoelectric switching by application of an electric field. This causes rotation of the optic axis of the material in the plane of the cell substrates, which leads to a change in transmission when placing the material between crossed polarizers. The flexoelectric switching of inventive materials is further described in detail in the introduction above and in the examples.

It is also possible to obtain the ULH texture, starting from the focal conic texture, by applying an electric field with a high frequency, of for example 10 kHz, to the sample whilst cooling slowly from the isotropic phase into the cholesteric phase and shearing the cell. The field frequency may differ for different compounds.

The bimesogenic compounds of formula I are particularly useful in flexoelectric liquid crystal displays as they can easily be aligned into macroscopically uniform orientation, and lead to high values of the elastic constant $k_{11}$ and a high flexoelectric coefficient e in the liquid crystal medium.

The liquid crystal medium preferably exhibits a $k_{11}$<1× $10^{-10}$ N, preferably <2×$10^{-11}$ N, and a flexoelectric coefficient e>1×$10^{-11}$ C/m, preferably >1×$10^{-10}$ C/m.

Apart from the use in flexoelectric devices, the inventive bimesogenic compounds as well as mixtures thereof are also suitable for other types of displays and other optical and electrooptical applications, such as optical compensation or polarizing films, color filters, reflective cholesterics, optical rotatory power and optical information storage.

A further aspect of the present invention relates to a display cell wherein the cell walls exhibit hybrid alignment conditions. The term "hybrid alignment" or orientation of a liquid crystal or mesogenic material in a display cell or between two substrates means that the mesogenic groups adjacent to the first cell wall or on the first substrate exhibit homeotropic orientation and the mesogenic groups adjacent to the second cell wall or on the second substrate exhibit planar orientation.

The term "homeotropic alignment" or orientation of a liquid crystal or mesogenic material in a display cell or on a substrate means that the mesogenic groups in the liquid crystal or mesogenic material are oriented substantially perpendicular to the plane of the cell or substrate, respectively.

The term "planar alignment" or orientation of a liquid crystal or mesogenic material in a display cell or on a substrate means that the mesogenic groups in the liquid crystal or mesogenic material are oriented substantially parallel to the plane of the cell or substrate, respectively.

A flexoelectric display according to a preferred embodiment of the present invention comprises two plane parallel substrates, preferably glass plates covered with a transparent conductive layer such as indium tin oxide (ITO) on their inner surfaces, and a flexoelectric liquid crystalline medium provided between the substrates, characterized in that one of the inner substrate surfaces exhibits homeotropic alignment conditions and the opposite inner substrate surface exhibits planar alignment conditions for the liquid crystalline medium.

Planar alignment can be achieved e.g. by means of an alignment layer, for example a layer of rubbed polyimide or sputtered $SiO_x$, that is applied on top of the substrate.

Alternatively it is possible to directly rub the substrate, i.e. without applying an additional alignment layer. For example, rubbing can be achieved by means of a rubbing cloth, such as a velvet cloth, or with a flat bar coated with a rubbing cloth. In a preferred embodiment of the present invention rubbing is achieved by means of a at least one rubbing roller, like e.g. a fast spinning roller that is brushing across the substrate, or by putting the substrate between at least two rollers, wherein in each case at least one of the rollers is optionally covered with a rubbing cloth. In another preferred embodiment of the present invention rubbing is achieved by wrapping the substrate at least partially at a defined angle around a roller that is preferably coated with a rubbing cloth.

Homeotropic alignment can be achieved e.g. by means of an alignment layer coated on top of the substrate. Suitable aligning agents used on glass substrates are for example alkyltrichlorosilane or lecithine, whereas for plastic substrate thin layers of lecithine, silica or high tilt polyimide orientation films as aligning agents may be used. In a preferred embodiment of the invention silica coated plastic film is used as a substrate.

Further suitable methods to achieve planar or homeotropic alignment are described for example in J. Cognard, Mol. Cryst. Liq. Cryst. 78, Supplement 1, 1-77 (1981).

By using a display cell with hybrid alignment conditions, a very high switching angle of flexoelectric switching, fast response times and a good contrast can be achieved.

The flexoelectric display according to present invention may also comprise plastic substrates instead of glass substrates. Plastic film substrates are particularly suitable for rubbing treatment by rubbing rollers as described above.

Another object of the present invention is that compounds of formula I, when added to a nematic liquid crystalline mixture, produce a phase below the nematic.

Accordingly, the bimesogenic compounds of formula I according to the present invention allow the second nematic phase to be induced in nematic mixtures that do not show evidence of this phase normally. Furthermore, varying the amounts of compounds of formula I allow the phase behaviour of the second nematic to be tailored to the required temperature.

Examples for this are given and the mixtures obtainable thereof are particularly useful for flexoelectric liquid crystal display. Thus, another object of the present invention is liquid crystal media comprising one or more compounds of formula I exhibiting a second nematic phase.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

Throughout the present application it is to be understood that the angles of the bonds at a C atom being bound to three adjacent atoms, e.g. in a C=C or C=O double bond or e.g. in a benzene ring, are 120° and that the angles of the bonds at a C atom being bound to two adjacent atoms, e.g. in a C≡C or in a C≡N triple bond or in an allylic position C=C=C are 180°, unless these angles are otherwise restricted, e.g. like being part of small rings, like 3-, 5- or 5-atomic rings, notwithstanding that in some instances in some structural formulae these angles are not represented exactly.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The total concentration of all compounds in the media according to this application is 100%.

In the foregoing and in the following examples, unless otherwise indicated, all temperatures are set forth uncorrected in degrees Celsius and all parts and percentages are by weight.

The following abbreviations are used to illustrate the liquid crystalline phase behavior of the compounds: K=crystalline; N=nematic; N2 32 second nematic; S or Sm=smectic; Ch=cholesteric; I=isotropic; Tg=glass transition. The numbers between the symbols indicate the phase transition temperatures in ° C.

In the present application and especially in the following examples, the structures of the liquid crystal compounds are represented by abbreviations, which are also called "acronyms". The transformation of the abbreviations into the corresponding structures is straight forward according to the following three tables A to C.

All groups $C_nH_{2n+1}$, $C_mH_{2m+1}$, and $C_lH2_{l+1}$ are preferably straight chain alkyl groups with n, m and l C-atoms, respectively, all groups $C_nH_{2n}$, $C_mH_{2m}$ and $C_lH_{2l}$ are preferably $(CH_2)_n$, $(CH_2)_m$ and $(CH_2)_l$, respectively and —CH═CH— preferably is trans-respectively E vinylene.

Table A lists the symbols used for the ring elements, table B those for the linking groups and table C those for the symbols for the left hand and the right hand end groups of the molecules.

Table D lists exemplary molecular structures together with their respective codes.

TABLE A

| Ring Elements | |
|---|---|
| C |  |
| D | 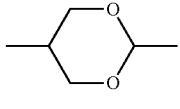 |
| A | 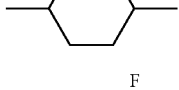 |
| G | 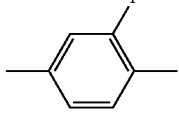 |
| G(Cl) | 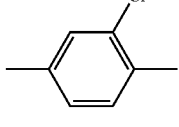 |
| G(n) | 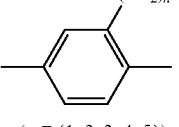 |
| | (n ∈ {1; 2; 3; 4; 5}) |
| U | 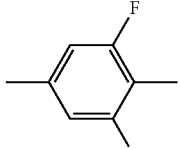 |
| Y | 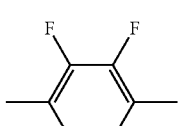 |

TABLE A-continued

| Ring Elements | |
|---|---|
| M | 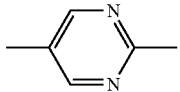 |
| N | 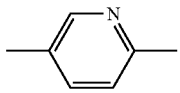 |
| P | 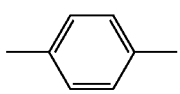 |
| DI | 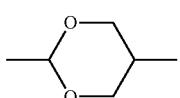 |
| AI | 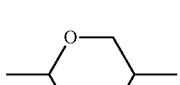 |
| GI | 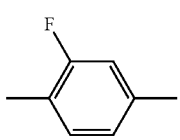 |
| GI(Cl) | 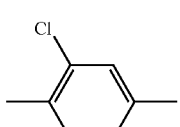 |
| GI(n) | 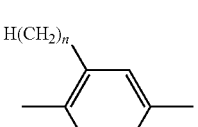 |
| | (n ∈ {1; 2; 3; 4; 5}) |
| UI | 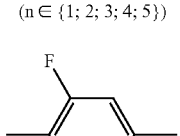 |
| MI | 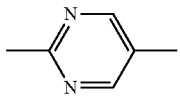 |
| NI | 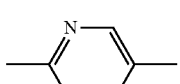 |
| np | 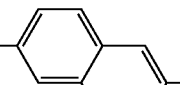 |

TABLE A-continued
| Ring Elements | | |
|---|---|---|
| n3f | 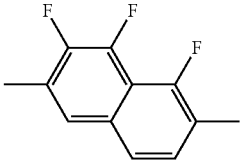 | |
| th | 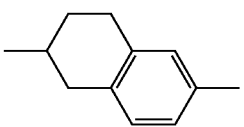 | |
| th2f | 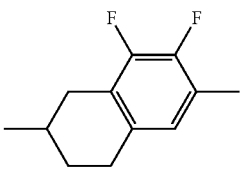 | |
| o2f | 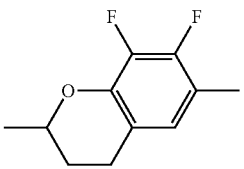 | |
| dh | 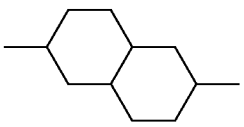 | |
| K | 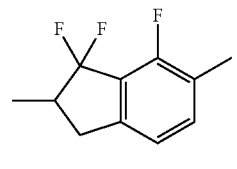 | |
| L | 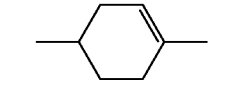 | |
| n3fl | 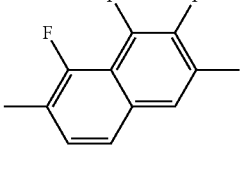 | |
| thl | 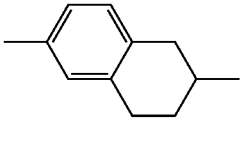 | |
| th2fl | 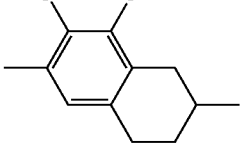 | |
| o2fl | 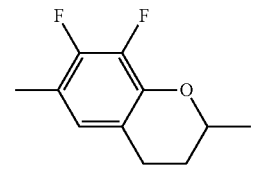 | |
| KI | 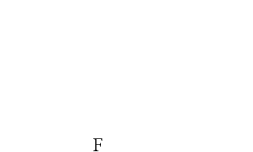 | |
| LI | 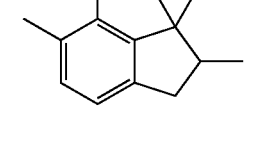 | |
| F | 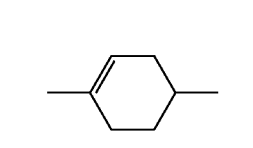 | |
| FI | 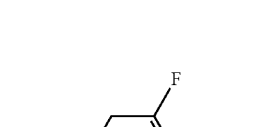 | |
TABLE B
| Linking Groups | | | |
|---|---|---|---|
| n | $(-CH_2-)_n$ | "n" is an integer except 0 and 2 | |
| E | $-CH_2-CH_2-$ | | |
| V | $-CH=CH-$ | | |
| T | $-C\equiv C-$ | | |
| W | $-CF_2-CF_2-$ | | |
| B | $-CF=CF-$ | | |
| Z | $-CO-O-$ | ZI | $-O-CO-$ |
| X | $-CF=CH-$ | XI | $-CH=CF-$ |
| 1O | $-CH_2-O-$ | O1 | $-O-CH_2-$ |
| Q | $-CF_2-O-$ | QI | $-O-CF_2-$ |

TABLE C

End Groups

| Left hand side, used alone or in combination with others | | Right hand side, used alone or in combination with others | |
|---|---|---|---|
| -n- | $C_nH_{2n+1}-$ | -n | $-C_nH_{2n+1}$ |
| -nO- | $C_nH_{2n+1}-O-$ | -nO | $-O-C_nH_{2n+1}$ |
| -V- | $CH_2=CH-$ | -V | $-CH=CH_2$ |
| -nV- | $C_nH_{2n+1}-CH=CH-$ | -nV | $-C_nH_{2n}-CH=CH_2$ |
| -Vn- | $CH_2=CH-C_nH_{2n}-$ | -Vn | $-CH=CH-C_nH_{2n+1}$ |
| -nVm- | $C_nH_{2n+1}-CH=CH-C_mH_{2m}-$ | -nVm | $-C_nH_{2n}-CH=CH-C_mH_{2m+1}$ |
| -N- | $N\equiv C-$ | -N | $-C\equiv N$ |
| -S- | $S=C=N-$ | -S | $-N=C=S$ |
| -F- | $F-$ | -F | $-F$ |
| -CL- | $Cl-$ | -CL | $-Cl$ |
| -M- | $CFH_2-$ | -M | $-CFH_2$ |
| -D- | $CF_2H-$ | -D | $-CF_2H$ |
| -T- | $CF_3-$ | -T | $-CF_3$ |
| -MO- | $CFH_2O-$ | -OM | $-OCFH_2$ |
| -DO- | $CF_2HO-$ | -OD | $-OCF_2H$ |
| -TO- | $CF_3O-$ | -OT | $-OCF_3$ |
| -A- | $H-C\equiv C-$ | -A | $-C\equiv C-H$ |
| -nA- | $C_nH_{2n+1}-C\equiv C-$ | -An | $-C\equiv C-C_nH_{2n+1}$ |
| -NA- | $N\equiv C-C\equiv C-$ | -AN | $-C\equiv C-C\equiv N$ |
| -...n...- | $(-CH_2-)_n$ | -...n... | $(-CH_2-)_n$ |
| -...M...- | $-CFH-$ | -...M... | $-CFH-$ |
| -...D...- | $-CF_2-$ | -...D... | $-CF_2-$ |
| -...V...- | $-CH=CH-$ | -...V... | $-CH=CH-$ |
| -...Z...- | $-CO-O-$ | -...Z... | $-CO-O-$ |
| -...ZI...- | $-O-CO-$ | -...ZI... | $-O-CO-$ |
| -...K...- | $-CO-$ | -...K... | $-CO-$ |
| -...W...- | $-CF=CF-$ | -...W... | $-CF=CF-$ | wherein n und m each are integers and three points "..." indicate a space for other symbols of this table.

Preferably the liquid crystalline media according to the present invention comprise, besides the compound(s) of formula I one or more compounds selected from the group of compounds of the formulae of the following table.

TABLE D

In this table n is an integer selected from 3 and 5 to 15, preferably from 3, 5, 7 and 9, unless explicitly defined otherwise.

Chiral dopants

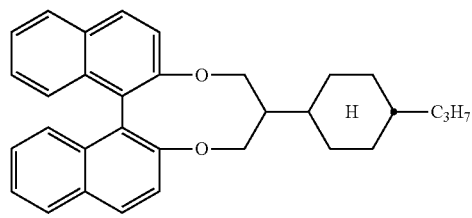

R-5011 respectively S-5011

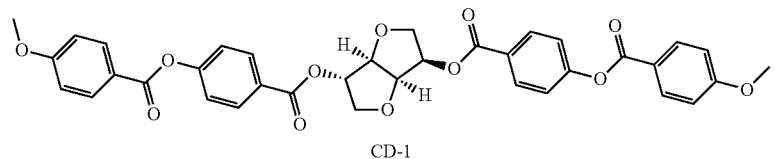

CD-1

Nematic or nematogenic compounds

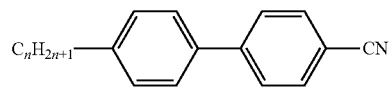

PP-n-N (n ∈ {2; 3; 4; 5; 6; 7})

TABLE D-continued
In this table n is an integer selected from 3 and 5 to 15, preferably from 3, 5, 7 and 9, unless explicitly defined otherwise.
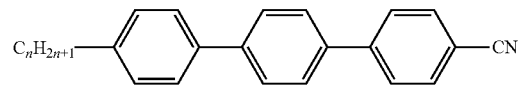
PPP-n-N (n ∈ {2; 3; 4; 5; 6; 7})
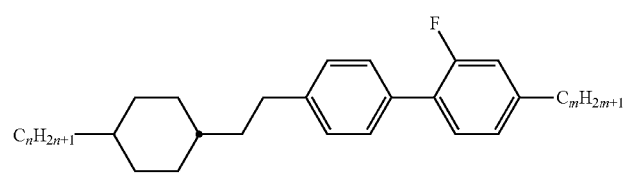
CC-n-V (n ∈ {2; 3; 4; 5; 7})
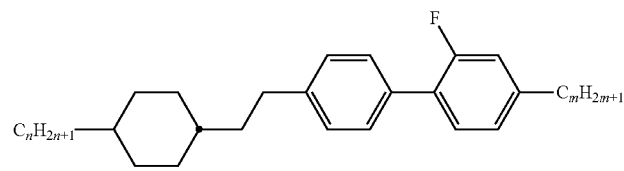
CEPGI-n-m (n ∈ {2; 3; 4; 5}; m ∈ {2; 3; 4; 5})
Bimesogenic compounds
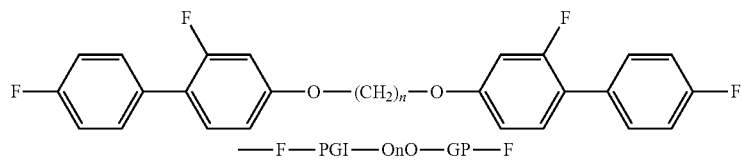
F—PGI—OnO—GP—F
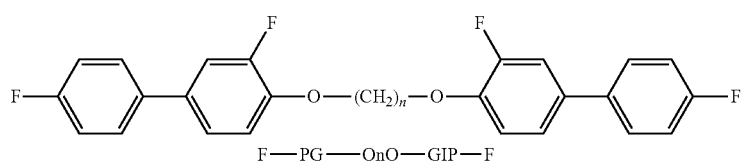
F—PG—OnO—GIP—F
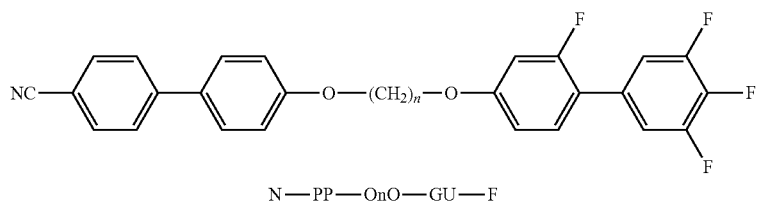
N—PP—OnO—GU—F
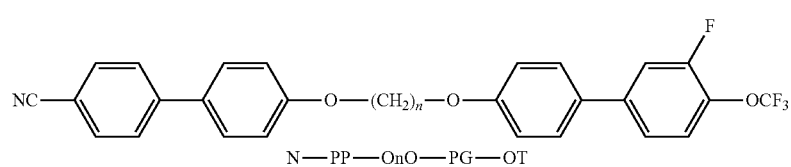
N—PP—OnO—PG—OT
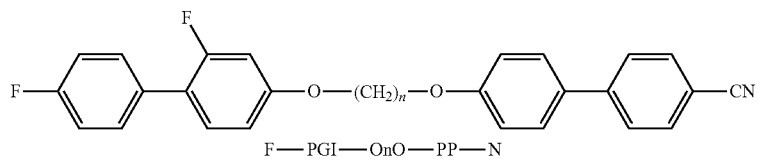
F—PGI—OnO—PP—N TABLE D-continued
In this table n is an integer selected from 3 and 5 to 15, preferably from 3, 5, 7 and 9, unless explicitly defined otherwise.
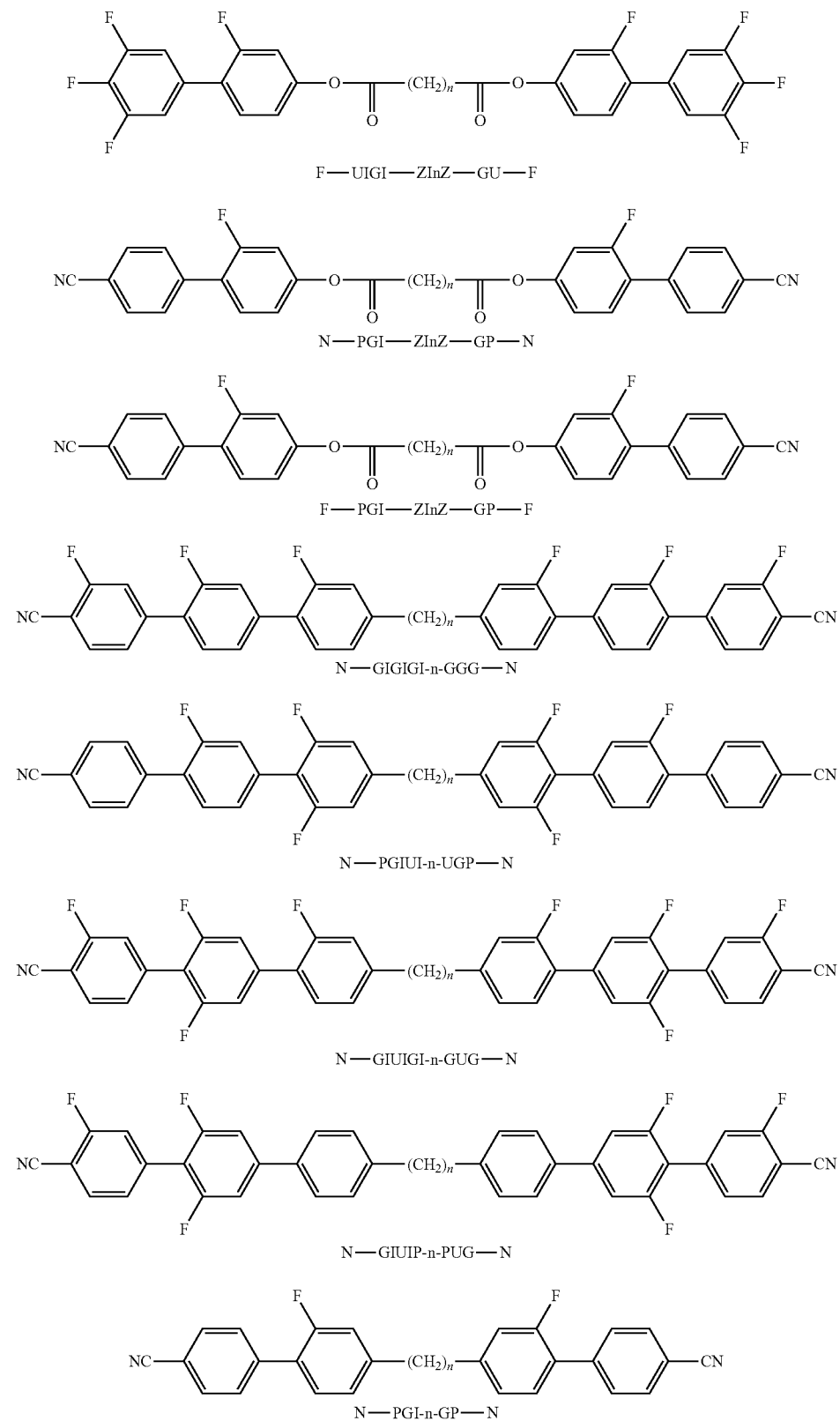

US 9,644,144 B2
TABLE D-continued
In this table n is an integer selected from 3 and 5 to 15, preferably from 3, 5, 7 and 9, unless explicitly defined otherwise.
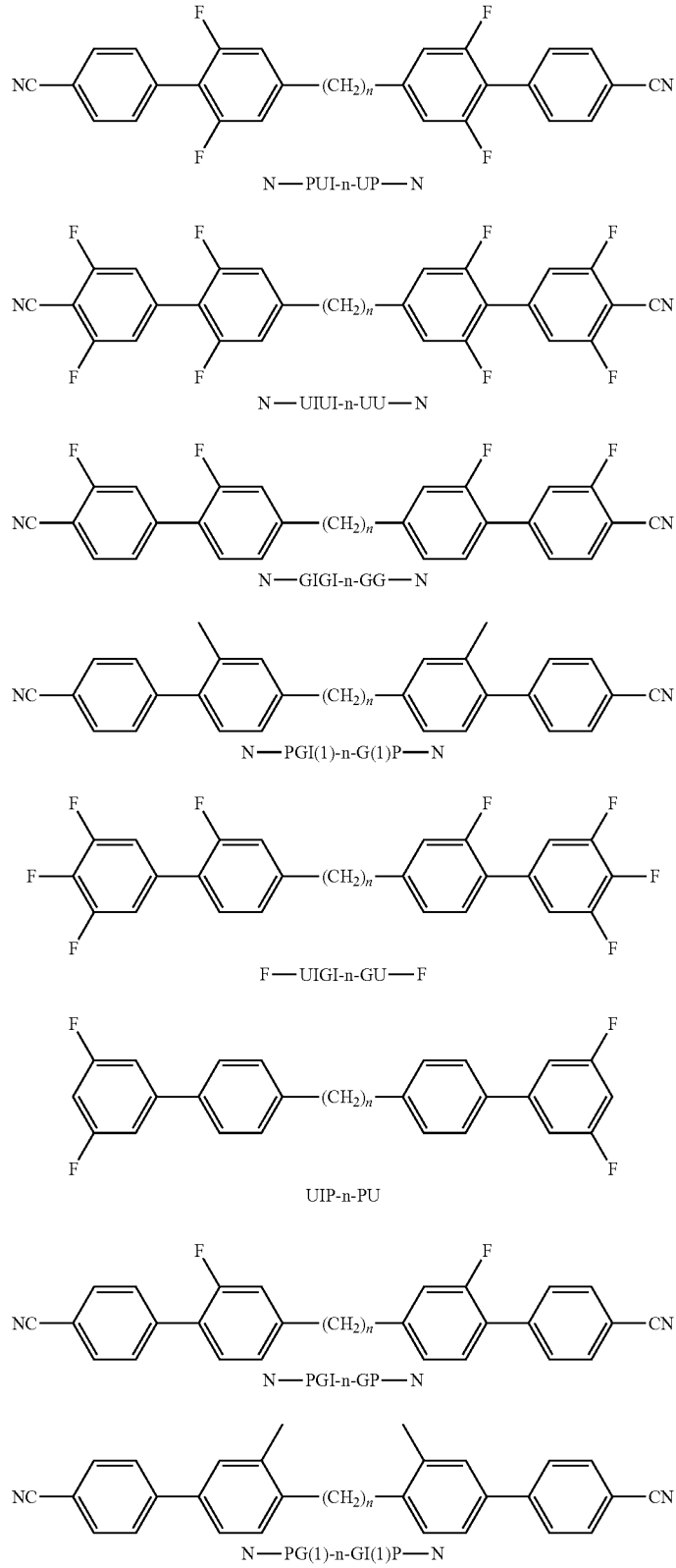

TABLE D-continued
In this table n is an integer selected from 3 and 5 to 15, preferably from 3, 5, 7 and 9, unless explicitly defined otherwise.
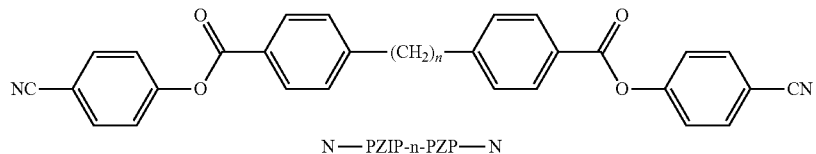
N—PZIP-n-PZP—N
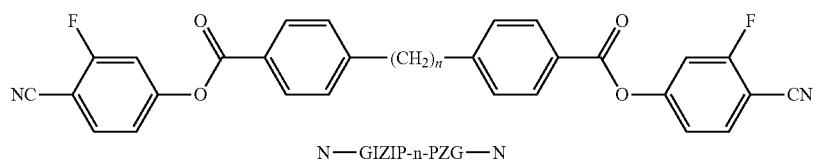
N—GIZIP-n-PZG—N
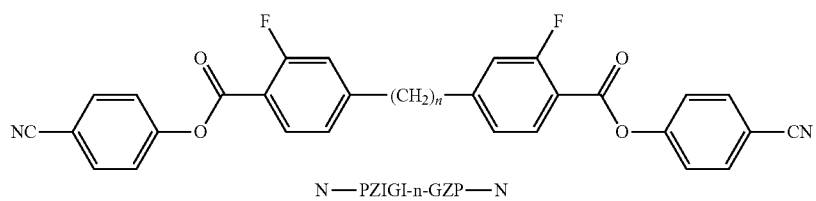
N—PZIGI-n-GZP—N
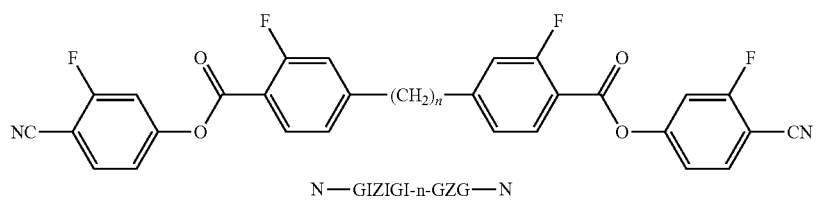
N—GIZIGI-n-GZG—N
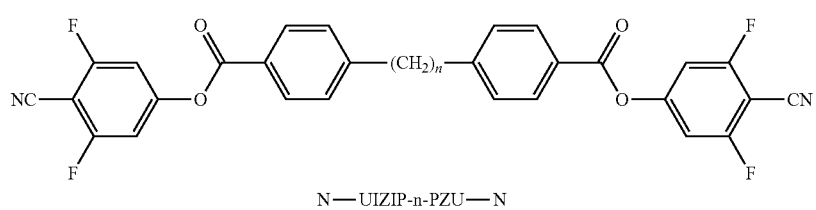
N—UIZIP-n-PZU—N
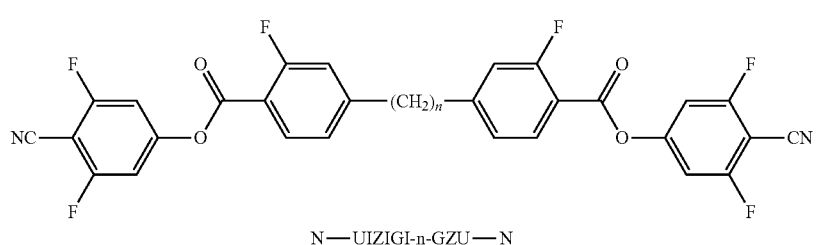
N—UIZIGI-n-GZU—N
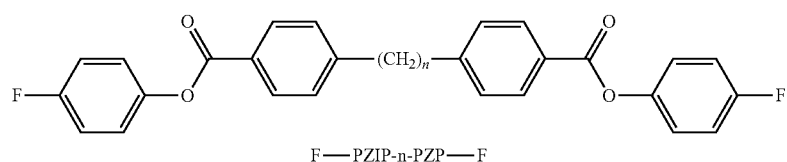
F—PZIP-n-PZP—F
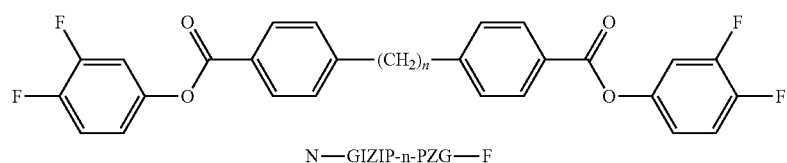
N—GIZIP-n-PZG—F TABLE D-continued
In this table n is an integer selected from 3 and 5 to 15, preferably from 3, 5, 7 and 9, unless explicitly defined otherwise.
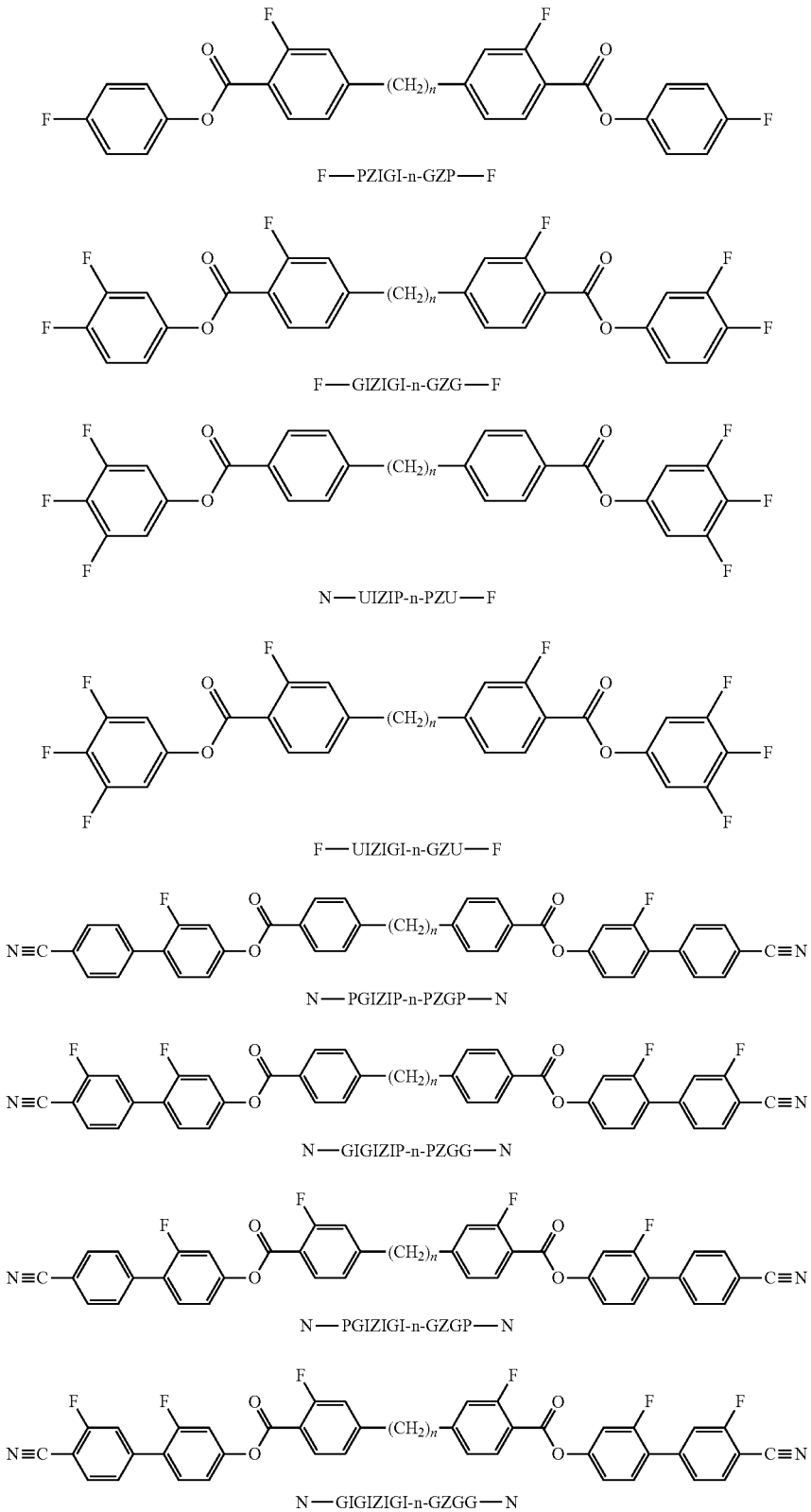

TABLE D-continued
In this table n is an integer selected from 3 and 5 to 15, preferably from 3, 5, 7 and 9, unless explicitly defined otherwise.
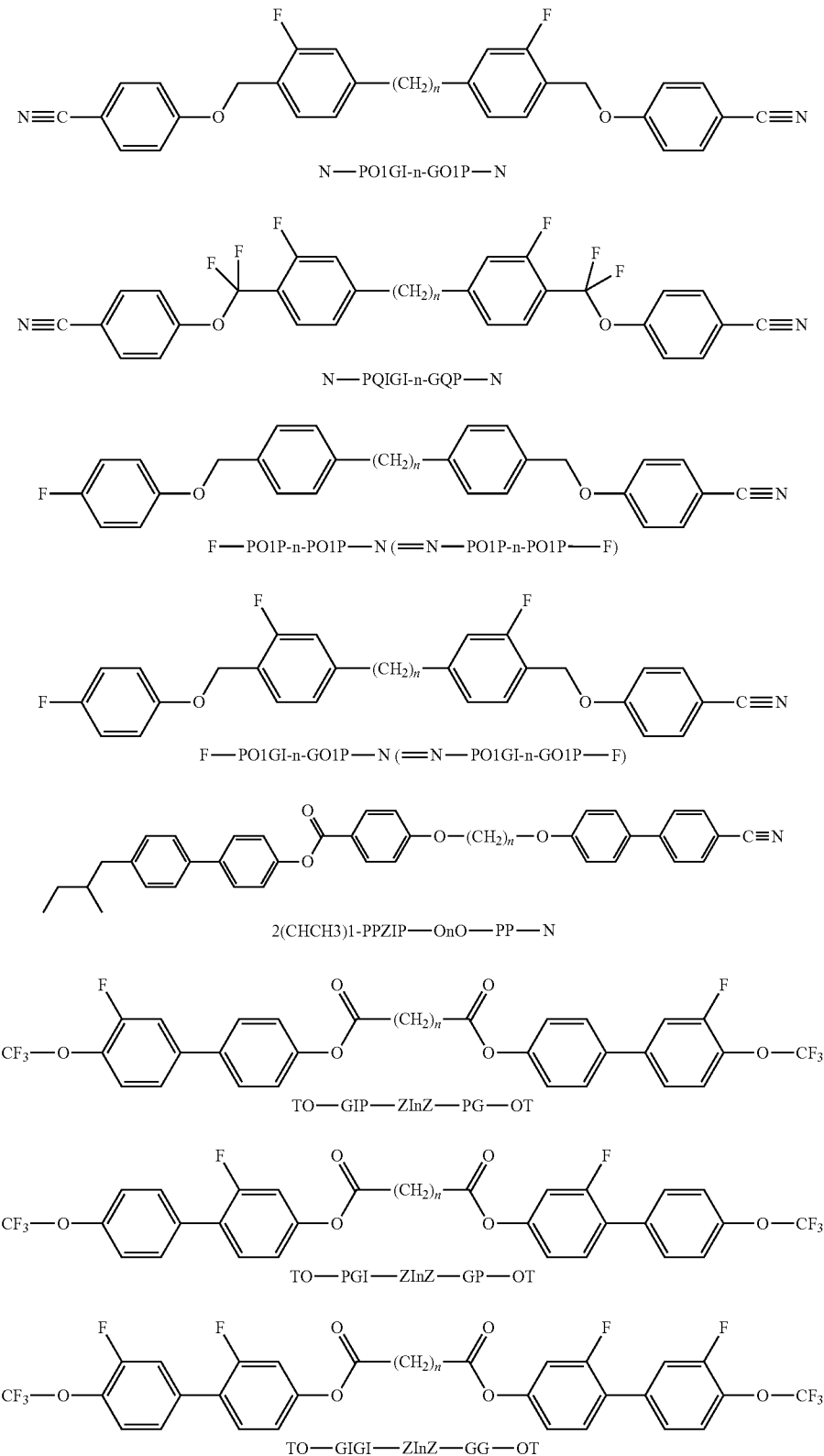

TABLE D-continued
In this table n is an integer selected from 3 and 5 to 15, preferably from 3, 5, 7 and 9, unless explicitly defined otherwise.
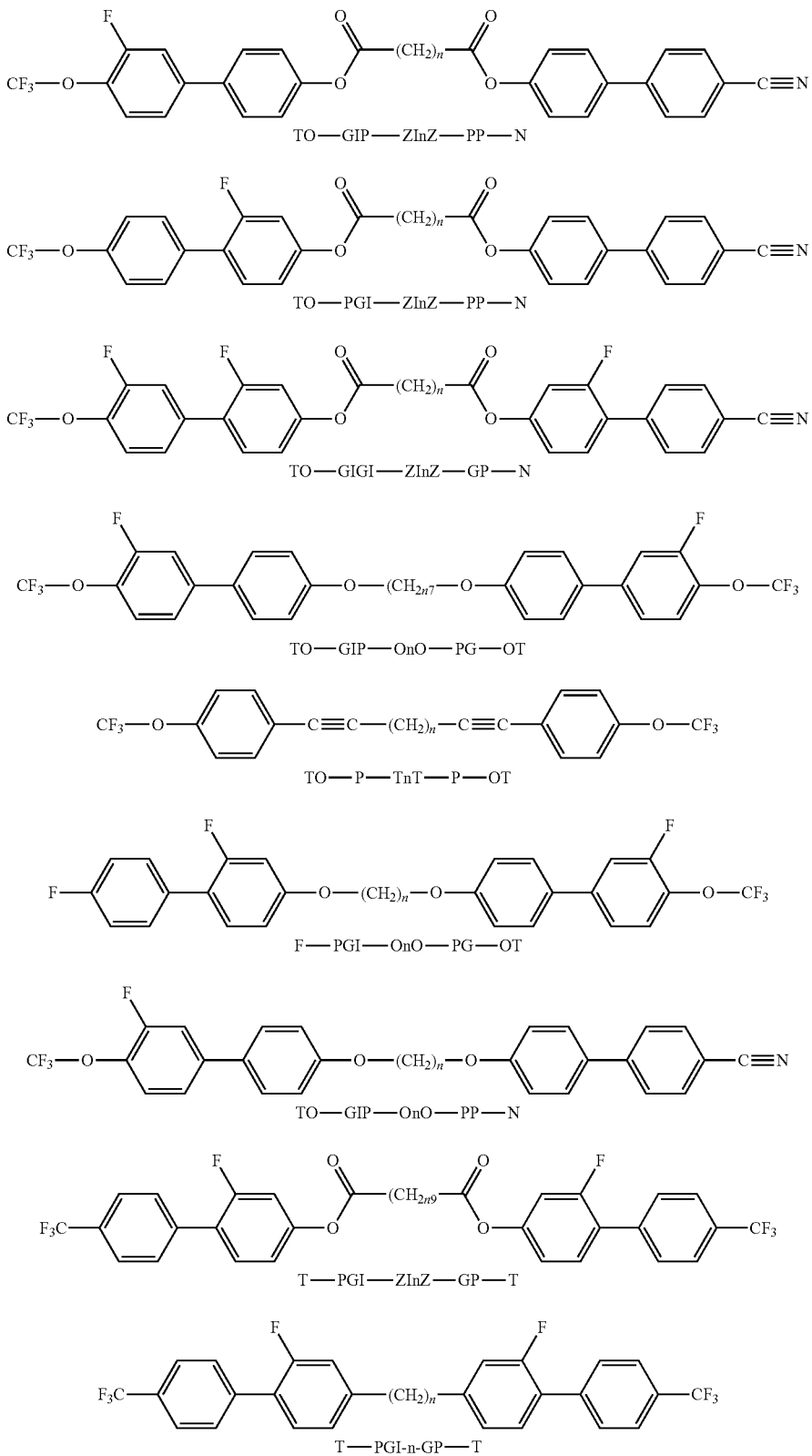

TABLE D-continued
In this table n is an integer selected from 3 and 5 to 15, preferably from 3, 5, 7 and 9, unless explicitly defined otherwise.
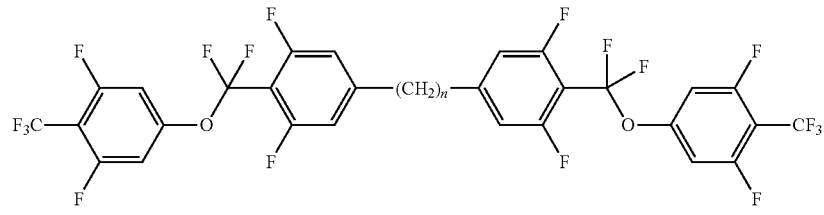
T—UIQIUI-n-UQU—T
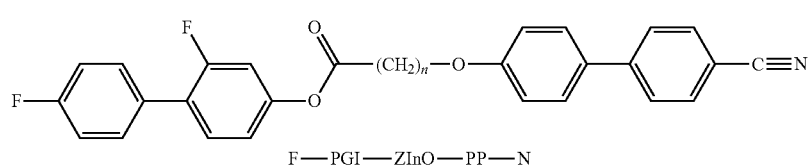
F—PGI—ZInO—PP—N
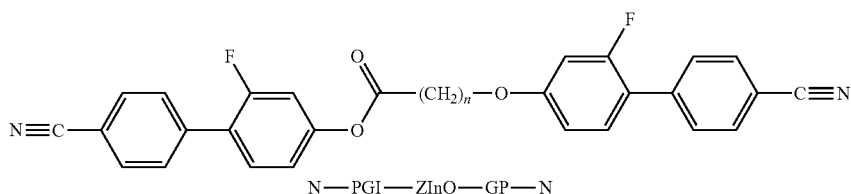
N—PGI—ZInO—GP—N
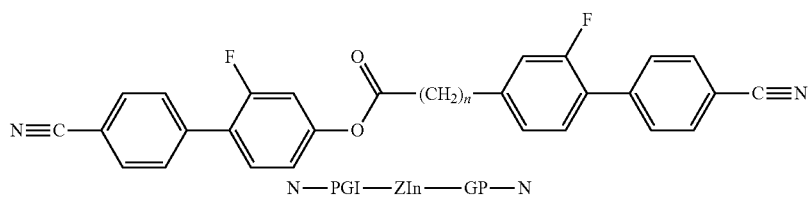
N—PGI—ZIn—GP—N
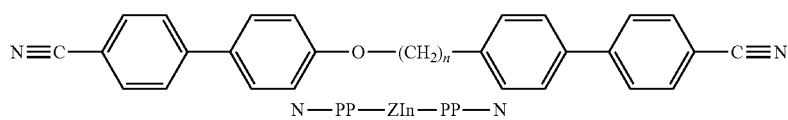
N—PP—ZIn—PP—N
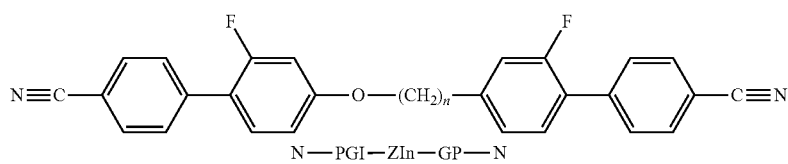
N—PGI—ZIn—GP—N
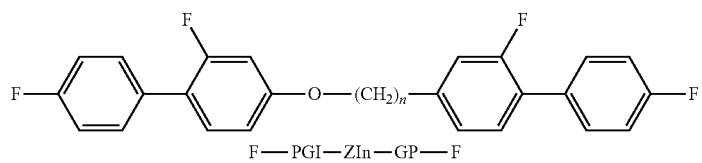
F—PGI—ZIn—GP—F
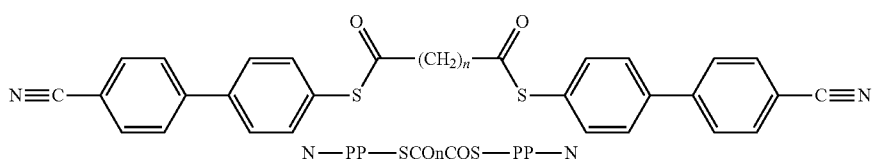
N—PP—SCOnCOS—PP—N TABLE D-continued
In this table n is an integer selected from 3 and 5 to 15, preferably from 3, 5, 7 and 9, unless explicitly defined otherwise.
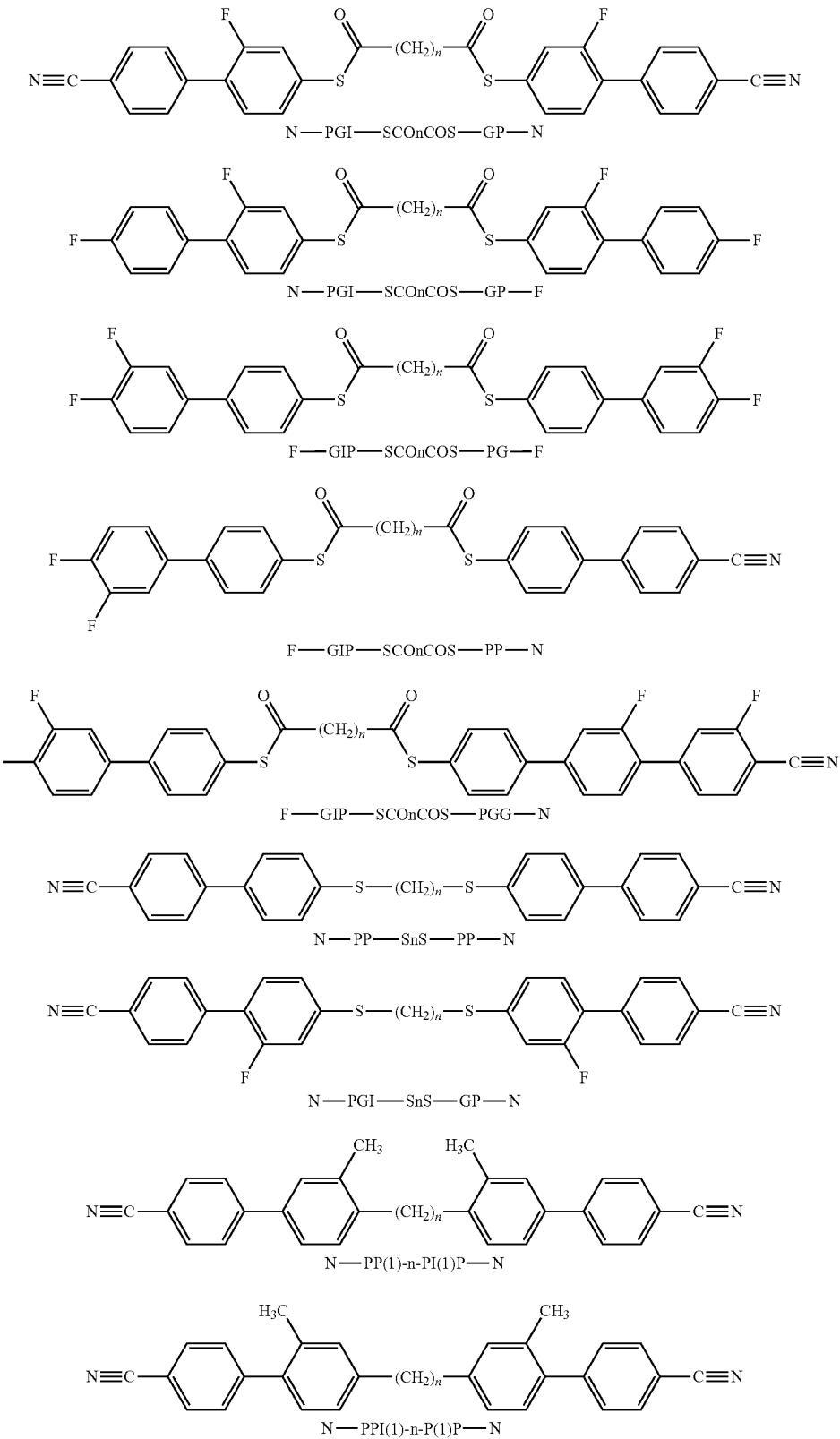

TABLE D-continued
In this table n is an integer selected from 3 and 5 to 15, preferably from 3, 5, 7 and 9, unless explicitly defined otherwise.
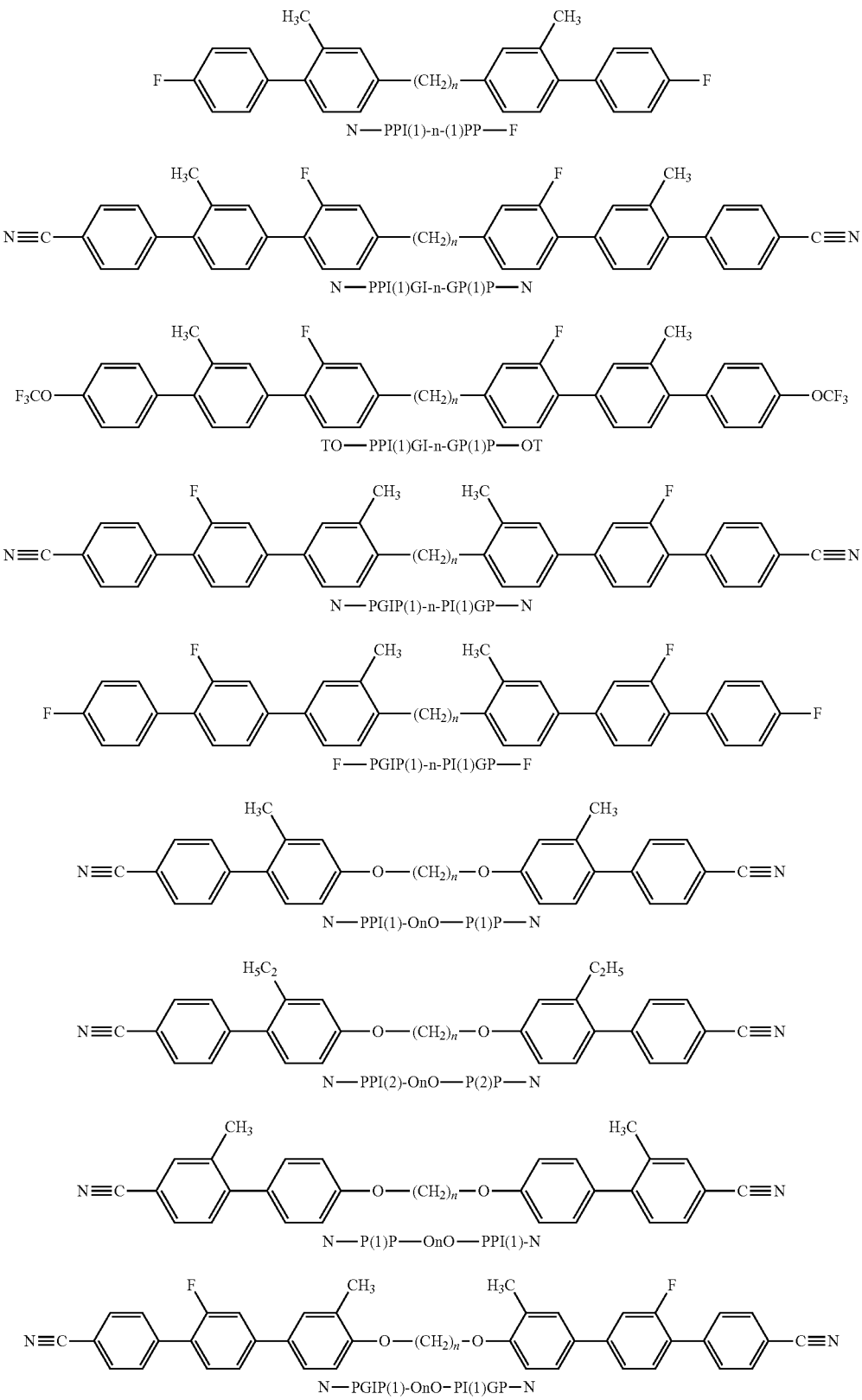

TABLE D-continued
In this table n is an integer selected from 3 and 5 to 15, preferably from 3, 5, 7 and 9, unless explicitly defined otherwise.
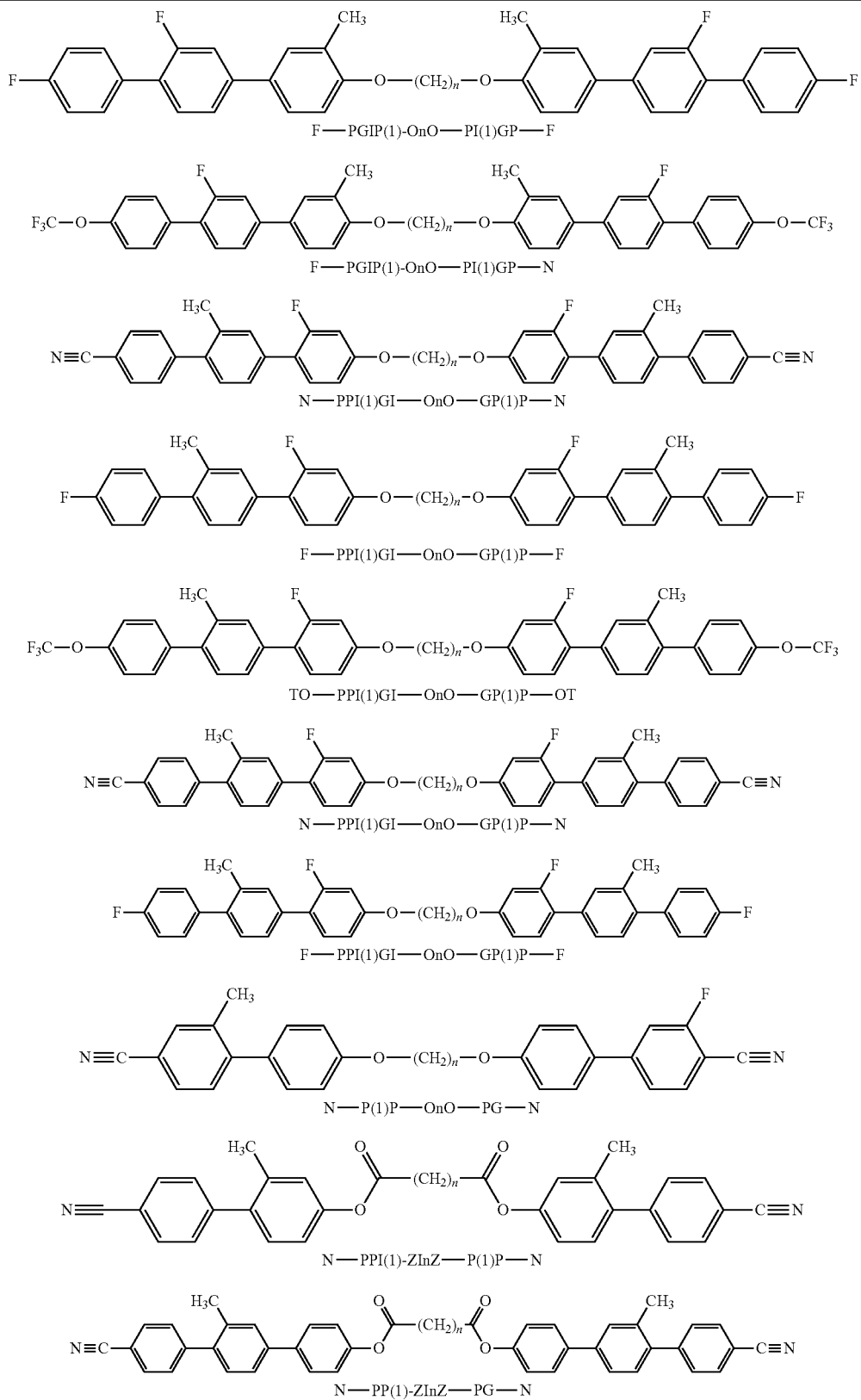

TABLE D-continued
In this table n is an integer selected from 3 and 5 to 15, preferably from 3, 5, 7 and 9, unless explicitly defined otherwise.
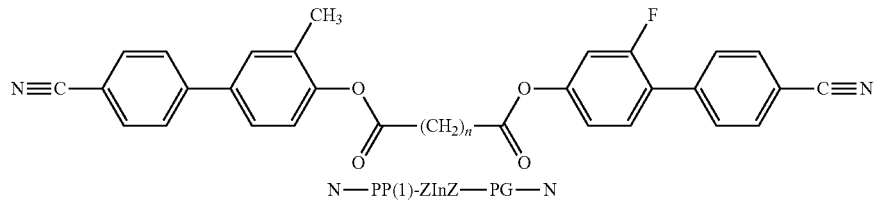
N—PP(1)-ZInZ—PG—N
COMPOUND AND SYNTHESIS EXAMPLES
Synthesis Example 1
Preparation of N—PPI(1)-O9O—P(1)P—N
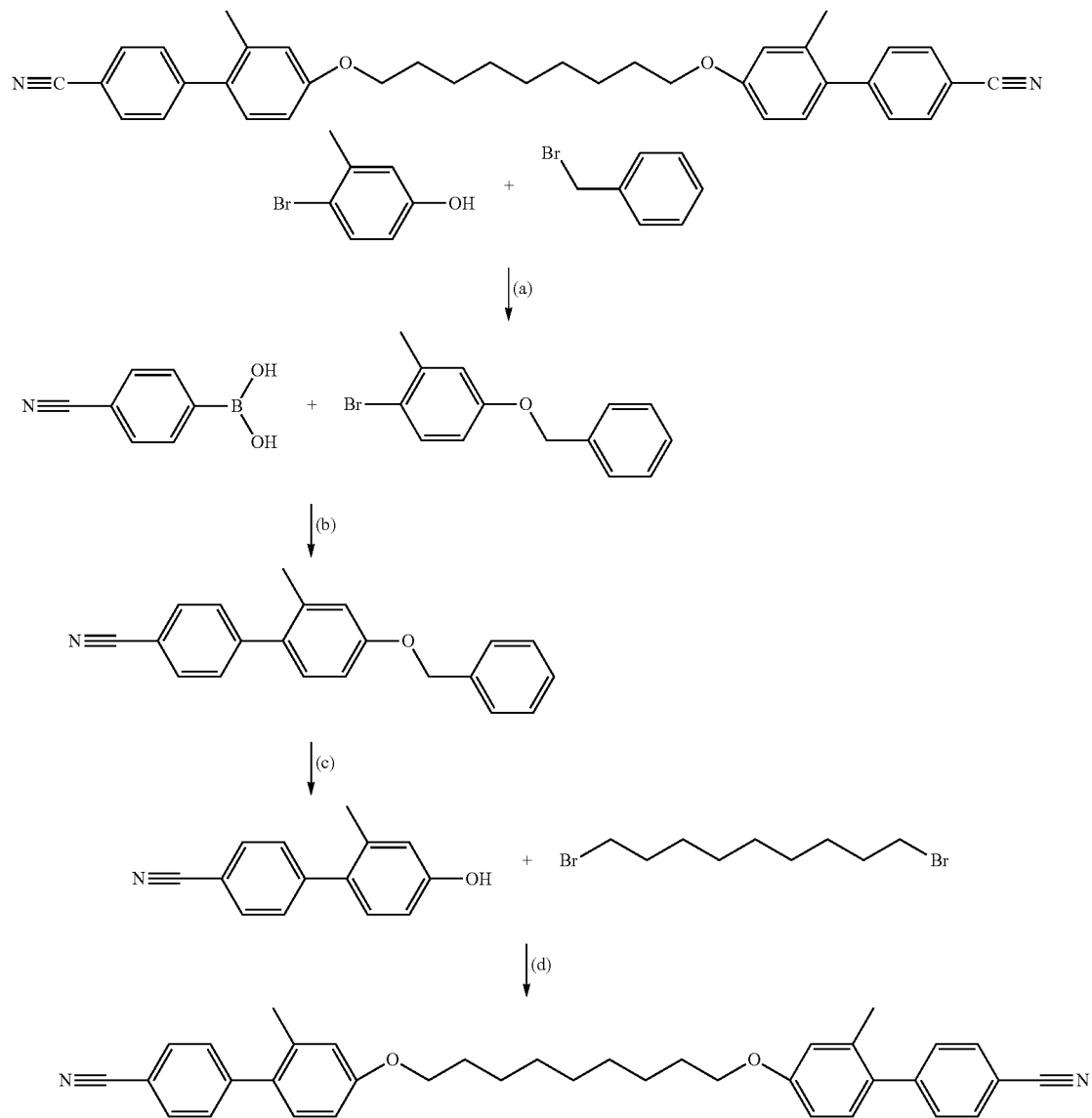

Step 1.1

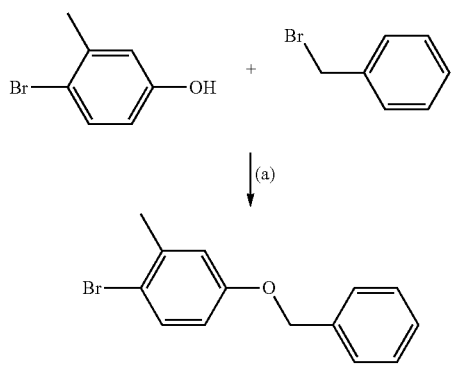

Conditions for the reaction: (a) K$_2$CO$_3$, MEK, 80° C. 18 h.

3-methy-4-bromophenol (100 g, 535 mmol) is added into a round bottom flask along with benzylbromide (63.5 ml, 535 mmol), potassium carbonate (81.3 g, 588 mmol) and methyl ethylketone (700 ml). The mixture is stirred under a nitrogen atmosphere before being heated to reflux for 18 hours. The reaction mixture is then cooled, the solids removed by filtration in vacuo, and the filter pad washed well with methyl ethylketone. The filtrate is diluted with water before being extracted by ethyl acetate. The organic phases are washed with brine, dried over magnesium sulphate and concentrated to yield the crude product. Purification is carried out by two successive re-crystallisations from IMS to yield a pure white solid.

Step 1.2

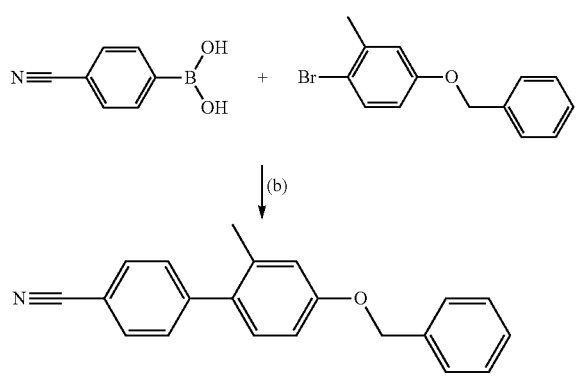

Conditions for the reaction: (b) PdCl$_2$(PPh$_3$)$_2$, NaBO$_2$, THF, H$_2$O, 80° C., 24 h.

The product from the previous step, step 1.1, (37.7 g, 136 mmol) sas added into a flask along with 4-cyanobenzeneboronic acid (20.0 g, 136 mmol), sodium metaborate octahydrate (56.3 g, 204 mmol), tetrahydrofuran (500 ml) and water (50 ml). The mixture is placed under a nitrogen atmosphere before adding Palladium(triphenylphosphine)dichloride (2.38 g, 3.4 mmol) and heating under reflux for 16 hours. The reaction mixture is cooled, diluted with water and extracted with ethyl acetate. The organic phase is washed with dilute HCl and then water until neutral, followed by drying over magnesium sulphate and concentration in vacuo. The crude solid product is purified by column chromatography through silica gel and eluted with a mixture of dichloromethane and petroleum ether (ratio 2:5).

Step 1.3

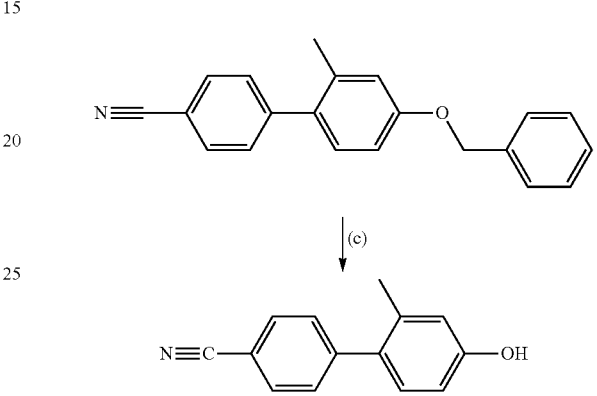

Conditions for the reaction: (c) BBr$_3$, DCM, −70° C.

The product from the previous step, step 1.2, (17.0 g, 56.8 mmol) is added into a reaction flask with dichloromethane (450 ml) and is then cooled to a temperature of −70° C. under a nitrogen atmosphere. A 1 Molar solution of borontribromide in dichloromethane (114 ml, 114 mmol) is then added slowly, keeping the temperature of the reaction mixture always at −70° C. Upon complete addition the reaction mixture is stirred for a further 3 hours at −70° C. until the reaction has completed. After warming to −40° C. a saturated solution of sodium hydrogen carbonate (250 ml) is added and the resultant mixture is stir and allowed to stir at room temperature for a further 1 hour. Water is slowly added to the reaction, and the layers are separated. The aqueous material is extracted with dichloromethane three times and the combined organic material is then washed well with water. After drying over magnesium sulphate, the organic material is concentrated to yield the product, purified by slurrying with hot petroleum ether and isolating the solid in vacuo, which is purified further by column chromatography through silica gel, eluting with a mixture of dichloromethane and petroleum ether.

Step 1.4

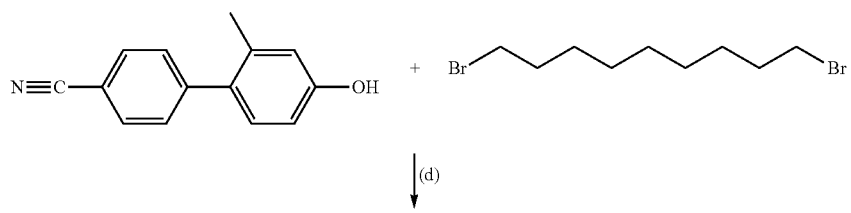

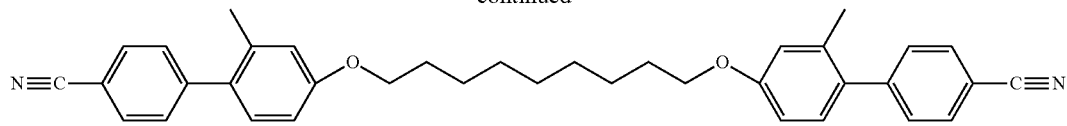

Conditions for the reaction: (d) K$_2$CO$_3$, MEK, 80° C. 18 h.

The product from the previous step, step, 1.3 (10.0 g, 47.8 mmol) is added into a flask together with 1,9-dibromononane (6.8 g, 23.9 mmol), potassium carbonate (8.3 g, 59.8 mmol) and methyl ethylketone (150 ml). The mixture is stirred under a nitrogen atmosphere and heated under reflux for 18 hours. The reaction mixture is then cooled and filtered in vacuo, the filter pad is washed well with methyl ethylketone before the filtrates are concentrated to yield the crude, solid product. This is purified by column chromatography through silica gel, eluting with a mixture of dichloromethane and petroleum ether. A second chromatography column of silica gel is required to obtain the pure product.

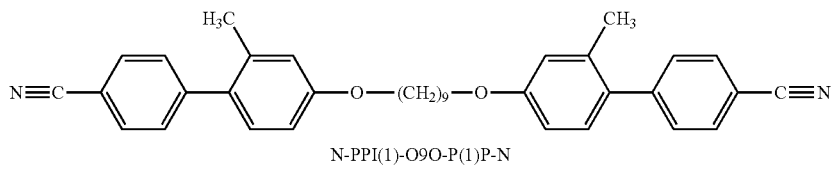

N-PPI(1)-O9O-P(1)P-N

Phase sequence: K 56 I; T*(N,I)=74.0° C.; e/K=1.83 V$^{-1}$. (Remark: T*(N,I) and e/K extrapolated from 10% in host mixture H-0 with 2% of R-5011.)

Synthesis Example 2

Preparation of N—P(1)P—O9O—PG-N

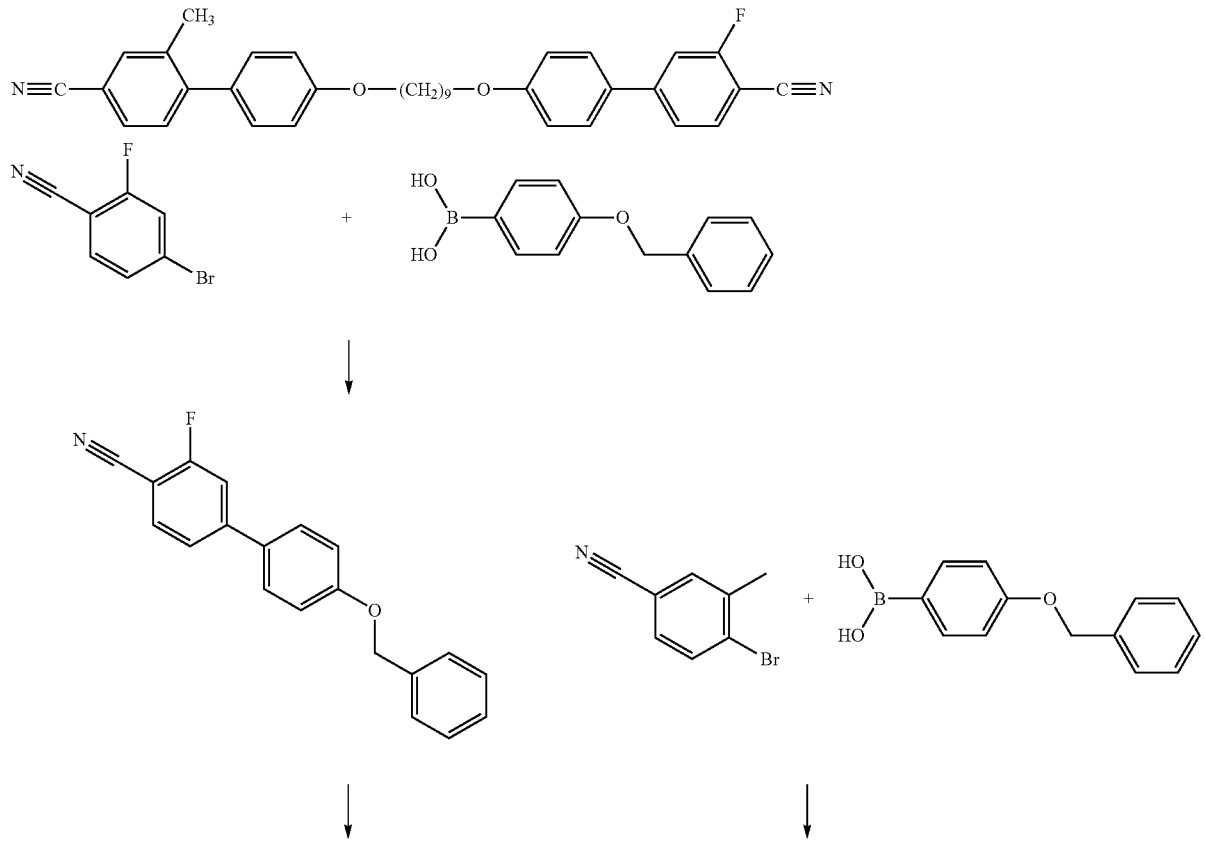

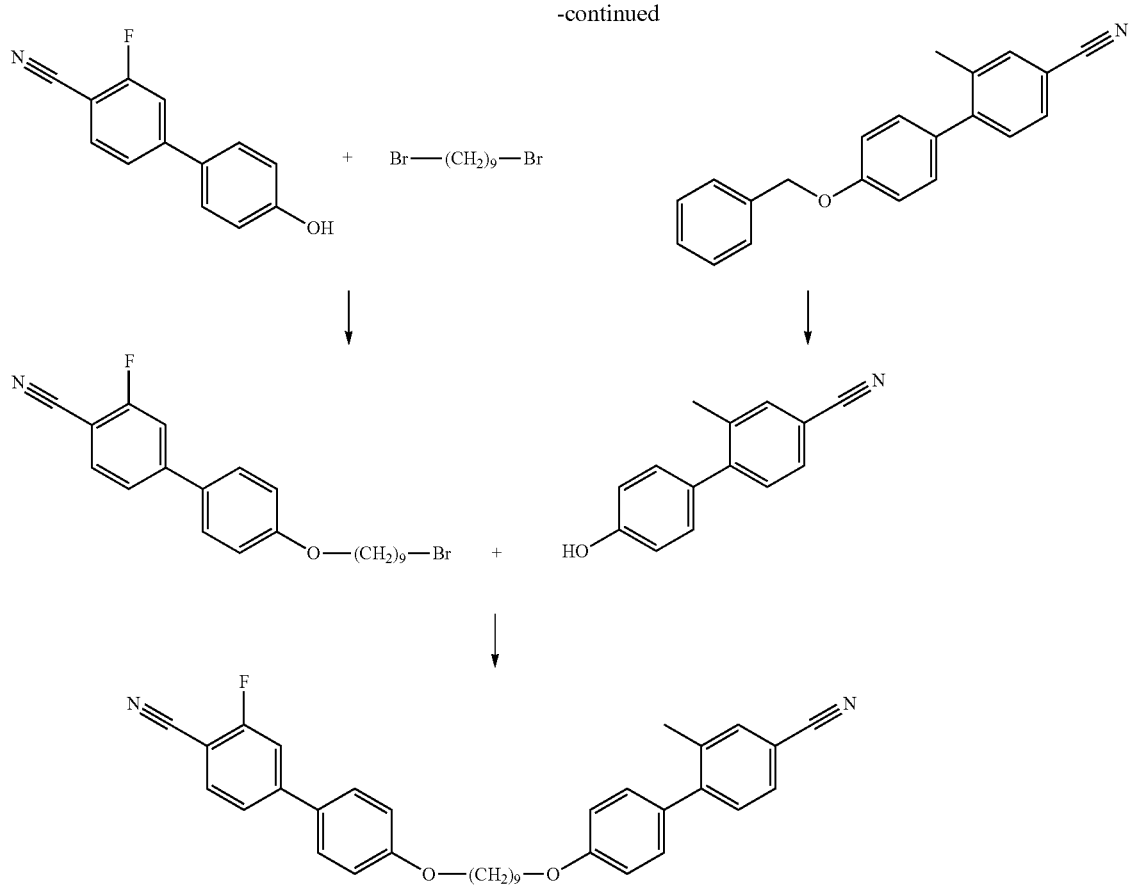

Step 2.1

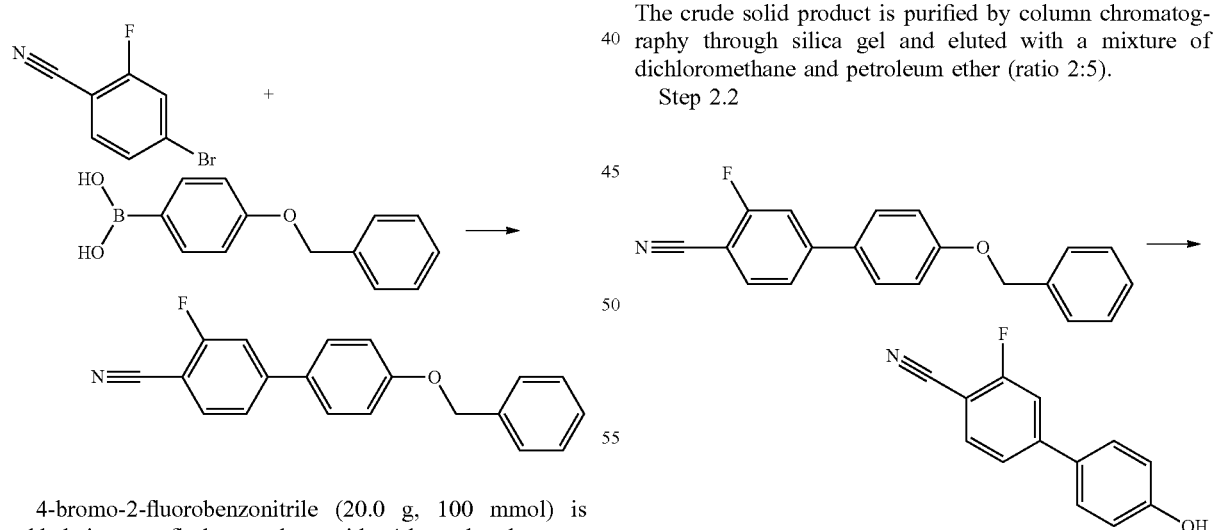

4-bromo-2-fluorobenzonitrile (20.0 g, 100 mmol) is added into a flask together with 4-benzyloxybenzene boronic acid (22.8 g, 100 mmol), sodium metaborate octahydrate (41.4 g, 150 mmol), water (40 ml), tetrahydrofuran (500 ml) and palladium(triphenylphosphine)-dichloride (1.75 g, 2.5 mmol). The reaction mixture is heated for 16 h under a nitrogen atmosphere under reflux. After cooling to ambient temperature, which in this application means a temperature of approximately 20° C., the reaction is diluted with water and the layers are separated. The aqueous layer is extracted twice with ethyl acetate. The organic material is combined, washed with water then dried and concentrated. The crude solid product is purified by column chromatography through silica gel and eluted with a mixture of dichloromethane and petroleum ether (ratio 2:5).

Step 2.2

The product from the previous step, step 2.1 (21.2 g, 69.7 mmol) is added into a reaction flask with dichloromethane (450 ml) and is then cooled to a temperature of −70° C. under a nitrogen atmosphere. A 1 Molar solution of borontribromide in dichloromethane (139 ml, 139 mmol) is then added slowly, keeping the temperature of the reaction mixture always at −70° C. Upon complete addition the reaction mixture is stirred for a further 3 hours at −70° C. until the reaction has completed. After warming to −40° C. a saturated solution of sodium hydrogen carbonate (250 ml) is added and the resultant mixture is stir and allowed to slowly warm up to room temperature. The layers are separated, the organic material is washed well with water and subsequently the aqueous material extracted with dichloromethane. After drying over magnesium sulphate the organic material is concentrated to yield the product, which is purified by column chromatography through silica gel, eluting with a mixture of dichloromethane and petroleum ether (ratio 1:4).

Step 2.3

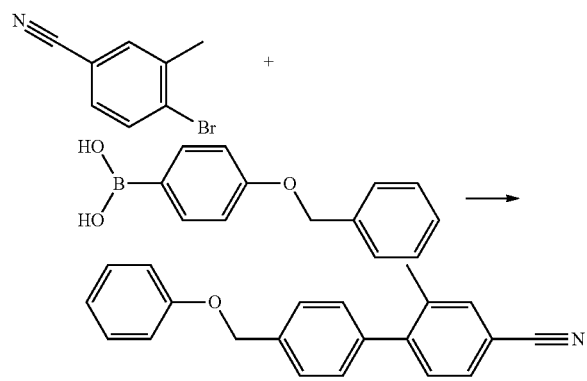

4-bromo-3-methylbenzonitrile (20.0 g, 102 mmol) is added into a flask together with 4-benzyloxybenzene boronic acid (23.3 g, 102 mmol), sodium metaborate octahydrate (42.2 g, 153 mmol), water (40 ml), tetrahydrofuran (500 ml) and palladium(triphenylphosphine)-dichloride (1.79 g, 2.5 mmol). The reaction mixture is heated for 16 h under a nitrogen atmosphere under reflux. After cooling to ambient temperature the reaction mixture is diluted with water and the layers are separated. The aqueous layer is extracted twice with ethyl acetate, the organic material is combined, washed with water then dried and concentrated. The crude solid product is purified by column chromatography through silica gel, eluting with a mixture of dichloromethane and petroleum ether (ratio 2:5).

Step 2.4

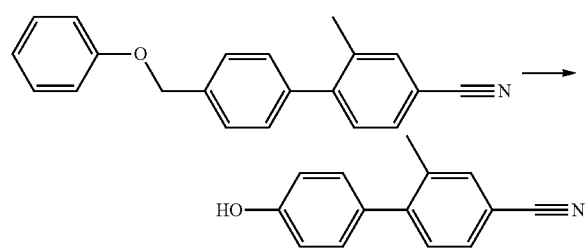

The product from the previous step, step 2.3 (20.0 g, 66.8 mmol) is added into a reaction flask together with dichloromethane (450 ml) and then cooled to −70° C. under a nitrogen atmosphere. A 1 Molar solution of borontribromide in dichloromethane (134 ml, 134 mmol) is added slowly, keeping the temperature of the reaction mixture always at −70° C. Upon complete addition the reaction mixture is stirred for a further 3 hours at −70° C. until the reaction is completed. After warming to −40° C. a saturated solution of sodium hydrogen carbonate (250 ml) is added and the resultant mixture is stirred and left to slowly warm to ambient temperature. The layers are separated, the organic material is washed well with water and subsequently the aqueous material is extracted with dichloromethane. After drying over magnesium sulphate the organic material is concentrated to yield the crude product, which is purified by column chromatography through silica gel, eluting with a mixture of Dichloromethane/petroleum ether (ratio 1:4).

Step 2.5

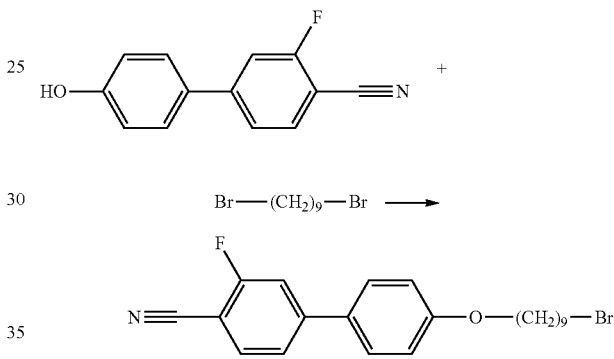

The intermediate product from step 2.2 (10.0 g, 46.9 mmol) is dissolved in acetone (200 ml) in a round bottom flask. Potassium carbonate (13.6 g, 98.5 mmol) is added and the mixture is stirred well and then heated to a gentle reflux for 1 hour. After cooling to room temperature, dibromononane (68.6 ml, 337 mmol) is added along with a small amount of acetone (50 ml) and then the reaction n mixture is again reheated under reflux, this time for 16 h. After cooling (to ambient temperature, the reaction mixture is filtered and the filter pad is washed first with acetone and then with dichloromethane. The filtrate is concentrated to yield a yellow oil, which is further purified by column chromatography through silica gel, eluting with a mixture of dichloromethane and petroleum ether, slowly increasing the amount of dichloromethane to collect the product.

Step 2.6

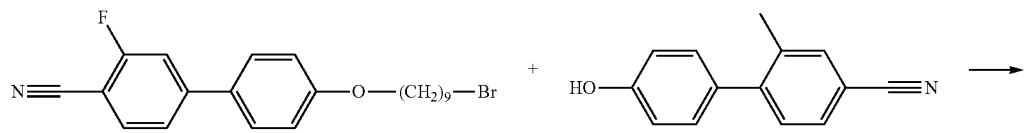

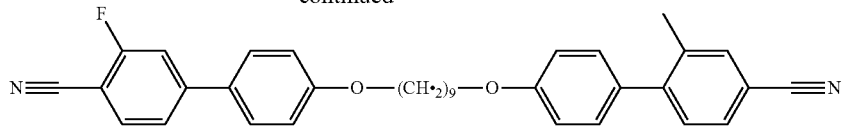

The intermediate product from the previous step, step 2.5, (11.4 g, 27.2 mmol) is charged into a reaction flask together with the intermediate product from step 2.4 (5.70 g, 27.2 mmol). Potassium carbonate (6.0 g, 43.6 mmol) and butanone (250 ml) are also added and the reaction mixture is heated under reflux for 16 h. The reaction mixture is cooled to ambient temperature and filtered. The filter pad is washed with butanone and the filtrate concentrated. The crude solid product is purified by column chromatography through silica gel, eluting with a mixture of dichloromethane and petroleum ether (ratio 2:5) and then it is re-crystallised from a mixture of acetonitrile and IMS (industrial methylated spirits) to yield the desired product.

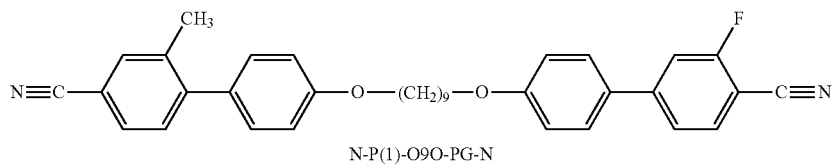

N-P(1)-O9O-PG-N

Phase sequence: K 97.6 I; T*(N,I)=81.9° C.; e/K=1.76 $V^{-1}$. (Remark: T*(N,I) and e/K extrapolated from 10% in host mixture H-0 with 2% of R-5011.)

Phase sequence: K 97 I; T*(N,I)=78.6° C.; e/K=1.87 $V^{-1}$. (Remark: T*(N,I) and e/K extrapolated from 10% in host mixture H-0 with 2% of R-5011.)

Compound Examples 3 and Following

The following compounds of formula I are prepared analogously.

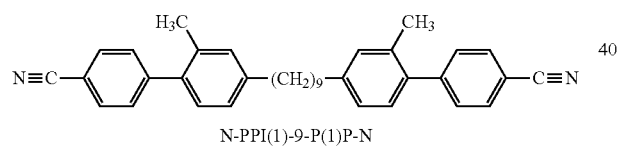

N-PPI(1)-9-P(1)P-N

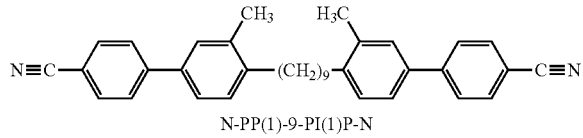

N-PP(1)-9-PI(1)P-N

Phase sequence: K 98.8 I; T*(N,I)=70.8° C.; e/K=2.28 $V^{-1}$. (Remark: T*(N,I) and e/K extrapolated from 10% in host mixture H-0 with 2% of R-5011.)

Phase sequence: K 118 I; T*(N,I)=75.2° C.; e/K=2.25 $V^{-1}$. (Remark: T*(N,I) and e/K extrapolated from 10% in host mixture H-0 with 2% of R-5011.)

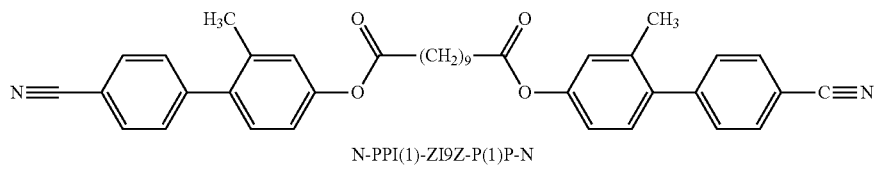

N-PPI(1)-ZI9Z-P(1)P-N

Phase sequence: K 128.4 I; T*(N,I)=77.9° C.; e/K=2.17 $V^{-1}$. (Remark: T*(N,I) and e/K extrapolated from 10% in host mixture H-0 with 2% of R-5011.)

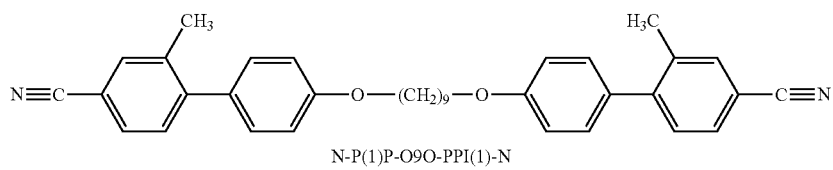

N-P(1)P-O9O-PPI(1)-N

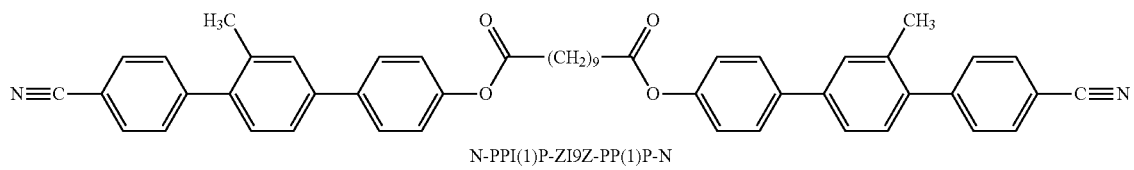
N-PPI(1)P-ZI9Z-PP(1)P-N

Phase sequence: K 148 N 161 I; T*(N,I)=89.0° C.; e/K=1.94 V$^{-1}$. (Remark: T*(N,I) and e/K extrapolated from 10% in host mixture H-0 with 2% of R-5011.)

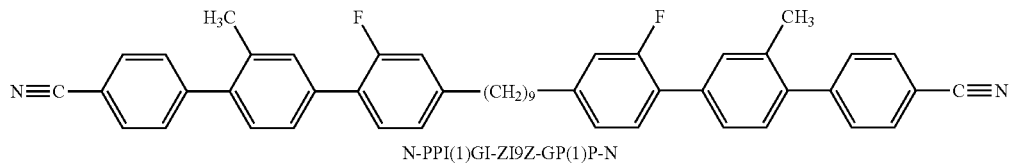
N-PPI(1)GI-ZI9Z-GP(1)P-N

Phase sequence: K 142 N 156 I; T*(N,I)=85.0° C.; e/K=2.24 V$^{-1}$. (Remark: T*(N,I) and e/K extrapolated from 10% in host mixture H-0 with 2% of R-5011.)

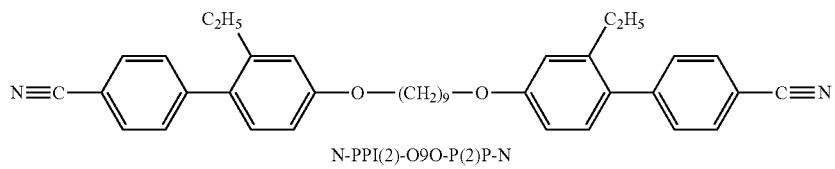
N-PPI(2)-O9O-P(2)P-N

Phase sequence: K 105 I; T*(N,I)=73.0° C.; e/K=2.07 V$^{-1}$. (Remark: T*(N,I) and e/K extrapolated from 10% in host mixture H-0 with 2% of R-5011.)

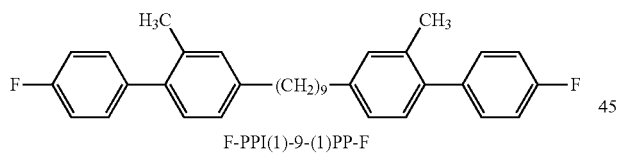
F-PPI(1)-9-(1)PP-F

Phase sequence: K 47.6 X52 I; T*(N,I)=76.0° C.; e/K=1.97 V$^{-1}$. (Remarks: "X" non-identified phase and T*(N,I) and e/K extrapolated from 10% in host mixture H-0 with 2% of R-5011.)

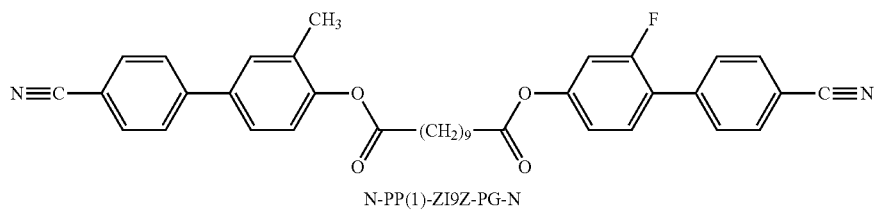
N-PP(1)-ZI9Z-PG-N

Phase sequence: K 111 N 120 I; T*(N,I)=84.0° C.; e/K=2.02 V$^{-1}$. (Remark: T*(N,I) and e/K extrapolated from 10% in host mixture H-0 with 2% of R-5011.)

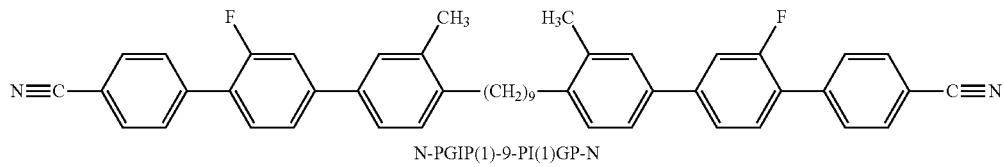

N-PGIP(1)-9-PI(1)GP-N

Phase sequence: K 100.8 S 107 N 179 I; T*(N,I)=88.6° C.; e/K=2.14 V$^{-1}$. (Remarks: "S" non-identified smectic phase and T*(N,I) and e/K extrapolated from 10% in host mixture H-0 with 2% of R-5011.)

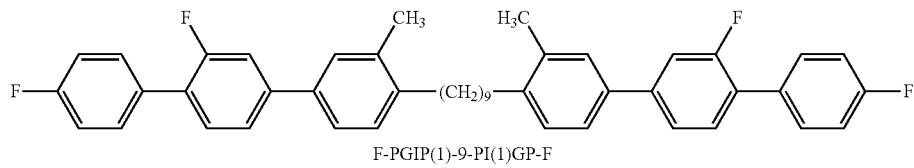

F-PGIP(1)-9-PI(1)GP-F

Phase sequence: K 85 (N2 67 N 88) I; T*(N,I)=80.5° C.; e/K=2.04 V$^{-1}$. (Remarks: "N2" second nematic phase and T*(N,I) and e/K extrapolated from 10% in host mixture H-0 with 2% of R-5011.)

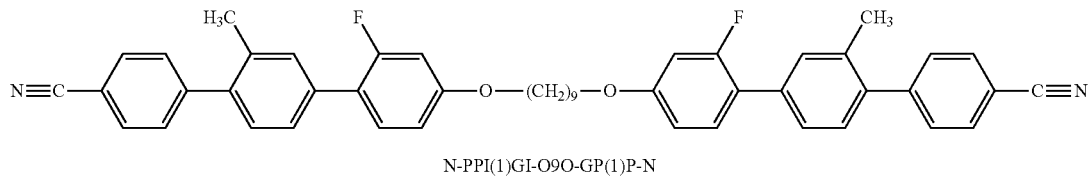

N-PPI(1)GI-O9O-GP(1)P-N

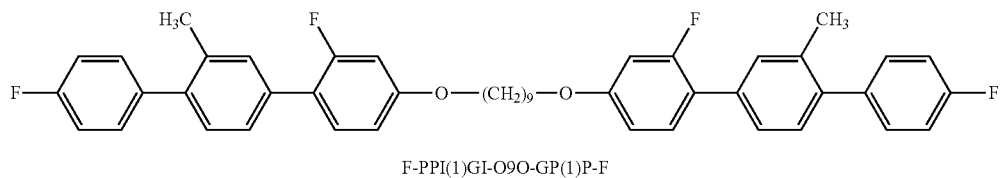

F-PPI(1)GI-O9O-GP(1)P-F

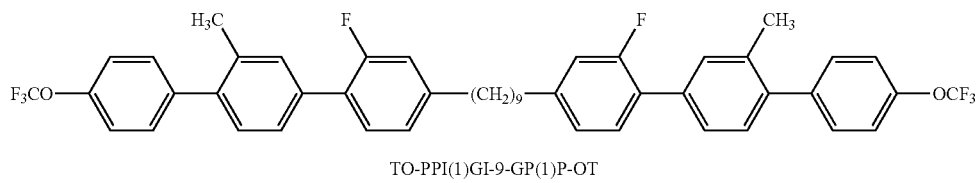

TO-PPI(1)GI-9-GP(1)P-OT

Phase sequence: K 62 N 68 I; T*(N,I)=82.0° C.; e/K=2.12 V$^{-1}$. (Remark: T*(N,I) and e/K extrapolated from 10% in host mixture H-0 with 2% of R-5011.)

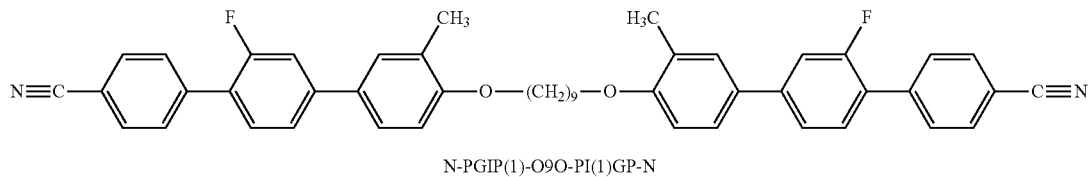

N-PGIP(1)-O9O-PI(1)GP-N

-continued

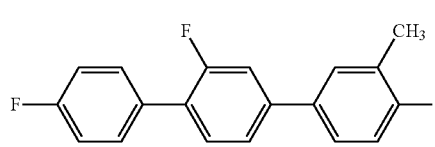
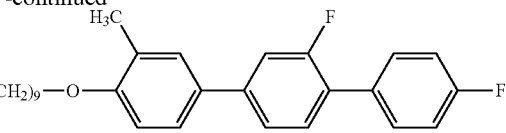

F-PGIP(1)-O9O-PI(1)GP-F

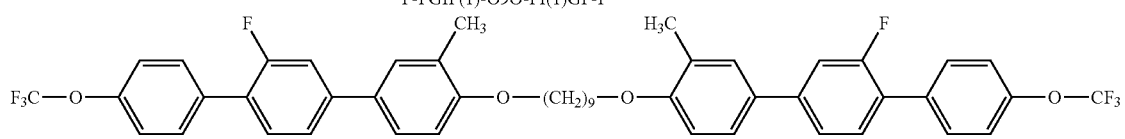

N-PGIP(1)-O9O-PI(1)GP-N

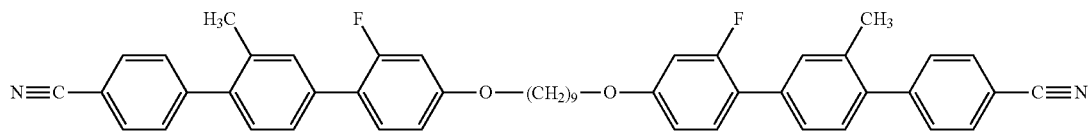

N-PPI(1)P-O9O-PP(1)P-N

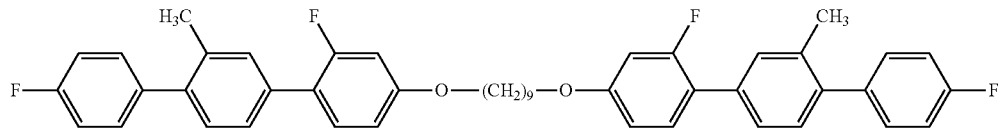

F-PPI(1)GI-O9O-GP(1)P-F

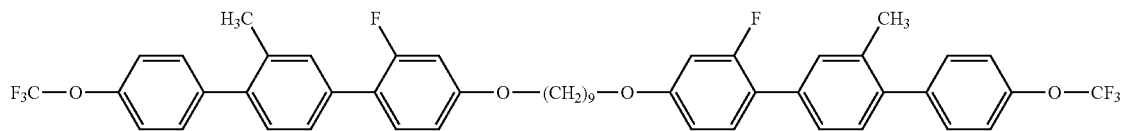

TO-PPI(1)GI-O9O-GP(1)P-OT

The materials in the above table generally showed increased performance in the screening mixtures, as compared to known, more conventional bimesogenic compounds as e.g. those shown in the table below.

Comparative Compound Examples

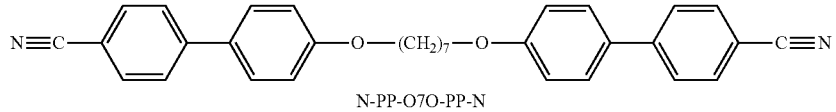

N-PP-O7O-PP-N

Phase sequence: K 137 N 181 I.

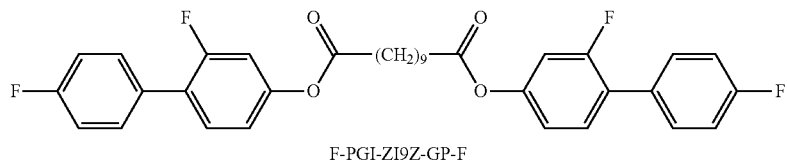

F-PGI-ZI9Z-GP-F

Phase sequence: K 88 (N 64) I.

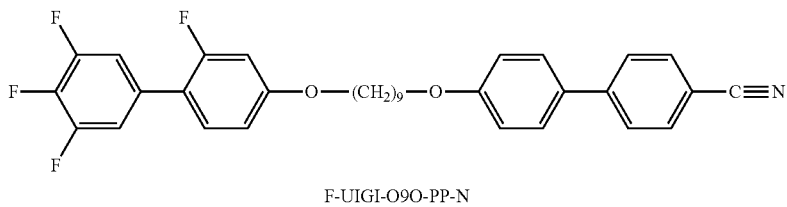

F-UIGI-O9O-PP-N

Phase sequence: K 98 (N 82.5) I.

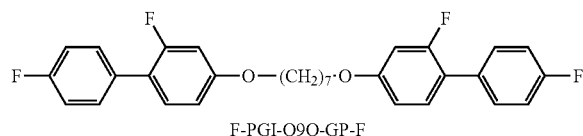

F-PGI-O9O-GP-F

Phase sequence: K 71.1 (N 50.5) I.

Use Examples, Mixture Examples

Typically a 5.6 μm thick cell, having an anti-parallel rubbed PI alignment layer, is filled on a hotplate at a temperature at which the flexoelectric mixture in the isotropic phase.

After the cell has been filled phase transitions, including clearing point, are measured using Differential Scanning Calorimetry (DSC) and verified by optical inspection. For optical phase transition measurements, a Mettler FP90 hot-stage controller connected to a FP82 hot-stage is used to control the temperature of the cell. The temperature is increased from ambient temperature at a rate of 5 degrees C. per minute, until the onset of the isotropic phase is observed. The texture change is observed through crossed polarizers using an Olympus BX51 microscope and the respective temperature noted.

Wires are then attached to the ITO electrodes of the cell using indium metal. The cell is secured in a Linkam THMS600 hot-stage connected to a Linkam TMS93 hot-stage controller. The hot-stage is secured to a rotation stage in an Olympus BX51 microscope.

The cell is heated until the liquid crystal is completely isotropic. The cell is then cooled under an applied electric field until the sample is completely nematic. The driving waveform is supplied by a Tektronix AFG3021B arbitrary function generator, which is sent through a Newtons4th LPA400 power amplifier before being applied to the cell. The cell response is monitored with a Thorlabs PDA55 photodiode. Both input waveforms and optical response are measured using a Tektronix TDS 2024B digital oscilloscope.

In order to measure the flexoelastic response of the material, the change in the size of the tilt of the optic axis is measured as a function of increasing voltage. This is achieved by using the equation:

$$\tan\varphi = \frac{P_o}{2\pi} \frac{e}{K} E$$

wherein $\varphi$ is the tilt in the optic axis from the original position (i.e. when E=0), E is the applied field, K is the elastic constant (average of $K_1$ and $K_3$) and e is the flexoelectric coefficient (where $e = e_1 + e_3$). The applied field is monitored using a HP 34401A multimeter. The tilt angle is measured using the aforementioned microscope and oscilloscope. The undisturbed cholesteric pitch, $P_0$, is measured using an Ocean Optics USB4000 spectrometer attached to a computer. The selective reflection band is obtained and the pitch determined from the spectral data.

The mixtures shown in the following examples are well suitable for use in USH-displays. To that end an appropriate concentration of the chiral dopant or dopants used has to be applied in order to achieve a cholesteric pitch of 200 nm or less.

Comparative Mixture Example 1.1

Host Mixture H-0

The host mixture H-0 is prepared and investigated.

| | Composition Compound | |
|---|---|---|
| No. | Abbreviation | Conc./% |
| 1 | F-PGI-O9O-GP-F | 25.0 |
| 2 | F-PGI-O9O-PP-N | 25.0 |
| 3 | F-PGI-ZI9Z-GP-F | 25.0 |
| 4 | F-PGI-ZI9Z-PP-N | 25.0 |
| Σ | | 100.0 |

2% of the chiral dopant R-5011 are added to the mixture H-0 leading to the mixture H-1, which is investigated for its properties.

| | Composition Compound | |
|---|---|---|
| No. | Abbreviation | Conc./% |
| 1 | R-5011 | 2.0 |
| 2 | F-PGI-O9O-GP-F | 24.5 |
| 3 | F-PGI-O9O-PP-N | 24.5 |
| 4 | F-PGI-ZI9Z-GP-F | 24.5 |
| 5 | F-PGI-ZI9Z-PP-N | 24.5 |
| Σ | | 100.0 |

The mixture H-1 may be used for the USH-mode. It has a clearing point of 82° C. and a lower transition temperature [T(N2,N)] of 33° C. It has a cholesteric pitch of 291 nm at 0.9 T(N,I). The e/K of this mixture is 1.80 $Cm^{-1}N^{-1}$ at 0.9 T(N,I).

Mixture Examples 1.1 to 1.14

2% of the chiral dopant R-5011 and 10% of the compound of synthesis example 1 are added to the mixture H-0 leading to the mixture M-1.1, which is investigated for its properties.

Mixture Example 1

Mixture M-1

| No. | Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | Compound 1 | 10.0 |
| Σ | | 100.0 |

Remark: *) Compound of Synthesis Example 1: N—PPI(1)-O9O—P(1)P—N.

This mixture (M-1) is prepared and investigated. It is well suitable for the ULH-mode.

It has a cholesteric pitch of 301.5 nm at 35° C.

The e/K of this mixture is 2.31 $Cm^{-1}N^{-1}$ at a temperature of 51° C.

The investigation described above is performed with 10% each of several compounds of formula I instead of that of synthesis example 1 used in host mixture H-0, together with 2% R-5011. The results are shown in the following table.

| Ex. | Mixt. | Compound | T(N, I)/ °C. | $T_{low}$/ °C. | P/ nm | e/K/ $V^{-1}$ |
|---|---|---|---|---|---|---|
| C1.1 | H-1.0 | None | 82 | 33 | 291 | 1.80 |
| C1.2 | H-1.1 | N-PP-9-PP-N | t.b.d. | 42 | t.b.d. | t.b.d. |
| C1.3 | H-1.2 | F-PGI-O7O-GP-F | 108 | 26.5 | 332 | 1.70 |
| E1.1 | M-1.1 | N-PPI(1)-O9O-P(1)P-N | 74.0 | t.b.d. | 302 | 1.83 |
| E1.2 | M-1.2 | N-P(1)P-O9O-PG-N | 81.9 | t.b.d. | t.b.d. | 1.76 |
| E1.3 | M-1.3 | N-PPI(1)-9-P(1)P-N | 70.8 | 29.0 | 307 | 2.28 |
| E1.4 | M-1.4 | N-PPI(1)-ZI9Z-P(1)P-N | 77.9 | t.b.d. | 320 | 2.17 |
| E1.5 | M-1.5 | N-P(1)P-O9O-PP(1)-N | 78.6 | 25.0 | 309 | 1.87 |
| E1.6 | M-1.6 | N-PP(1)-O9O-PI(1)P-N | 75.2 | 34.0 | 301 | 2.25 |
| E1.7 | M-1.7 | F-PPI(1)P-ZI9Z-PP(1)P-F | 89.0 | 32.0 | 325 | 1.94 |
| E1.8 | M-1.8 | N-PPI(1)GI-9-GP(1)P-F | 85.0 | 39.0 | 276 | 2.24 |
| E1.9 | M-1.9 | N-PPI(2)-O9O-P(2)P-N | 73.0 | t.b.d. | 299 | 2.07 |
| E1.10 | M-1.10 | F-PP(1)-9-PI(1)P-F | 76.0 | 27.0 | 302 | 1.97 |
| E1.11 | M-1.11 | N-PGI-ZI9Z-PI(1)P-N | 84.0 | 30.5 | 302 | 2.02 |
| E1.12 | M-1.12 | N-PGIP(1)-9-PI(1)GP-N | 88.6 | 40.0 | 297 | 2.14 |
| E1.13 | M-1.13 | F-PGIP(1)-9-PI(1)GP-F | 80.5 | 39.0 | 289 | 2.04 |
| E1.14 | M-1.14 | TO-PPI(1)GI-9-GP(1)P-OT | 82.0 | 39.0 | 299 | 2.12 |

Remarks: the cholesteric pitch (P) is given at 0.9 T(N,I) and e/K is given in $V^{-1}$ (i.e. $Cm^{-1}N^{-1}$) at 0.9 T(N,I).

Comparative Mixture Example 1.2

Mixture H-1.1

The following mixture is prepared (Mixture H-1.1) and investigated.

| No. | Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | N-PP-9-PP-N | 10.0 |
| Σ | | 100.0 |

This mixture, mixture H-1.1, shows an N to N2 transition at 42° C.

Comparative Mixture Example 1.3

Mixture H-1.2

The following mixture is prepared (Mixture H-1.1) and investigated.

| No. | Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | F-PGI-O7O-GP-F | 10.0 |
| Σ | | 100.0 |

This mixture, mixture H-1.2, has a clearing point of 108° C. and shows an N to N2 transition at 26.5° C. It has a cholesteric pitch of 332 nm at 0.9 T(N,I).

The e/K of this mixture is 1.70 $Cm^{-1}N^{-1}$ at 0.9 T(N,I), i.e. at a temperature of 70° C.

Mixture Example 2

Mixture M-2

The following mixture (Mixture M-2) is prepared and investigated.

| No. | Abbreviation | Conc./% |
|---|---|---|
| 1 | R-5011 | 1.7 |
| 2 | N-GIGI-ZI9Z-GG-N | 3.9 |
| 3 | F-PGI-ZI9Z-GP-F | 13.8 |
| 4 | F-UIGI-ZI-9Z-GP-N | 22.3 |
| 5 | N-PGI-O11O-GP-N | 11.3 |
| 6 | N-GIGI-9-GG-N | 19.7 |
| 7 | N-UIUI-9-UU-N | 5.0 |

-continued

| No. | Abbreviation | Conc./% |
|---|---|---|
| 8 | N-GIUIGI-9-GUG-N | 7.4 |
| 9 | Example Compound 1 | 4.1 |
| 10 | CC-3-V | 9.1 |
| 11 | PPP-5-N | 3.7 |
| Σ | | 100.0 |

Composition Compound

Remark: *) Compound of Synthesis Example 1: N—PP—SCO-9-COS—PP—N.

This mixture, mixture M-2, has a suitable a clearing point [T(N,I)] and is well suitable for the ULH-mode. It has an excellent response time for switching on ($\tau_{on}$, driven) and for switching off ($\tau_{off}$, relaxation), respectively.

The invention claimed is:

1. A bimesogenic compound of formula I

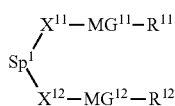

wherein
- $R^{11}$ $R^{12}$ are each independently a straight-chain or branched alkyl group with 1 to 25 C atoms, a straight chain or branched alkoxy group having 1 to 24 C atoms, a straight chain or branched oxaalkyl group having 1 to 24 C atoms, CN, $NO_2$, halogen, $OCH_3$, OCN, SCN, $COR^X$, $COOR^X$ or a mono- oligo- or polyfluorinated alkyl or alkoxy group with 1 to 4 C atoms,
- $R^X$ is optionally fluorinated alkyl with 1 to 4 C atoms,
- $MG^{11}$ and $MG^{12}$ are each independently a mesogenic group and at least one of $MG^{11}$ and $MG^{12}$ comprises one, two or more 6-atomic rings, and at least one of $MG^{11}$ and $MG^{12}$ comprises two or more 6-atomic rings,
- $Sp^1$ is a spacer group comprising 1, 3 or 5 to 40 C atoms, wherein one or more non-adjacent groups are each optionally replaced by —O—, —S—, —NH—, —N($CH_3$)—, —O—CO—, —CO—O—, —S—CO—, —O—CO—O—, —CO—S—, —S—CO—, —CH(halogen)-, —CH(CN)—, —CH=CH— or —C≡C—, in such a way that no two O-atoms are adjacent to one another, no two —CH=CH— groups are adjacent to each other, and no two groups selected from —O—CO—, —CO—O—, —S—CO—, —O—CO—O—, —CO—S—, —S—CO—, —O—CO—, and —CH=CH— are adjacent to each other,
- $X^{11}$ and $X^{12}$ are each independently of one another a group selected from —CH=CH—, —C≡C—, —O—, —CO—O—, —O—CO—, —O—CO—O—, —S—, —S—CS—, —CS—S—, —CO—S—, —S—CO—, —S—CS—, —S—CO—S— and —S—CS—S— or a single bond,
under the condition that in —$X^{11}$-$Sp_1$-$X^{12}$— no two O atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other, and
at least one of $MG^{11}$ and $MG^{12}$ is 1,4-phenylene, which is substituted by at least one alkyl group having 1 to 5 C atoms, or comprises a 1,4-phenylene, which is substituted by at least one alkyl group having 1 to 5 C atoms.

2. A compound according to claim 1, wherein $MG^{11}$ and $MG^{12}$ are independently of each other selected of partial formula II

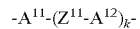     II wherein
- $Z^{11}$ are, independently of each other in each occurrence, a single bond, —COO—, —OCO—, —O—CO—O—, —$OCH_2$—, —$CH_2O$—, —$OCF_2$—, —$CF_2O$—, —$CH_2CH_2$—, —$(CH_2)_4$—, —$CF_2CF_2$—, —CH=CH—, —CF=CF—, —CH=CH—COO—, —OCO—CH=CH— or —C≡C—, optionally substituted with one or more of F, S and/or Si,
- $A^{11}$ and $A^{12}$ are each independently in each occurrence 1,4-phenylene, wherein in addition one or more CH groups are each optionally replaced by N, trans-1,4-cyclo-hexylene in which, in addition, one or two non-adjacent $CH_2$ groups are each optionally replaced by O and/or S, 1,4-cyclohexenylene, 1,4-bicyclo-(2,2,2)-octylene, piperidine-1,4-diyl, naphthalene-2,6-diyl, decahydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1] decane-2,8-diyl, it being possible for all these groups to be unsubstituted, mono-, di-, tri- or tetrasubstituted with F, Cl, CN or alkyl, alkoxy, alkylcarbonyl or alkoxycarbonyl groups each with up to 7 C atoms, wherein one or more H atoms are each optionally replaced by F or Cl, and
- k is 0, 1, 2, 3 or 4, and
at least one of $MG^{11}$ and $MG^{12}$ is 1,4-phenylene, which is substituted by at least one alkyl group having 1 to 5 C atoms, or comprises a 1,4-phenylene, which is substituted by at least one alkyl group having 1 to 5 C atoms.

3. A compound according to claim 1, wherein $MG^{11}$ and $MG^{12}$ are each independently of one another selected from the group of formulae II-1 to 11-26

| | |
|---|---|
| -Phe-Z-Phe- | II-1 |
| -Phe-Z-Cyc- | II-2 |
| -Cyc-Z-Cyc- | II-3 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |

| | |
|---|---|
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| -Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 | wherein
Cyc is 1,4-cyclohexlene,
Phe is 1,4-phenylene or alkyl-1,4-phenylene,
PheL is 1,4-phenylene, which is substituted by one, two or three fluorine atoms, by one or two Cl atoms or by one Cl atom and one F atom, and
Z are, independently of each other in each occurrence, a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH═CH—, —CF═CF—, —CH═CH—COO—, —OCO—CH═CH— or —C≡C—, optionally substituted with one or more of F, S and/or Si, and
at least one of MG$^{11}$ and MG$^{12}$ comprises a 1,4-phenylene, which is substituted by at least one alkyl group having 1 to 5 C atoms.

4. A compound according to claim 1, wherein R$^{11}$ and R$^{12}$ are independently of one another selected from OCF$_3$, CF$_3$, F, Cl and CN.

5. A compound according to claim 1, wherein Sp$^1$ is —(CH$_2$)$_o$— and O is 1, 3 or an integer from 5 to 15.

6. A liquid-crystalline medium comprising one or more bimesogenic compounds according to claim 1.

7. The liquid-crystalline medium according to claim 6, further comprising one or more compounds of formula III R$^{31}$-MG$^{31}$-X$^{31}$-Sp$^3$-X$^{32}$-MG$^{32}$-R$^{32}$  III wherein
R$^{31}$ and R32 are each independently H, F, Cl, CN, NCS or a straight-chain or branched alkyl group with 1 to 25 C atoms which is unsubstituted, or mono- or polysubstituted by halogen or CN, wherein one or more non-adjacent CH$_2$ groups are each optionally replaced, in each case independently from one another, by —O—, —S—, —NH—, —N(CH$_3$)—, —CO—, —COO—, —OCO—, —O—CO—O—, —S—CO—, —CO—S—, —CH═CH—, —CH═CF—, —CF═CF— or —C≡C— in such a manner that oxygen atoms are not linked directly to one another, MG$^{31}$ and MG$^{32}$ are each independently a mesogenic group,
Sp$^3$ is a spacer group comprising 5 to 40 C atoms, wherein one or more non-adjacent CH$_2$ groups are each optionally replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH═CH— or —C≡C—, and
X$^{31}$ and X$^{32}$ are each independently —O—, —S—, —CO—, —COO—, —OCO—, —O—CO—O—, —CO—NH—, —NH—CO—, —CH$_2$CH$_2$—, —OCH$_2$—, —CH$_2$O—, —SCH$_2$—, —CH$_2$S—, —CH═CH—, —CH═CH—COO—, —OCO—CH═CH—, —C≡C— or a single bond, and
with the condition that compounds of formula I are excluded.

8. A liquid crystal device comprising a liquid crystalline medium comprising two or more components, one or more of which is a bimesogenic compound according to claim 1.

9. The liquid crystal device according to claim 8, wherein said device is a flexoelectric device.

10. A compound according to claim 1, wherein at least one of MG$^{11}$ and MG$^{12}$ is 1,4-phenylene, which is substituted by CH$_3$ or C$_2$H$_5$.

11. A compound according to claim 1, wherein —X$^{11}$-Sp$^1$-X$^{12}$— is —O—CO-Sp$^1$-CO—O—, —O-Sp$^1$-O—, -Sp$^1$- or —S—CO-Sp$^1$-CO—S—,
Sp$^1$ is —(CH$_2$)$_n$—, and
n 1, 3 or an integer from 5 to 15,
wherein one or more H atoms in -(CH$_2$)$_n$— are each optionally, independently of each other, replaced by F or CH$_3$.

12. A compound according to claim 2, wherein —X$^{11}$-Sp$^1$-X$^{12}$— is —O—CO-Sp$^1$-CO—O—, —O-Sp$^1$-O—, -Sp$^1$- or —S—CO-Sp$^1$-CO—S—,
Sp$^1$ is —(CH$_2$)$_n$—, and
n 1, 3 or an integer from 5 to 15,
wherein one or more H atoms in —(CH$_2$)$_n$— are each optionally, independently of each other, replaced by F or CH$_3$.

13. A compound according to claim 3, wherein —X$^{11}$-Sp$^1$-X$^{12}$— is —O—CO-Sp$^1$-CO—O—, —O-Sp$^1$-O—, -Sp$^1$- or —S—CO-Sp$^1$-CO—S—,
Sp$^1$ is —(CH$_2$)$_n$—, and
n 1, 3 or an integer from 5 to 15,
wherein one or more H atoms in —(CH$_2$)— are each optionally, independently of each other, replaced by F or CH$_3$.

14. A compound according to claim 3, wherein MG$^{11}$ and MG$^{12}$ are each independently of one another selected from the group of formulae II-1, II-4, II-5, II-7, II-8, II-14, II-15, II-16, II-17, II-18, and II-19.

15. A compound according to claim 1, wherein MG$^{11}$ and MG$^{12}$ are each independently of one another selected from the following formulae IIa to IIo and their mirror images

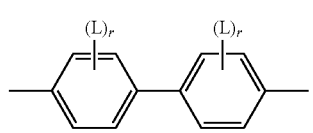

IIa

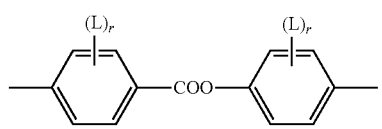

IIb

-continued

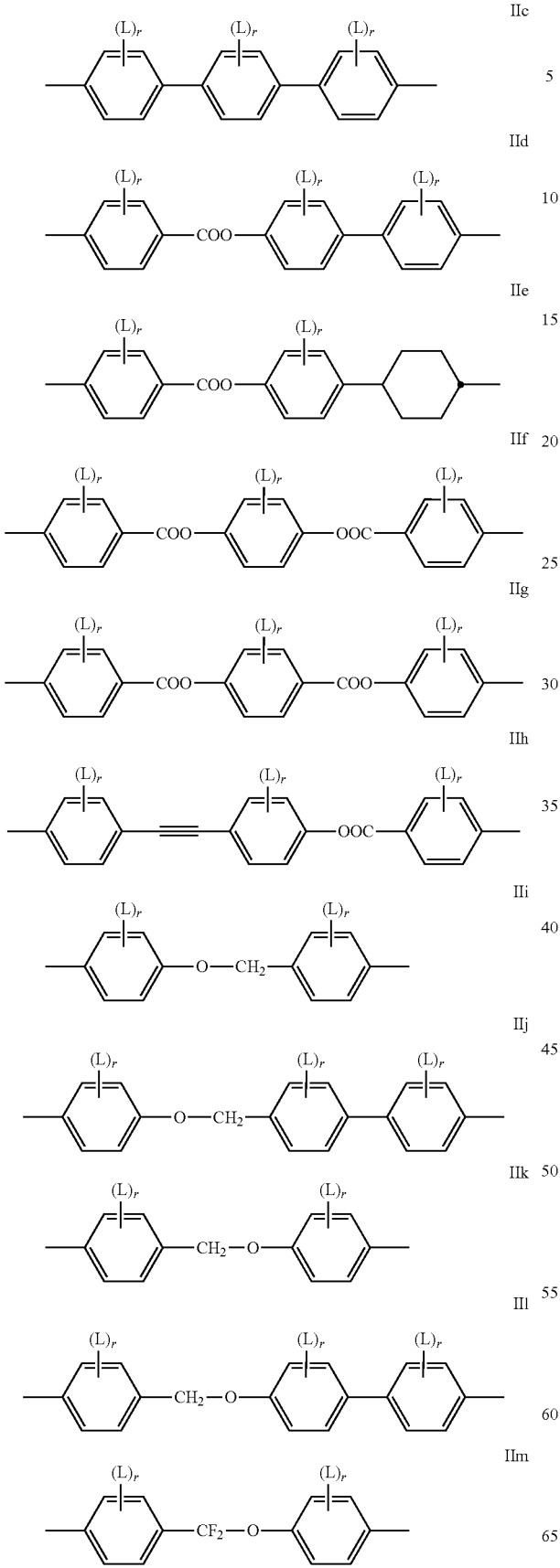

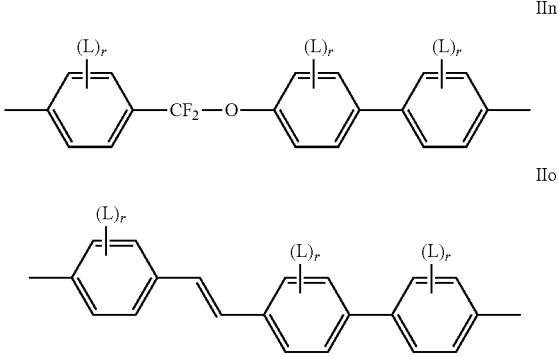

wherein
L is in each occurrence independently of each other R, F or Cl,
r is in each occurrence independently of each other 0, 1, 2 or 3,
R is alkyl having 1 to 5 C-atoms, and
at least one L present in at least one of $MG^{11}$ and $MG^{12}$ is R.

16. A compound according to claim 15, wherein $MG^{11}$ and $MG^{12}$ are each independently of one another selected from formulae IIa-1, IIa-2, IIc-1 and IIc-2

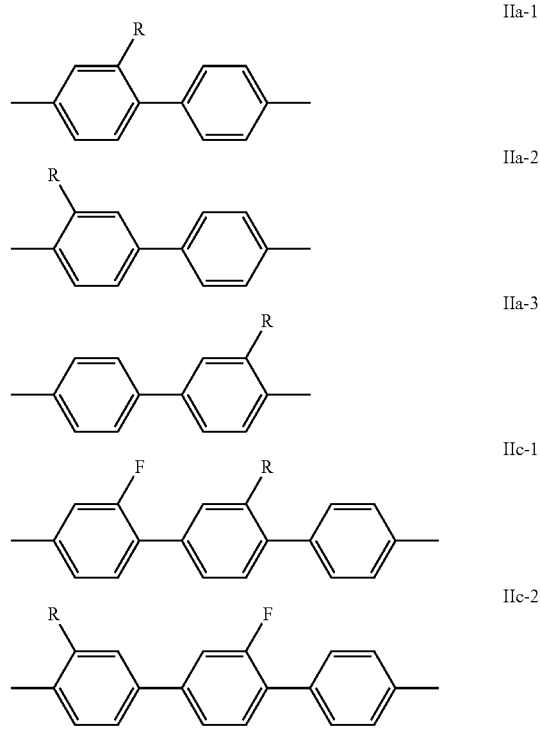

wherein
R is alkyl having 1 to 5 C-atoms.

17. A compound according to claim 1, wherein said compound is selected from the group of compounds of formulae IA to IC,

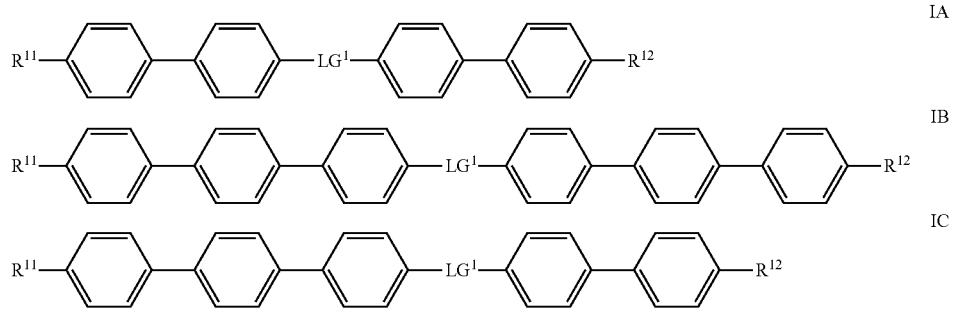

IA
IB
IC wherein
LG$^1$ is —X$^{11}$-Sp$^1$-X$^{12}$—, and
X$^{11}$, X$^{12}$, Sp$^1$, R$^{11}$ and R$^{12}$ are as defined in claim 1, and
at least one of the 1,4-phenylene rings is substituted by an alkyl group and all of the 1,4-phenylene rings are optionally substituted by one or more F or Cl-atoms.

18. A compound according to claim 17, wherein said compound is selected from the group of compounds of formulae IA-1 to IA-4, IB-1 to IB-3, and IC-1 to IC-3

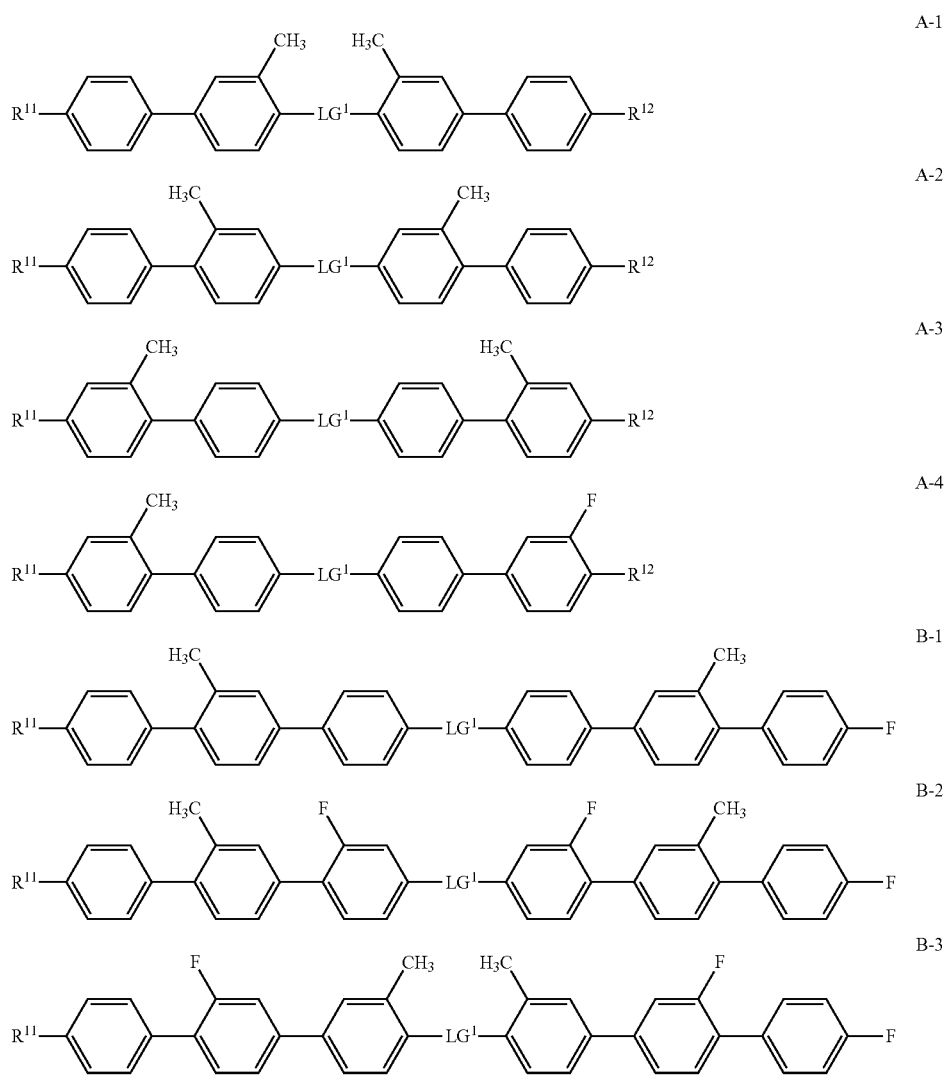

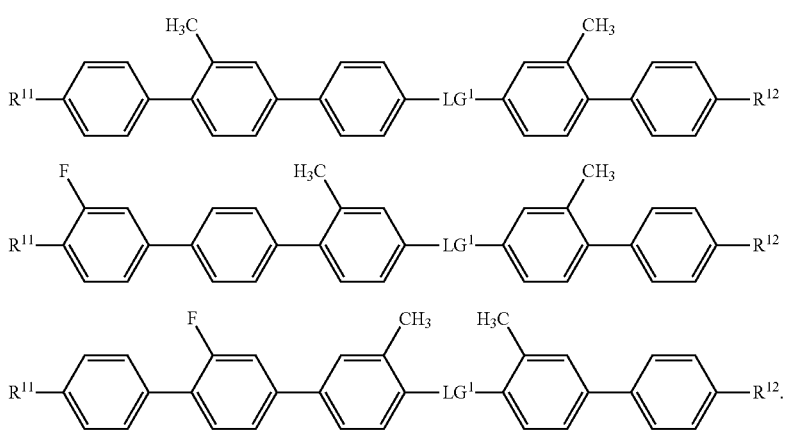

19. A compound according to claim 18, wherein $R^{11}$ and $R^{12}$ are each, independently from each other, $OCF_3$, $CF_3$, F or CN.

20. A compound according to claim 17, wherein
LG$^1$ is —O—CO-Sp$^1$-CO—O—, —O-Sp$^1$-O—, -Sp$^1$- or —S—CO-Sp$^1$-CO—S—,
Sp$^1$ is —(CH$_2$)$_n$—,
n is 1, 3 or an integer from 5 to 15.

21. A compound according to claim 18, wherein
LG$^1$ is —O—CO-Sp$^1$-CO—O—, —O-Sp$^1$-O—, -Sp$^1$- or —S—CO-Sp$^1$-CO—S—,
Sp$^1$ is —(CH$_2$)$_n$—,
n is 1, 3 or an integer from 5 to 15.

22. A compound according to claim 1, wherein $R^{11}$ and $R^{12}$ are each, independently from each other, ethyl, propyl, butyl, pentyl, hexyl, heptyl, octyl, ethoxy, propoxy, butoxy, pentoxy, hexoxy, heptoxy, octoxy, methyl, nonyl, decyl, undecyl, dodecyl, tridecyl, tetradecyl, pentadecyl, nonoxy, decoxy, undecoxy, dodecoxy, tridecoxy, or tetradecoxy.

23. A bimesogenic compound of formula I

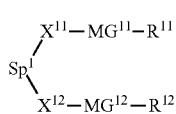

I wherein
$R^{11}$ and $R^{12}$ each, independently from each other, H, F, Cl, CN, NO$_2$, OCH$_3$, COCH$_3$, COC$_2$H$_5$, COOCH$_3$, COOC$_2$H$_5$, CF$_3$, C$_2$F$_5$, OCF$_3$, OCHF$_2$, or OC$_2$F$_5$,
MG$^{11}$ and MG$^{12}$ are each independently a mesogenic group and at least one of MG$^{11}$ and MG$^{12}$ comprises one, two or more 6-atomic rings, and at least one of MG$^{11}$ and MG$^{12}$ comprises two or more 6-atomic rings,
Sp$^1$ is a spacer group comprising 1, 3 or 5 to 40 C atoms, wherein one or more non-adjacent groups are each optionally replaced by —O—, —S—, —NH—, —N(CH$_3$)—, —O—CO—, —CO—O—, —S—CO—, —O—CO—O—, —CO—S—, —S—CO—, —CH(halogen)-, —CH(CN)—, —CH=CH— or —C≡C—, in such a way that no two O-atoms are adjacent to one another, no two —CH=CH— groups are adjacent to each other, and no two groups selected from —O—CO—, —CO—O—, —S—CO—, —O—CO—O—, —CO—S—, —S—CO—, —O—CO—, and —CH=CH— are adjacent to each other,
$X^{11}$ and $X^{12}$ are each independently of one another a group selected from —CH=CH—, —C≡C—, —O—, —CO—O—, —O—CO—, —O—CO—O—, —S—, —S—CS—, —CS—S—, —CO—S—, —S—CO—, —S—CS—, —S—CO—S— and —S—CS—S— or a single bond,
under the condition that in —X$^{11}$-Sp$^1$-X$^{12}$— no two O atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other, and
at least one of MG$^{11}$ and MG$^{12}$ is 1,4-phenylene, which is substituted by at least one alkyl group having 1 to 5 C atoms, or comprises a 1,4-phenylene, which is substituted by at least one alkyl group having 1 to 5 C atoms.

24. A liquid-crystalline medium comprising:
(a) a bimesogenic compound of formula I

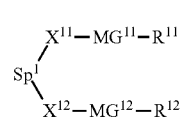

I wherein
$R^{11}$ and $R^{12}$ are each independently H, F, Cl, CN, NCS or a straight-chain or branched alkyl group with 1 to 25 C atoms which is unsubstituted or mono- or polysubstituted by halogen or CN, wherein one or more non-adjacent CH$_2$ groups are each optionally replaced, in each occurrence independently from one another, by —O—, —S—, —N(CH$_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another,
MG$^{11}$ and MG$^{12}$ are each independently a mesogenic group and at least one of MG$^{11}$ and MG$^{12}$ comprises one, two or more 6-atomic rings, and at least one of MG$^{11}$ and MG$^{12}$ comprises two or more 6-atomic rings, Sp$^1$ is a spacer group comprising 1, 3 or 5 to 40 C atoms, wherein one or more non-adjacent groups are each optionally replaced by —O—, —S—, —NH—, —N(CH$_3$)—, —O—CO—, —CO—O—, —S—CO—, —O—CO—O—, —CO—S—, —S—CO—, —CH(halogen)-, —CH(CN)—, —CH=CH— or —C≡C—, in such a way that no two O-atoms are adjacent to one another, no two —CH=CH—groups are adjacent to each other, and no two groups selected from —O—CO—, —CO—O—, —S—CO—, —O—CO—O—, —CO—S—, —S—CO—, —O—CO—, and —CH=CH— are adjacent to each other, X$^{11}$ and X$^{12}$ are each independently of one another a group selected from —CH=CH—, —C≡C—, —O—, —CO—O—, —O—CO—, —O—CO—O—, —S—, —S—CS—, —CS—S—, —CO—S—, —S—CO—, —S—CS—, —S—CO—S— and —S—CS—S— or a single bond, under the condition that in —X$^{11}$-Sp$^1$-X$^{12}$— no two O atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other, and at least one of MG$^{11}$ and MG$^{12}$ is 1,4-phenylene, which is substituted by at least one alkyl group having 1 to 5 C atoms, or comprises a 1,4-phenylene, which is substituted by at least one alkyl group having 1 to 5 C atoms; and (b) one or more compounds of formula III R$^{31}$-MG$^{31}$-X$^{31}$-Sp$^3$-X$^{32}$-MG$^{32}$-R$^{32}$  III wherein R$^{31}$ and R$^{32}$ are each independently H, F, Cl, CN, NCS or a straight-chain or branched alkyl group with 1 to 25 C atoms which is unsubstituted, or mono- or polysubstituted by halogen or CN, wherein one or more non-adjacent CH$_2$ groups are each optionally replaced, in each case independently from one another, by —O—, —S—, —NH—, —N(CH$_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another, MG$^{31}$ and MG$^{32}$ are each independently a mesogenic group, Sp$^3$ is a spacer group comprising 5 to 40 C atoms, wherein one or more non-adjacent CH$_2$ groups are each optionally replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH=CH— or —C≡C—, and X$^{31}$ and X$^{32}$ are each independently —O—, —S—, —CO—, —COO—, —OCO—, —O—CO—O—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond, and with the condition that compounds of formula I are excluded from formula III.

25. A liquid crystal device comprising a liquid crystalline medium according to claim 24.

26. The liquid crystal device according to claim 25, wherein said device is a flexoelectric device.

* * * * *